(12) United States Patent
Zebala

(10) Patent No.: US 9,717,700 B2
(45) Date of Patent: *Aug. 1, 2017

(54) METHODS FOR OVERCOMING RESISTANCE TO TRAMADOL

(71) Applicant: Syntrix Biosystems, Inc., Auburn, WA (US)

(72) Inventor: John A. Zebala, Issaquah, WA (US)

(73) Assignee: Syntrix Biosystems Inc., Auburn, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/949,434

(22) Filed: Nov. 23, 2015

(65) Prior Publication Data

US 2016/0074341 A1 Mar. 17, 2016

Related U.S. Application Data

(60) Continuation of application No. 14/821,506, filed on Aug. 7, 2015, which is a division of application No. 13/543,883, filed on Jul. 8, 2012.

(Continued)

(51) Int. Cl.
*A61K 31/135* (2006.01)
*A61K 9/00* (2006.01)
(Continued)

(52) U.S. Cl.
CPC .......... *A61K 31/135* (2013.01); *A61K 9/0053* (2013.01); *A61K 9/2054* (2013.01);
(Continued)

(58) Field of Classification Search
CPC .... A61K 45/06; A61K 31/135; A61K 9/2054; A61K 9/2866; A61K 9/0053; A61K 9/2059; A61K 9/28
See application file for complete search history.

(56) References Cited

U.S. PATENT DOCUMENTS 3,652,589 A 3/1972 Flick et al.
3,845,770 A 11/1974 Theeuwes et al.
(Continued)

FOREIGN PATENT DOCUMENTS

DE 19712398 A1 10/1998
WO WO 97/47285 A1 12/1997
(Continued)

OTHER PUBLICATIONS

Lai et al.; "Tramadol, M1 metabolite and enantiomer affinities for cloned human opioid receptors expressed in transfected HN9.10 neuroblastoma cells"; European Journal of Pharmacology; vol. 316; 1996; p. 369-372.
(Continued)

*Primary Examiner* — Brian-Yong Kwon
*Assistant Examiner* — Hong Yu
(74) *Attorney, Agent, or Firm* — Baker & Hostetler LLP

(57) ABSTRACT

There is disclosed a method for treating disorders modulated by at least opiate receptor activity or monoamine activity, including acute and chronic pain, comprising administering a pharmaceutical formulation comprising O-desmethyltramadol. Methods are also provided that are effective for overcoming resistance to tramadol in patients.

21 Claims, 20 Drawing Sheets

Related U.S. Application Data

(60) Provisional application No. 61/506,092, filed on Jul. 9, 2011.

(51) Int. Cl.
- A61K 45/06 (2006.01)
- A61K 9/20 (2006.01)
- A61K 9/28 (2006.01)

(52) U.S. Cl.
CPC ............ *A61K 9/2059* (2013.01); *A61K 9/28* (2013.01); *A61K 9/2866* (2013.01); *A61K 45/06* (2013.01)

(56) References Cited

U.S. PATENT DOCUMENTS

| | | |
|---|---|---|
| 3,916,899 A | 11/1975 | Theeuwes et al. |
| 4,008,719 A | 2/1977 | Theeuwes et al. |
| 4,014,334 A | 3/1977 | Theeuwes et al. |
| 4,058,122 A | 11/1977 | Theeuwes et al. |
| 4,116,241 A | 9/1978 | Theeuwes et al. |
| 4,160,452 A | 7/1979 | Theeuwes |
| 4,844,909 A | 7/1989 | Goldie et al. |
| 5,023,083 A | 6/1991 | Drell |
| 5,336,691 A | 8/1994 | Raffa et al. |
| 5,427,799 A | 6/1995 | Valentine et al. |
| 5,468,744 A | 11/1995 | Raffa et al. |
| 5,516,803 A | 5/1996 | Raffa |
| 5,580,578 A | 12/1996 | Oshlack et al. |
| 5,591,452 A | 1/1997 | Miller et al. |
| 5,622,722 A | 4/1997 | Knott et al. |
| 5,728,885 A | 3/1998 | Buschmann et al. |
| 5,968,551 A | 10/1999 | Oshlack et al. |
| 6,017,963 A | 1/2000 | Alfonso et al. |
| 6,090,411 A | 7/2000 | Pillay et al. |
| 6,120,803 A | 9/2000 | Wong et al. |
| 6,143,327 A | 11/2000 | Seth |
| 6,245,357 B1 | 6/2001 | Edgren et al. |
| 6,254,887 B1 | 7/2001 | Miller et al. |
| 6,297,286 B1 | 10/2001 | Huckle |
| 6,326,404 B1 | 12/2001 | Koegel et al. |
| 6,339,105 B1 | 1/2002 | Mamin et al. |
| 6,387,956 B1 | 5/2002 | Shapira et al. |
| 6,455,585 B1 | 9/2002 | Del Castillo et al. |
| 6,562,865 B1 * | 5/2003 | Codd ............... A61K 31/195 514/456 |
| 6,593,373 B2 | 7/2003 | Koegel et al. |
| 6,660,774 B2 | 12/2003 | Christoph et al. |
| 6,723,343 B2 | 4/2004 | Kugelmann |
| 6,780,891 B2 | 8/2004 | Senanayake et al. |
| 6,894,076 B2 | 5/2005 | Mourelle Mancini et al. |
| 6,974,839 B2 | 12/2005 | Bar-Or |
| 7,074,430 B2 | 7/2006 | Miller et al. |
| 7,611,730 B2 | 11/2009 | Bartholomaus et al. |
| 7,906,141 B2 | 3/2011 | Ziegler et al. |
| 8,367,107 B2 | 2/2013 | Ishitsubo |
| 8,372,432 B2 | 2/2013 | Han et al. |
| 8,486,448 B2 | 7/2013 | Rahmouni et al. |
| 8,895,066 B2 | 11/2014 | Bichara et al. |
| 2002/0156066 A1 | 10/2002 | Chen et al. |
| 2003/0077222 A1 | 4/2003 | Leyland-Jones |
| 2004/0132798 A1 | 7/2004 | Carlsson et al. |
| 2004/0248979 A1 | 12/2004 | Brettman et al. |
| 2006/0147527 A1 | 7/2006 | Bachmann et al. |
| 2007/0105785 A1 | 5/2007 | Fraser et al. |
| 2007/0190117 A1 | 8/2007 | Asmussen et al. |
| 2009/0082466 A1 | 3/2009 | Babul |
| 2009/0238873 A1 | 9/2009 | Chattaraj et al. |
| 2010/0010029 A1 | 1/2010 | Maichle et al. |
| 2010/0104638 A1 | 4/2010 | Dai et al. |
| 2010/0210732 A1 * | 8/2010 | Babul ............... A61K 31/405 514/646 |
| 2013/0011444 A1 | 1/2013 | Zebala |
| 2015/0342905 A1 | 12/2015 | Zebala |
| 2016/0074341 A1 | 3/2016 | Zebala |

FOREIGN PATENT DOCUMENTS

| | | |
|---|---|---|
| WO | WO 01/24783 A2 | 4/2001 |
| WO | WO 01/24783 A3 | 4/2001 |
| WO | WO 02/066025 A2 * | 8/2002 |
| WO | WO 02/066025 A3 | 8/2002 |

OTHER PUBLICATIONS

Sevcik et al.; "Effects of the central analgesic tramadol and its main metabolite, 0-desmethyltramadol, on rat locus coeruleus neurones"; British Journal of Pharmacology; vol. 110; 1993; p. 169-176.

Wiebalck et al., "Sind Tramadoi-Enantiomere fur die postoperative Schmerztherapie besser geeignet als das Racemat?" Anaesthesist, 47:387-394, 1998 (abstract).

Vlase et al. Talanta 75:1104-1109, 2008.

Shao et al. In vitro and in vivo evaluation of 0-alkyl derivatives of tramadol Bioorg. Med. Chem. Lett. 18:1674-1680, 2008.

Shao et al. 2 Derivatives of tramadol for increased duration of effect Bioorg. Med. Chem. Lett. 16:691-694, 2006.

Pypendop et al. "Pharmacokinetics of tramadol, and its metabolite)-desmethyl-tramadol in cats" J. Vet. Pharmacal. Ther. 31:52-59, 2007.

McMilan et al. Pharmaqcokinetics of intravenous tramadol in dogs Canadian J. Vet. Res. 72:325-331, 2008.

Matthiesen et al. The experimental toxicology of tramadol: an overview Tox. Lett. 95:63-71, 1998.

Grond et al. Serum concentrations of tramadol enantiomers during patient-controlled analgesia Br. J. Clin. Pharmacal. 48:254-257, 1999.

Grond et al.2 Analgesic efficacy and safety of tramadol enantiomers in comparison with the racemate: a randomized, double-blind study with gynaecological patients using intravenous patient-controlled analgesia Pain 62:313-320, 1995.

Giorgi et ai.Pharmacokinetic evaluation of tramadol and its major metabolites after single oral sustained tablet administration in the dog: a pilot study The Veterinary J. 2008.

Enggaard et al. The analgesic effect of tramadol after intravenous injection in healthy volunteers in relation to CYP2D6 Anesth. Analg. 102:146-150, 2006.

Ding et al. Human extrahepatic cytochromes P450: Function in xenobiotic metabolism and tissue-selective chemical toxicity in the respiratory and gastrointestinal tracts Annu. Rev. Pharmacal. Toxicol. 43:149-173, 2003.

Desousa et al. Pharmacokinetics of tramadol and 0-desmethyltramadol in goats after intravenous and oral administration J. vet. Pharmacal. Therap. 31:45-51, 2007.

Beier et al. Semi-mechanistic pharmacokinetic/pharmacodynamic modeling of antinociceptyive response in the presence of competitive antagonism Pharmaceutical Res. 25:1789-1797, 2007.

Bamigbade et al. Actions of tramadol, its enantiomers and principal metabolit, )-desmethyltramadol, on serotonin (5-HT) efflux and uptake in the rat dorsal raphe nucleus Br. J. Anaesthesia 79:352-356, 1997.

Ardakani et al. Improved liquid chromatographic method for the simultaneous determination of tramadol and its three main metabolites in human plasma, urine and saliva J. Pharmaceutical Biomed. Analysis 44:1168-1173, 2007.

Ardakani et al. Enantioselective deytermination of tramadol and its main phase I metabolites in human plasma by high-performance liquid chromatography J. Chromatography 864:109-115, 2008.

Raffa et al. I, "Opioid and nonopioid components independently contribute to the mechanism of action of tramadol, an 'atypical' opioid analgesic" J. Pharmacal. Exp. Ther., 1992. 260(1): p. 275-85).

Raffa, "Basic pharmacology relevant to drug abuse assessment: tramadol as example" J. Clin. Pharm. Ther., 2008. 33(2): p. 101-8).

Kayser et al. I, "Effects of the analgesic agent tramadol in normal and arthritic rats: comparison with the effects of different opioids, including tolerance and cross-tolerance to morphine" Eur. J. Pharmacal., 1991. 195(1): p. 37-45.

(56) References Cited

OTHER PUBLICATIONS

Kayser et al. II, "Evidence for a noradrenergic component in the antinociceptive effect of the analgesic agent tramadol in an animal model of clinical pain, the arthritic rat" Eur. J. Pharmacal., 1992. 224(1): p. 83-8.

Collart et al., "Partial inhibition of tramadol antinociceptive effect by naloxone in man" Br. J. Clin. Pharmacal, 1993. 35: p. 73P.

Desmeules et al., "Contribution of monoaminergic modulation to the analgesic effect of tramadol" Br. J. Clin. Pharmacal, 1996. 41(1): p. 7-12).

Raffa et al. II, "Complementary and synergistic antinociceptive interaction between the enantiomers of tramadol" J. Pharmacal. Exp. Ther., 1993. 267(1): p. 331-40).

Rojas-Corrales et al., TramadolInduces Antidepressant-Type Effects in Mice Life Sciences, 1998. vol. 63, No. 12.

Kirchheiner et al., "Effects of the CYP2D6 gene duplication on thepharmacokinetics and pharmacodynamics of tramadol" J. Clin. Psychopharmacol, 2008. 28(1): p. 78-83.

Poulsen et al., "The hypoalgesic effect of tramadol in relation to CYP2D6" Clin. Pharmacal. Ther., 1996. 60(6): p. 636-44.

Stamer et al. I, "Impact of CYP2D6 genotype on postoperative tramadol analgesia" Pain, 2003. 105(1-2): p. 231-8.

Wang et al., "Effect of the CYP2D6*10 C188T polymorphism on postoperative tramadol analgesia in a Chinese population" Eur. J. Clin. Pharmacal., 2006. 62(11): p. 927-31.

Stamer et al. II, "Concentrations of tramadol and 0-desmethyltramadol enantiomers in different CYP2D6 genotypes" Clin. Pharmacal. Ther., 2007. 82(1): p. 41-7.

Potschka et al., "Anticonvulsant and proconvulsant effects of tramadol, its enantiomers and its M1 metabolite in the rat kindling model of epilepsy" Br. J. Pharmacal., 2000.131(2): p. 203-12.

Garrido et al., "Modeling of the in vivo antinociceptive interaction between an opioid agonist, (+)-0-desmethyltramadol, and a monoamine reuptake inhibitor, (−)-0-desmethyltramadol, in rats" J. Pharmacal. Exp. Ther., 2000. 295(1): p. 352-9.

Kukanich and Papich, "Pharmacokinetics of tramadol and the metabolite 0-desmethyltramadol in dogs" J. Vet. Pharmacal. Ther., 2004. 27(4): p. 239-46.

Lehtonen et al.; "Glucuronidation of Racemic O-Desmethyltramadol, the Active Metabolite of Tramadol"; European Journal of Pharm. Sciences; 2010; vol. 41; p. 523-530.

Higuchi; "Mechanism of Sustained Action Medication: Theoretical Analysis of Rate of Release of Solid Drugs Dispersed in Solid Matrices"; Journal of Pharmaceutical Sciences; 1963; vol. 52; p. 1145-1149.

"Dibasic Calcium Phosphate"; http://www.sigmaaldrich.com/catalog/product/sial/c8606?lang=en&region=US; Sigma-Aldrich Co. LLC; 2017; accessed Jun. 15, 2017; 5 pages.

\* cited by examiner

METHODS FOR OVERCOMING RESISTANCE TO TRAMADOL

CROSS-REFERENCE TO RELATED APPLICATION

This application is a continuation application of U.S. patent application Ser. No. 14/821,506 filed on Aug. 7, 2015, which is a divisional application of U.S. patent application Ser. No. 13/543,883 filed on Jul. 8, 2012, which claims priority to U.S. provisional patent application No. 61/506,092 filed on Jul. 9, 2011, the entire contents of which are incorporated herein by reference.

GOVERNMENT RIGHTS

This invention was made with government support under Grant Number DA027304 awarded by the National Institute of Health. The government has certain rights in the invention.

TECHNICAL FIELD

This disclosure provides for the uses of oral O-desmethyltramadol formulations for overcoming resistance to tramadol in selected patients.

BACKGROUND

A genus of phenol ethers are known as having analgesic properties, including (1R,2R or 1S,2S)-2-((dimethylamino)methyl)-1-(3-methoxyphenyl)-cyclohexanol), which has been given the generic name "tramadol." Tramadol (marketed as the HCl salt) is a synthetic atypical, centrally-acting opioid analgesic used for treating moderate to severe pain with efficacy and potency ranging between weak opioids and highly potent opioids such as morphine.

Tramadol was developed by the German pharmaceutical company Grunenthal GmbH in the late 1970s under the trade name Tramal®. One of the advantages of tramadol over traditional opioids is its lower risk of opioid dependence, resulting in it having an unscheduled status in the U.S. and other countries.

Tramadol is a racemate consisting of 1R,2R-tramadol [(+)-tramadol], and 1S,2S-tramadol [(−)-tramadol]. After oral administration of the racemate, both the (−) and (+) forms of both tramadol and the M1 metabolite (i.e., both the 1R,2R-isomer and 1S,2S-isomer of O-desmethyltramadol) are detected in the circulation.

At least two synergistic mechanisms appear operative in providing analgesic activity: binding to .mu.-opioid receptors and inhibition of reuptake of norepinephrine and serotonin. The monoaminergic activity of the parent makes a significant contribution to analgesia by blocking nociceptive impulses at the spinal level.

Consistent with non-opioid mechanisms of analgesia, tramadol induced analgesia is only partially antagonized by the opiate antagonist naloxone in animals and humans. Likewise, in a double-blind, placebo-controlled, crossover study in volunteers, tramadol analgesia was reduced by more than half by an adrenergic receptor antagonist, consistent with tramadol's non-opioid analgesic mechanism involving inhibition of neuronal uptake of norepinephrine.

This dual and synergistic mechanism of action is further attributed to complementary and interactive, mechanisms of action of each tramadol enantiomer. The (+)-enantiomer of tramadol exhibits a 10-fold higher analgesic activity due to a greater affinity for the .mu.-receptor and is a more effective inhibitor of serotonin reuptake, while the (−)-enantiomer is a more effective inhibitor of noradrenalin reuptake and increases noradrenaline release by auto receptor activation.

In addition to treating pain, tramadol and O-desmethyltramadol are said to be effective for treating premature ejaculation (U.S. Pat. No. 6,974,839) and urinary incontinence (U.S. Pat. No. 6,660,774), and each as their single (−) enantiomer are said to be effective for the prevention or treatment of nausea and vomiting (U.S. Pat. No. 6,297,286). Tramadol itself is said to be effective for treating coughs, inflammatory and allergic reactions, depression, obsessive-compulsive spectrum disorders, drug and/or alcohol abuse, gastritis, diarrhea, cardiovascular disease, respiratory disease, mental illness and/or epilepsy (U.S. Pat. Nos. 6,387,956 and 6,723,343 and Rojas-Corrales et al., "Tramadol Induces Antidepressant-Type Effects In Mice" Life Sciences, 1998. vol. 63, No. 12).

Resistance to Tramadol Analgesia

Tramadol is rapidly and extensively metabolized in the liver. The principal metabolic pathways involve cytochrome P-450 isoenzymes 2D6 and 2B6 (O-desmethylation) and 3A4 (N-desmethylation). Importantly, production of both enantiomers of M1 (i.e., 1R,2R-O-desmethyltramadol or '(+)-M1', and 1S,2S-O-desmethyltramadol or '(−)-M1') is dependent on the polymorphic isoenzyme of the debrisoquine-type, cytochrome P450 2D6 (CYP2D6). Approximately 10% of Caucasians have a genotype resulting in reduced activity of CYP2D6. These individuals are poor metabolizers (PM) of tramadol, and they exhibit resistance to tramadol analgesia and diminished or absent M1 in their blood.

Several human clinical studies have shown that tramadol efficacy is significantly decreased or lacking in PM patients. In the first study, using two parallel, randomized, double-blind, placebo-controlled crossover designs, the analgesic effect of tramadol was assessed in 27 volunteers (fifteen extensive metabolizers 'EMs' and twelve PMs) using several experimental pain models (Poulsen et al., "The hypoalgesic effect of tramadol in relation to CYP2D6" Clin. Pharmacol. Ther., 1996. 60(6): p. 636-44). Differences existed between EMs and PMs that indicated M1 was critical for a portion of the analgesic effect of tramadol.

In the second study, the effect of CYP450-2D6 polymorphism on tramadol analgesia was assessed in 300 Caucasian patients undergoing major abdominal surgery (Stamer et al., "Impact of CYP2D6 genotype on postoperative tramadol analgesia" Pain, 2003. 105(1-2): p. 231-8). Patients who had one or more functional alleles were classified as EMs. Genotyping revealed that 35 patients were PMs. Compared to the EMs, the PMs displayed a significantly higher incidence of non-response (P=0.005) and required more tramadol or rescue medication (P=0.02).

In the third study, the effect of CYP450-2D6 polymorphism (specifically CYP450-2D6*10, a SNP (single nucleotide polymorphism) that results in a Pro34 to Ser substitution and reduced CYP450-2D6 metabolic activity) on tramadol-induced analgesia (administered via PCA) was assessed in 63 Chinese patients who underwent gastrectomy for gastric cancer (Wang et al., "Effect of the CYP2D6*10 C188T polymorphism on postoperative tramadol analgesia in a Chinese population" Eur. J. Clin. Pharmacol., 2006. 62(11): p. 927-31). The patients were classified as EMs (N=17) or either heterozygous (N=26) or homozygous (n=20) for CYP2D6*10. Compared to the other groups, the homozygous group required more tramadol (P<0.05).

Finally, a fourth study of patients (N=187) undergoing major abdominal surgery reported a 4-fold greater non-response rate to tramadol in CYP450-2D6 poor metabolizers (Stamer et al., "Concentrations of tramadol and O-desmethyltramadol enantiomers in different CYP2D6 genotypes" Clin. Pharmacol. Ther., 2007. 82(1): p. 41-7). In summary, for mild to moderate pain, both opioid and non-opioid components of tramadol contribute to analgesia. The analgesic effect of tramadol is decreased or absent in patients who have low CYP450-2D6 enzymatic activity (CYP450-2D6, 'poor metabolizers' or PMs) because their M1 serum concentration is considerably less than that in other genotypes.

Sensitivity to the Adverse Events of Tramadol

Approximately 2% of northern white European, and 7% of southern Europeans carry the CYP2D6 gene duplication (more than two functional alleles) that results in ultra-rapid metabolism of tramadol, and these ultra-rapid metabolizers (UMs) are more sensitive to the adverse events of tramadol than other genotypes (Kirchheiner et al., "Effects of the CYP2D6 gene duplication on the pharmacokinetics and pharmacodynamics of tramadol" J. Clin. Psychopharmacol., 2008. 28(1): p. 78-83). In particular, the pharmacokinetics and effects were monitored after a single dose of 100 mg racemic tramadol in 11 UMs and 11 EMs (i.e., two active alleles). Almost 50% of the UM group experienced nausea compared with only 9% of the EM group.

M1 Metabolite (O-Desmethyltramadol)

Potschka et al. dosed female Wistar rats (intraperitoneal) with the (+)-M1 enantiomer followed by observation for adverse effects (Potschka et al., "Anticonvulsant and proconvulsant effects of tramadol, its enantiomers and its M1 metabolite in the rat kindling model of epilepsy" Br. J. Pharmacol., 2000. 131(2): p. 203-12). Garrido et al. dosed male Sprague-Dawley rats i.v. (intravenous) with the (+)-M1 enantiomer alone, or (+)-M1 together with the (−)-M1 enantiomer (Garrido et al., "Modeling of the in vivo antinociceptive interaction between an opioid agonist, (+)-O-desmethyltramadol, and a monoamine reuptake inhibitor, (−)-O-desmethyltramadol, in rats" J. Pharmacol. Exp. Ther., 2000. 295(1): p. 352-9). KuKanich and Papich administered i.v. racemic M1 to beagle dogs (KuKanich and Papich, "Pharmacokinetics of tramadol and the metabolite O-desmethyltramadol in dogs" J. Vet. Pharmacol. Ther., 2004. 27(4): p. 239-46).

SUMMARY

This disclosure provides a pharmaceutical composition comprising the M1 metabolite of tramadol (i.e., O-desmethyltramadol) in an oral pharmaceutical formulation. The present disclosure is based upon the finding that resistance to tramadol analgesia in subjects with reduced activity of CYP2D6 (i.e., poor metabolizers or 'PMs') is overcome by administering M1 and tramadol together, a synergistic combination of agents for relieving a disorder modulated by opiate receptor activity and/or monoamine activity, and in particular for relieving acute, chronic and neuropathic pain. Without being bound by theory, the present disclosure is based upon the hypothesis that tramadol resistance in PMs is overcome when M1 and tramadol are administered together as a result of supplementing these patients with the M1 metabolite that PM patients are incapable of adequately generating on their own. By providing both the M1 metabolite and tramadol, the entire spectrum of synergistic opioid and monoaminergic activity is restored in subjects with the PM phenotype. Advantageously, analgesia is also obtained when M1 and tramadol are administered together in subjects with genotypes not resistant to tramadol, and with fewer adverse events in subjects with the UM phenotype.

This disclosure is also based upon the discovery that achieving optimal synergy between tramadol and M1 in any subject is preferably accomplished with the M1 in a sustained release form, and the tramadol in an immediate-release or sustained release form. Without being bound by theory, in order to be effective in the treatment of a disorder modulated by opiate receptor activity and/or monoamine activity, and in particular for relieving acute, chronic and neuropathic pain, it is necessary that sufficient amounts of both M1 and tramadol are present, in particular in the concentrations and concentration ratios required to produce this surprising synergistic effect.

These concentrations and concentration ratios are reflected in the blood plasma levels of both these active ingredients. Maintaining said blood plasma levels within a range of particular concentration ratios is therefore a desirable goal. It has been unexpectedly discovered however, that this goal is exceedingly challenging because of the very different half-life of circulating M1 due to oral tramadol administration (i.e., M1 arising from tramadol metabolism) compared to the half-life of circulating M1 due to the direct oral administration of M1 in an immediate-release form. Indeed, the clearance of M1 from the plasma due to oral tramadol administration is relatively slow, while the clearance of M1 due to oral dosing of M1 is relatively fast. Thus, without special measures, the blood M1 plasma level after administering M1 and tramadol together, either as a single-dose are as dose cycles, will be insufficient to be effective with plasma tramadol levels, and the synergistic effect no longer present.

Thus, aspect of this disclosure provides a pharmaceutical composition for oral administration of O-desmethyltramadol. Preferably, O-desmethyltramadol is the 1R,2R-isomer or '(+)-M1', the 1S,2S-isomer or '(−)-M1', or a racemic mixture of both isomers or '(+/−)-M1'. Preferably, the pharmaceutical composition is a tablet or capsule for oral administration. More preferably, the pharmaceutical composition comprises a sustained release delivery system of O-desmethyltramadol. Preferably, the amount of O-desmethyltramadol in the pharmaceutical composition is from 5 mg to 100 mg. Preferably, the pharmaceutical composition further comprises tramadol in an amount from 5 mg to 200 mg. In preferred embodiments the M1 salt is M1 HCl.

The present disclosure further provides a pharmaceutical composition comprising O-desmethyltramadol and tramadol, or a pharmaceutically acceptable salt thereof, wherein the O-desmethyltramadol and tramadol concentrations are in a ratio of 95:5 to 5:95 by weight O-desmethyltramadol to tramadol, and more preferably 80:20 to 20:80, 75:25 to 45:55, and in particular 20:2.5, 20:5.0, 20:7.5, 20:10, 20:12.5, 20:15, 20:17.5, 20:20, 20:22.5 and 20:25.

In embodiments involving an oral dosage form of O-desmethyltramadol (M1) and tramadol, M1 is preferably provided in a sustained release dosage form and tramadol is provided as an immediate release dosage form (e.g., each within discrete granules encompassed within the same capsule, wherein the M1 granules provide sustained release, or alternatively as a multi-layer tablet, wherein one layer provides sustained released and the other layer provides immediate release). In other preferred embodiments of an oral dosage form, M1 and tramadol are both provided in a sustained release dosage form, wherein each form provides sustained release with the same or different kinetics (e.g., each within sustained release granules encompassed within the same capsule, or alternatively, both within the same monolithic sustained release tablet). The sustained release dosage form thus comprises a substrate and a pharmaceutically effective amount of M1 or tramadol or both, or pharmaceutically acceptable salts thereof, wherein the term 'substrate' refers to any material or combination of materials, or forms thereof, that results in the in vitro release (i.e., dissolution) pattern specified below for M1 or tramadol or both.

In further embodiments the said substrate is a suitable matrix material in which M1 or its salt form is incorporated, said matrix material preferably comprising polyvinyl acetate and polyvinylpyrrolidone and mixtures thereof, or alternatively, a hydrophilic swellable polymer such as hydroxypropylmethyl cellulose and a salt (i.e., an 'electrolyte').

In a further aspect, the present pharmaceutical preparations comprise two or more phases. In certain embodiments, the respective major parts of M1 or its salt form, and of tramadol, are in different phases of the pharmaceutical preparations. In these embodiments at least one phase may contain either the major part of tramadol or the major part of M1 or a salt-form thereof. In particular embodiments, one phase contains the major part of M1 or a salt thereof and another phase contains the major part of tramadol. Further particular embodiments are pharmaceutical preparations that take the form of a biphasic tablet having a phase that comprises the major part of tramadol and another phase that comprises the major part of M1 or a salt form thereof. The phases in these embodiments may take the form of layers.

In a specific aspect, an embodiment concerns pharmaceutical preparations, as described herein, comprising two or more phases, wherein M1 or its salt form and tramadol are in different phases of the pharmaceutical preparations. In particular embodiments, one phase contains the M1 or a salt thereof and another phase contains the tramadol. Further particular embodiments are pharmaceutical preparations that take the form of a biphasic tablet having a first phase that comprises the tramadol active ingredient and a second phase that comprises the M1 active ingredient or a salt form thereof.

In a particular aspect the present disclosure provides pharmaceutical preparations as defined herein, wherein said preparations are bi- or multi-layer tablets and wherein tramadol and M1, or a salt-form thereof, are localized exclusively to a layer. In particular embodiments, the previously mentioned pharmaceutical preparations take the form of a bilayer tablet having a first phase that comprises the tramadol active ingredient and a second phase that comprises the M1 active ingredient or a salt form thereof.

In a further aspect, there is provided a bi- or multiphasic tablet containing an effective amount of tramadol having at least one phase or layer that contains from about 20% to about 100%, in particular from about 30% to about 90% or from about 50% to 80% of polymeric matrix material.

In a particular embodiment, the tablets are coated with an appropriate coating. The coating may be for taste masking or for other purposes.

There is also provided pharmaceutical preparations, as defined herein, that are capsules or sachets. The tramadol and/or the M1 containing phase or phases in these embodiments may take the form of pellets.

There is further provided a process for manufacturing the oral pharmaceutical preparation described herein, comprising mixing M1 HCl, being incorporated in a suitable sustained release substrate, and tramadol, preferably formulated in a suitable solid carrier form.

There is further provided a process for manufacturing a bi- or multiphasic tablet, comprising compressing two or more pre-shaped phases in an appropriate compressing apparatus.

In a further aspect there is provided a process for manufacturing a bi- or multilayer tablet comprising compressing a suitable tramadol containing composition as to form a layer, laying M1 containing matrix material on this tramadol containing layer, compressing the whole, and if desired laying further compositions of tramadol and/or further M1 containing matrix material thereon and each time subjecting the whole to a compression and if further desired coating the thus prepared dosage form.

In a further aspect there is provided a process for manufacturing a bi- or multilayer tablet in accordance with the disclosure comprising compressing M1 containing matrix material as to form a layer, laying a suitable tramadol containing mixture on this M1 containing matrix material layer, compressing the whole, and if desired laying further compositions of tramadol and/or further M1 matrix material thereon and each time subjecting the whole to a compression and if further desired coating the thus prepared dosage form.

The present disclosure further provides a method for treating disorders modulated by at least opiate receptor activity or monoamine activity comprising orally administering to a mammal in need thereof a therapeutically effective amount of O-desmethyltramadol, or a pharmaceutically acceptable salt thereof. The present disclosure further provides a method for relieving acute and chronic pain, comprising orally administering to a mammal in need thereof a therapeutically effective amount of O-desmethyltramadol, or a pharmaceutically acceptable salt thereof. Preferably, the method further comprises orally administering tramadol, or a pharmaceutically acceptable salt thereof. Preferably, the amount of O-desmethyltramadol is 5 mg to 100 mg and the amount of tramadol is 5 mg to 200 mg. More preferably, the amount of O-desmethyltramadol, or a pharmaceutically acceptable salt thereof is 10 mg to 40 mg and the amount of tramadol, or a pharmaceutically acceptable salt thereof is 10 mg to 40 mg.

Figure 4:
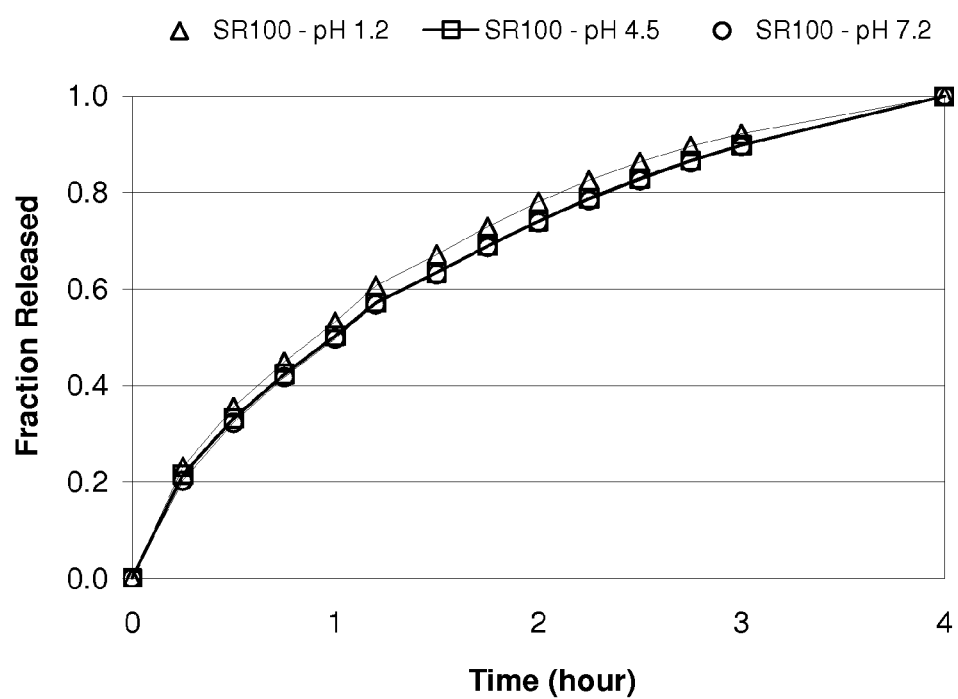

FIG. 4 shows a graphical representation of dissolution kinetics of sustained release formulation SR100 as a function of pH.

Figure 5A:
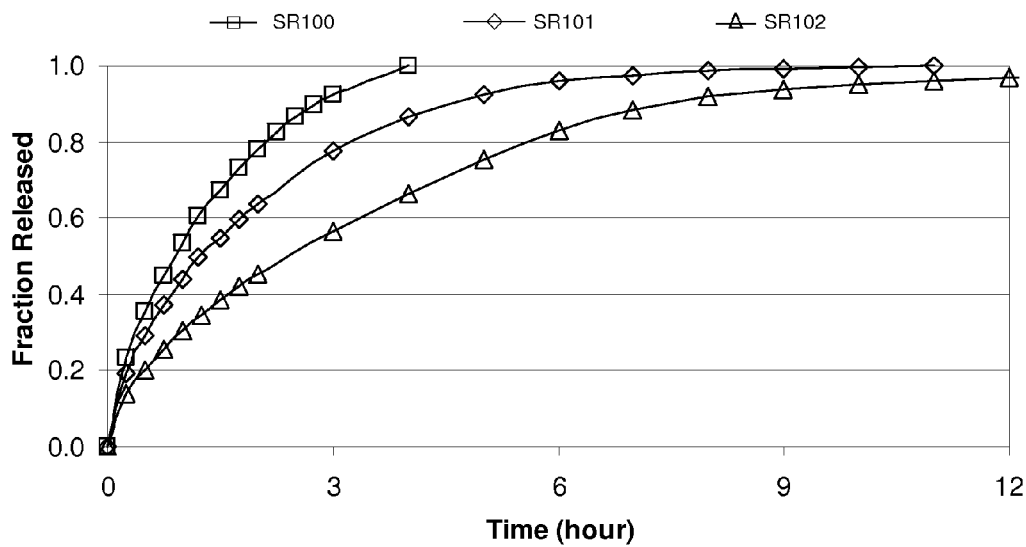

FIG. 5A shows a graphical representation of dissolution data of sustained release formulations SR100, SR101 and SR102.

Figure 5B:
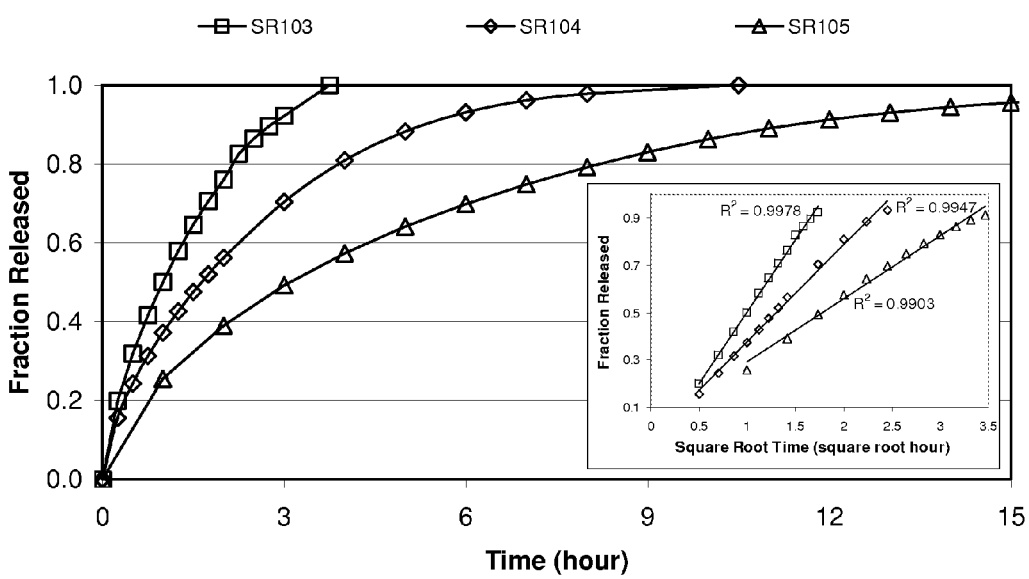

FIG. 5B shows dissolution data of sustained release formulations SR103, SR104 and SR105 with a t chart provided as the inset.

Figure 6A:
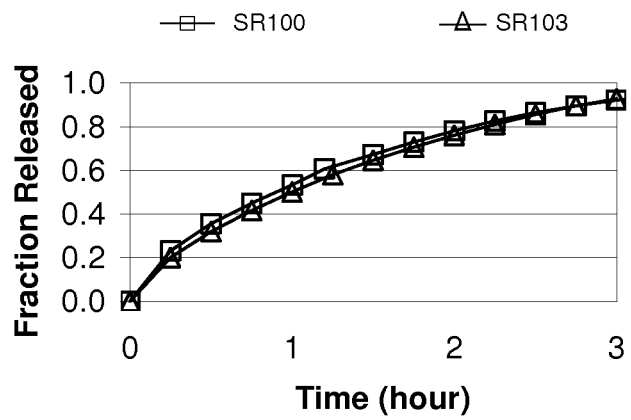

FIG. 6A shows a graphical representation of the dissolution data of SR100, SR101 and SR102 (20 mg M1 HCl strength series) overplayed with the dissolution data of SR103 (40 mg M1 HCl strength series).

Figure 6B:
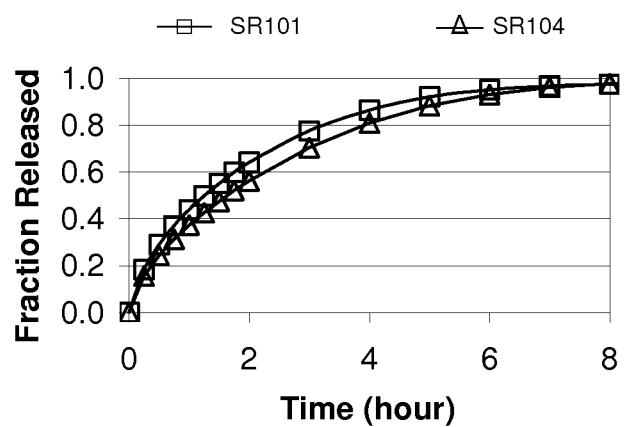

FIG. 6B shows a graphical representation of the dissolution data of SR100, SR101 and SR102 (20 mg M1 HCl strength series) overplayed with the dissolution data of SR104 (40 mg M1 HCl strength series).

Figure 6C:
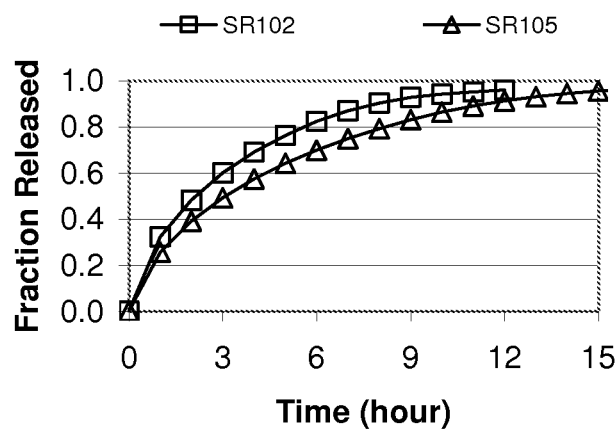

FIG. 6C shows a graphical representation of the dissolution data of SR100, SR101 and SR102 (20 mg M1 HCl strength series) overplayed with the dissolution data of SR105 (40 mg M1 HCl strength series).

Figure 7:
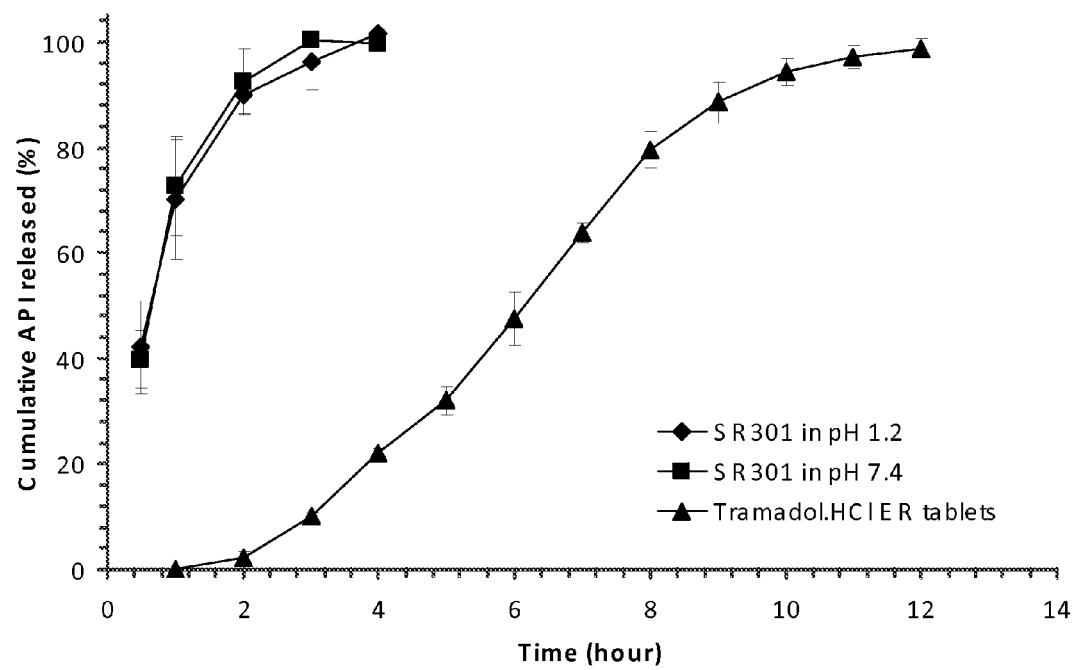

FIG. 7 shows a graphical representation of the dissolution data of sustained release formulation SR301 in media at pH 1.2 and 7.4 and the tramadol HCl extended release (Ultram ER®) control in a medium with pH 7.4.

Figure 8:
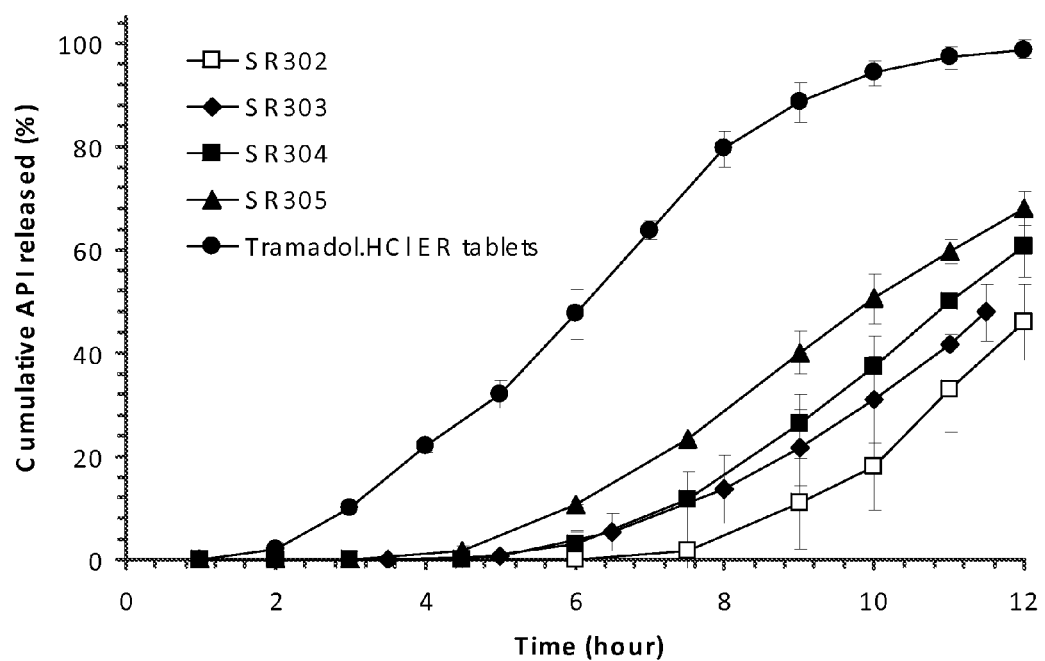

FIG. 8 shows a graphical representation of the dissolution data of sustained release formulation SR302, SR303, SR304 and SR305. Also represented is the dissolution data of the tramadol HCl extended release (Ultram ER®) control.

Figure 9:
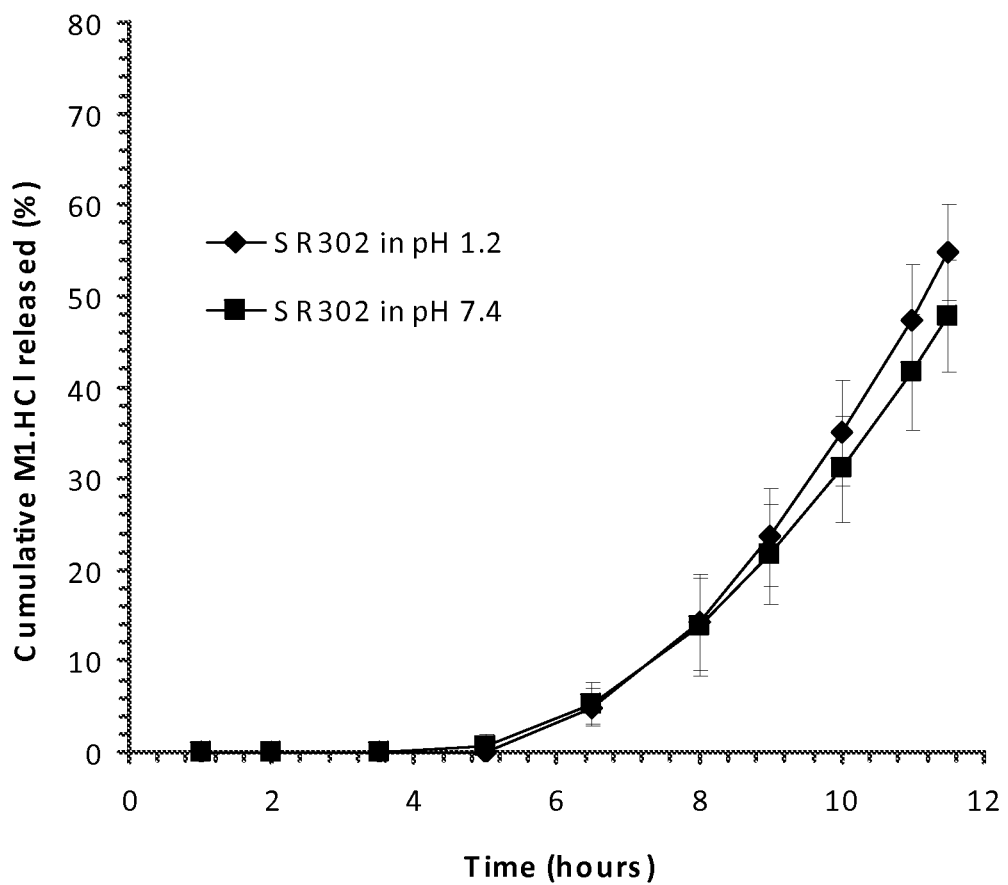

FIG. 9 shows a graphical representation of the dissolution data of sustained release formulation SR302 in media at pH 1.2 and 7.4.

Figure 10:
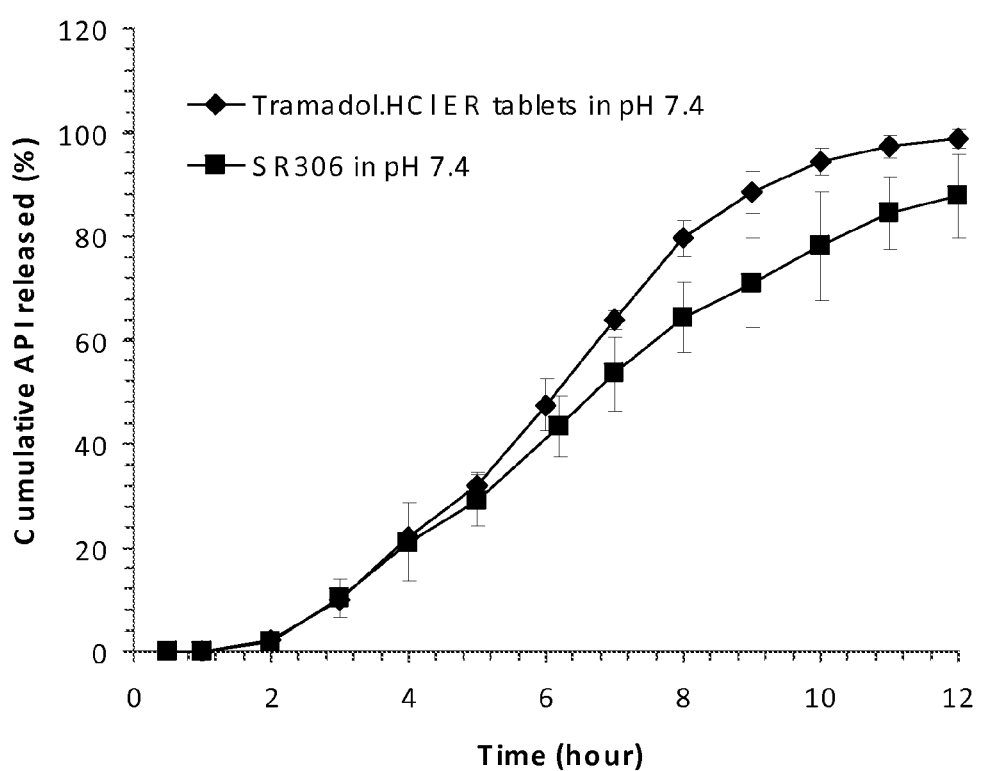

FIG. 10 shows a graphical representation of the dissolution data of sustained release formulation SR306 and the tramadol HCl extended release (Ultram ER®) control in a medium with pH 7.4.

Figure 11:
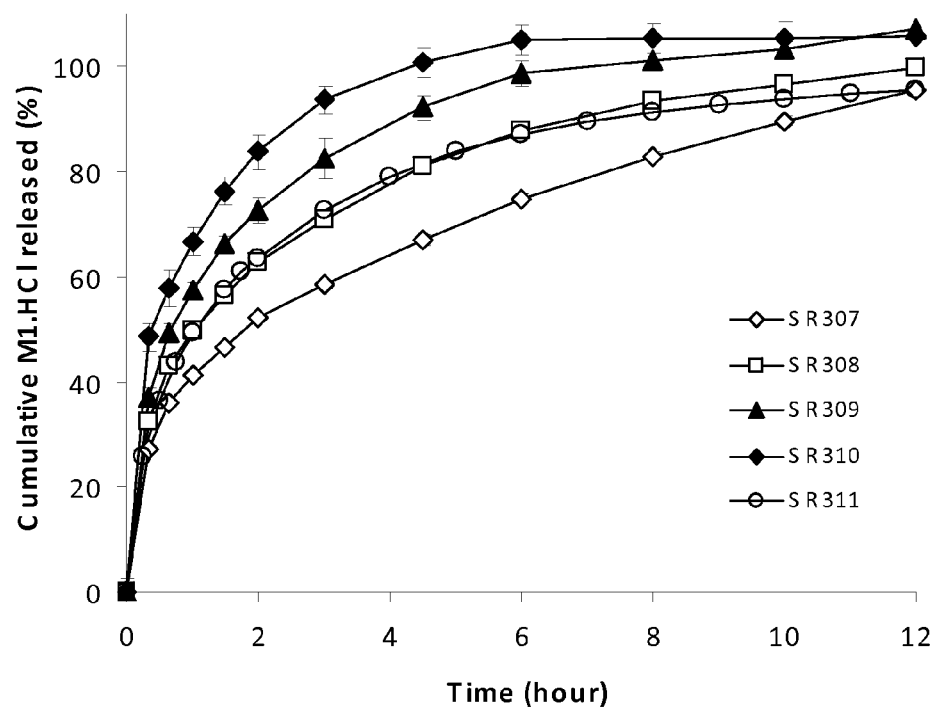

FIG. 11 shows a graphical representation shows a graphical representation of the dissolution data of sustained release formulation SR307, SR308, SR309, SR310 and SR311.

Figure 12:
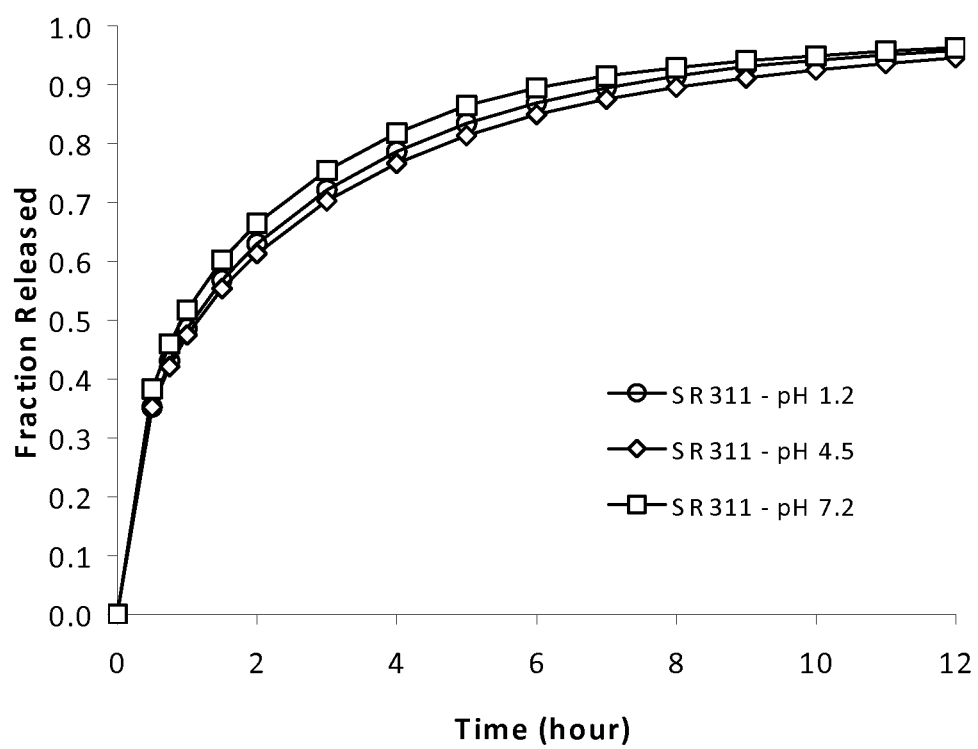

FIG. 12 shows a graphical representation of dissolution kinetics of sustained release formulation SR311 as a function of pH.

Figure 13A:
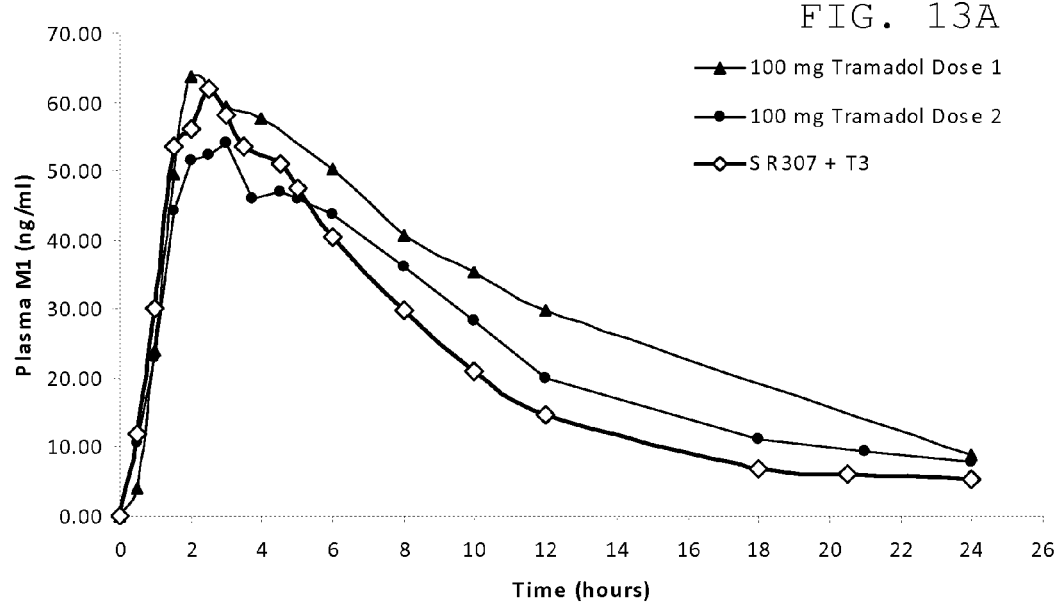

FIG. 13A shows a graphical representation of plasma O-desmethyltramadol (M1) concentrations in a subject after a single oral dose of SR M1+IR tramadol combination form SR307+T$_3$ wherein SR307 is the SR M1 form with 40 mg M1 HCl, and T$_3$ is 30 mg of racemic tramadol IR (proportional fraction of a 50 mg Ultram® tablet). The same control data for two single-dosings of 100 mg IR tramadol HCl (two 50 mg Ultram® tablets) are shown for comparison purposes.

Figure 13B:
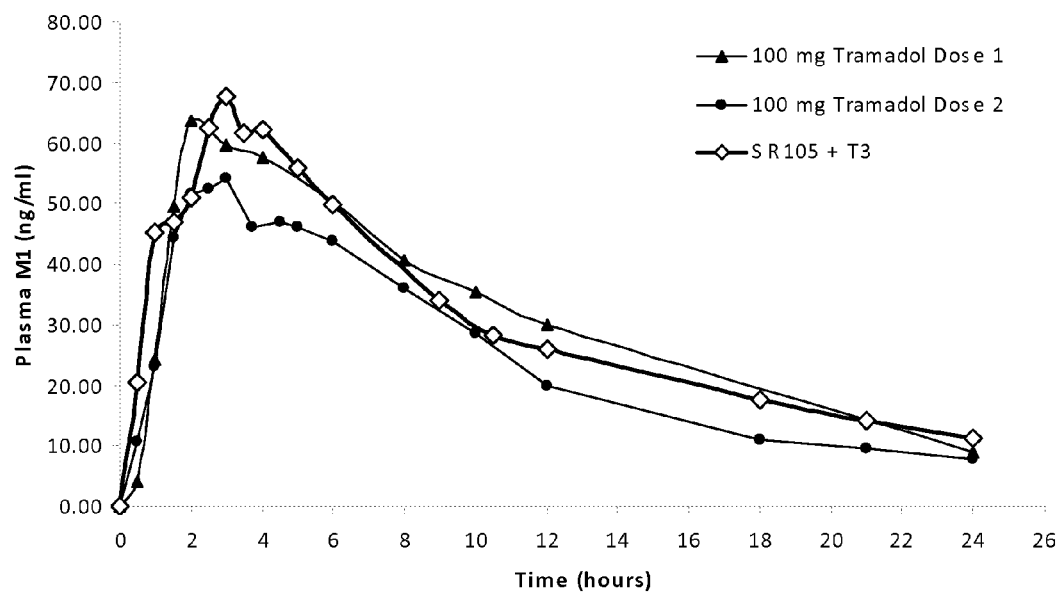

FIG. 13B shows a graphical representation of plasma O-desmethyltramadol (M1) concentrations in a subject after a single oral dose of SR M1+IR tramadol combination SR105+T$_3$, wherein SR105 is the SR M1 form with 40 mg M1 HCl, and T$_3$ is 30 mg of racemic tramadol IR (proportional fraction of a 50 mg Ultram® tablet). The same control data for two single-dosings of 100 mg IR tramadol HCl (two 50 mg Ultram® tablets) are shown for comparison purposes.

Figure 14:
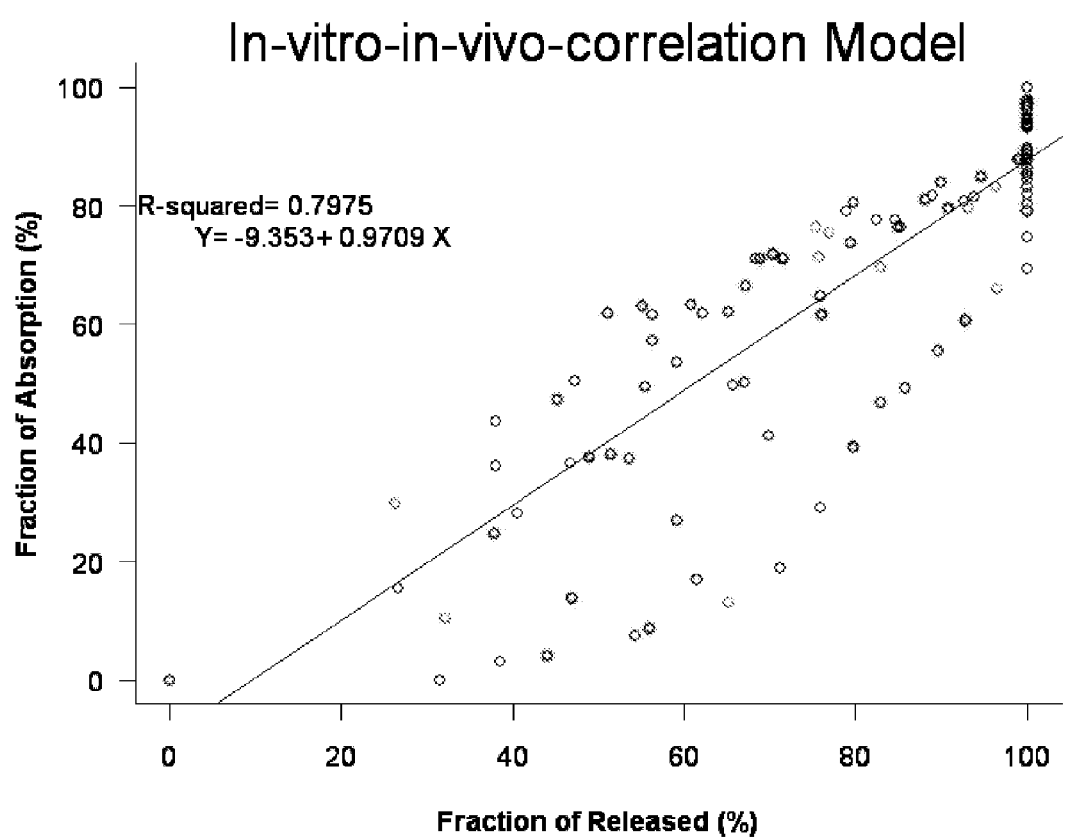

FIG. 14 shows a graphical representation of the fraction absorbed as a function of the fraction released according to the IVIVC model developed herein for sustained release formulations SR103, SR104, SR105, SR203, SR206, SR307, SR308 and SR310.

Figure 15A:
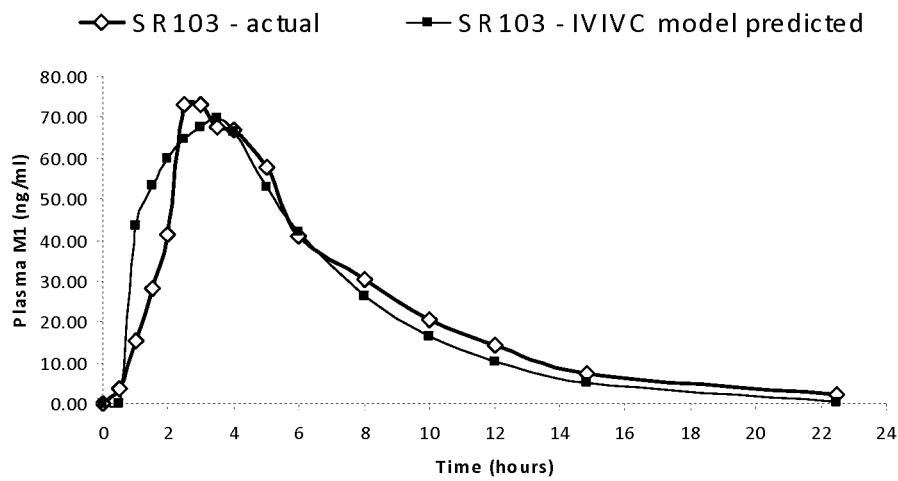

FIG. 15A shows a graphical representation of the actual versus IVIVC-model-predicted M1 plasma concentration profiles for a single-dose of SR103 (monolithic CDT® series).

Figure 15B:
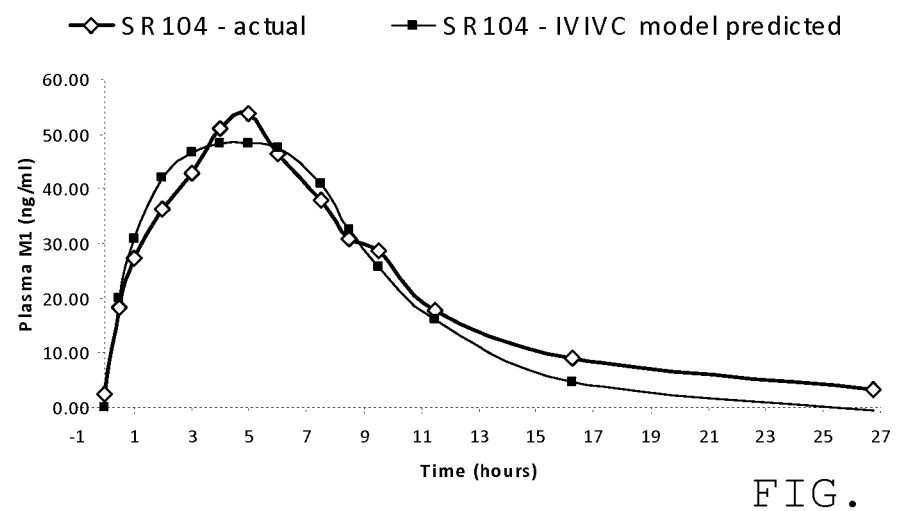

FIG. 15B shows a graphical representation of the actual versus IVIVC-model-predicted M1 plasma concentration profiles for a single-dose of SR104 (monolithic CDT® series).

Figure 15C:
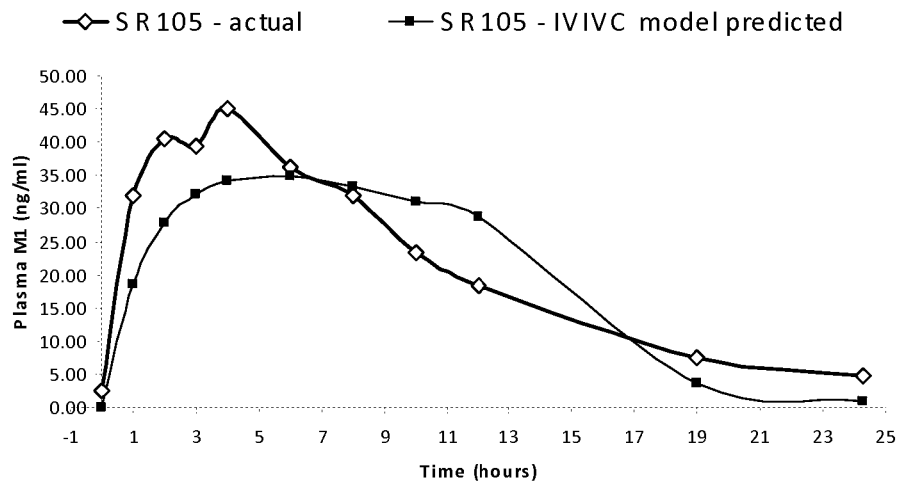

FIG. 15C shows a graphical representation of the actual versus IVIVC-model-predicted M1 plasma concentration profiles for a single-dose of SR105 (monolithic CDT® series).

Figure 16A:
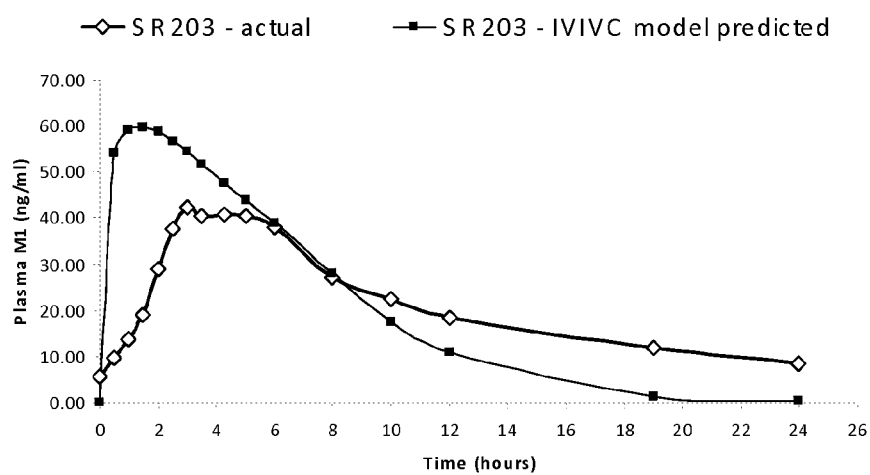

FIG. 16A shows a graphical representation of the actual versus IVIVC-model-predicted M1 plasma concentration profiles for a single-dose of SR203 (monolithic HPMC series).

Figure 16B:
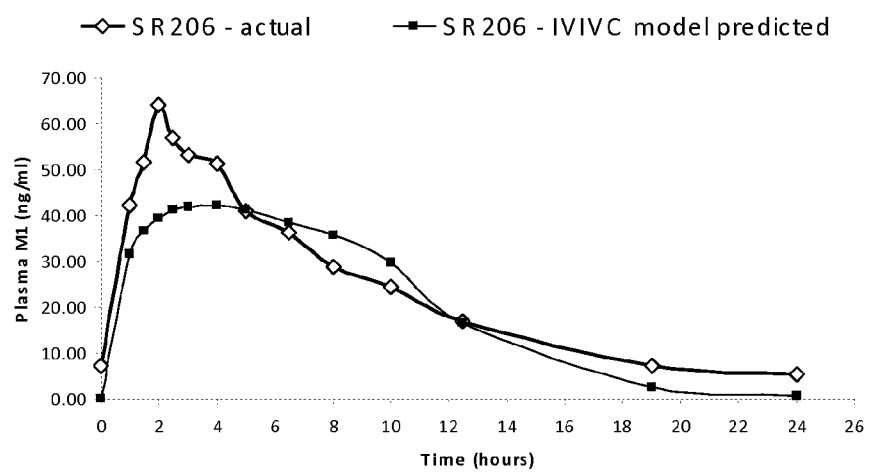

FIG. 16B shows a graphical representation of the actual versus IVIVC-model-predicted M1 plasma concentration profiles for a single-dose of SR206 (monolithic HPMC series).

Figure 17A:
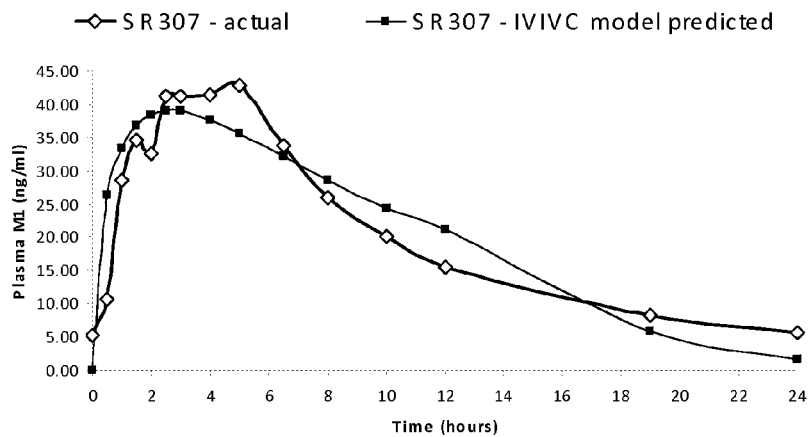

FIG. 17A shows a graphical representation of the actual versus IVIVC-model-predicted M1 plasma concentration profiles for a single-dose of SR307 (monolithic Kollidon® SR series).

Figure 17B:
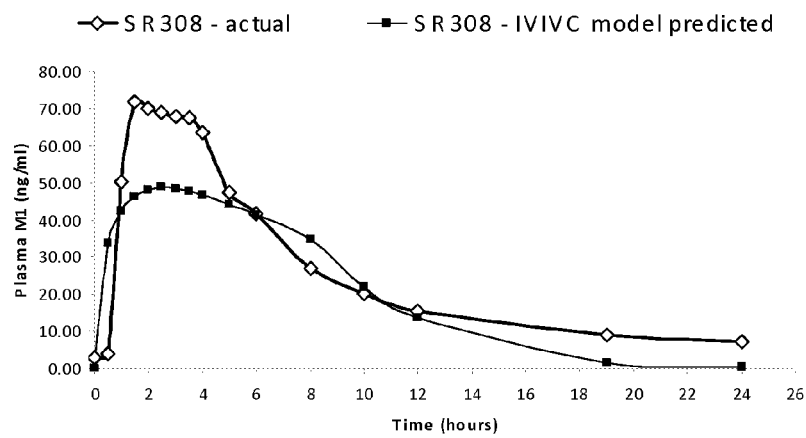

FIG. 17B shows a graphical representation of the actual versus IVIVC-model-predicted M1 plasma concentration profiles for a single-dose of SR308 (monolithic Kollidon® SR series).

Figure 17C:
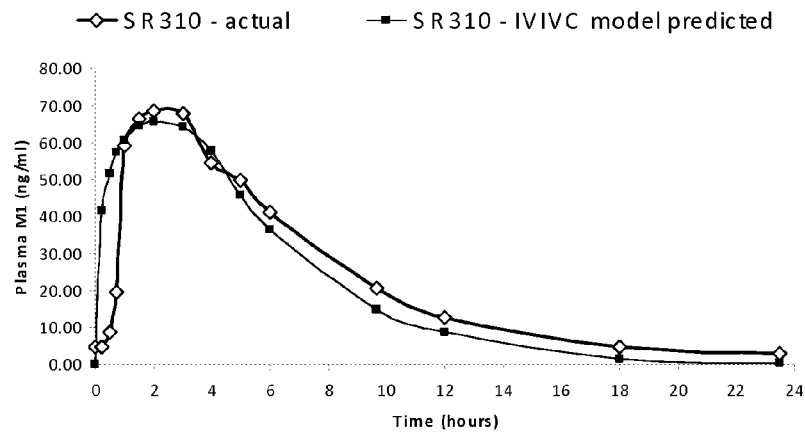

FIG. 17C shows a graphical representation of the actual versus IVIVC-model-predicted M1 plasma concentration profiles for a single-dose of SR310 (monolithic Kollidon® SR series).

Figure 18:
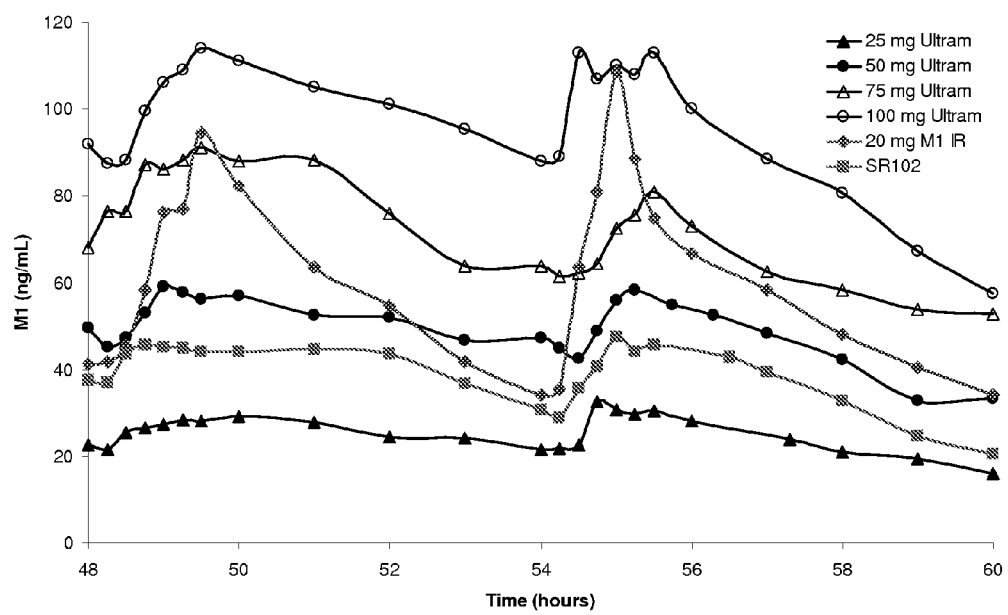

FIG. 18 shows a graphical representation of the plasma O-desmethyltramadol (M1) concentrations in the subject after having received 10 doses of SR102 every 6 hours (9$^{th}$ and 10$^{th}$ doses shown). Also reproduced from FIG. 2B for comparison purposes is the M1 plasma profiles for 20 mg IR O-desmethyltramadol and 25, 50, 75 or 100 mg IR tramadol (Ultram® tablets), all given every 6 hours (9$^{th}$ and 10$^{th}$ doses shown for each).

Figure 19:
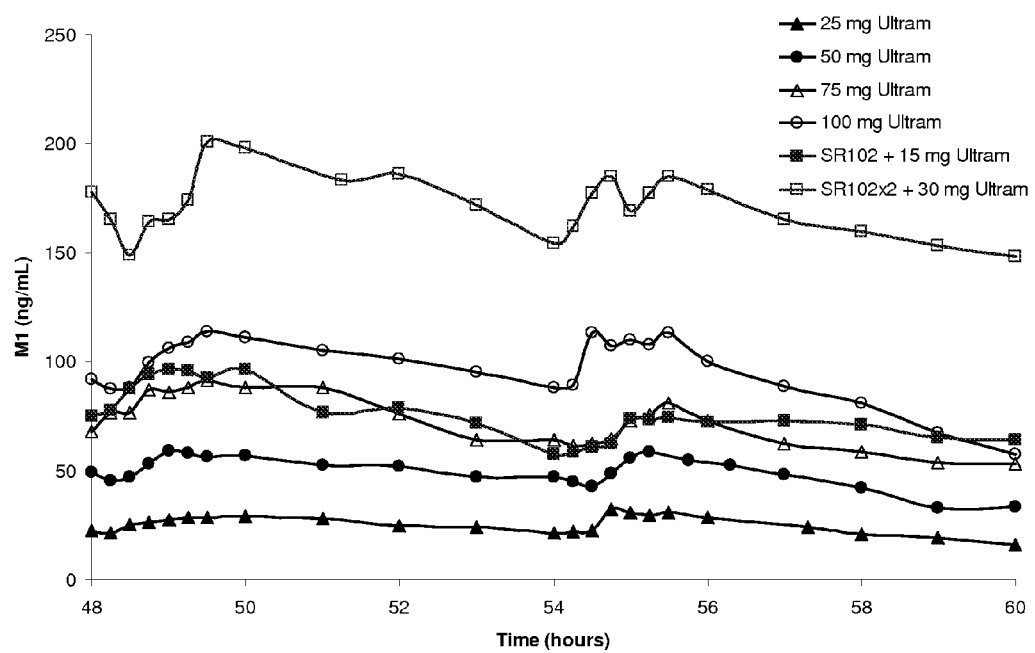

FIG. 19 shows a graphical representation of the plasma O-desmethyltramadol (M1) concentrations in the subject after having received 10 doses every 6 hours (9$^{th}$ and 10$^{th}$ doses shown) of (i) one SR102 tablet plus 15 mg IR tramadol tablet) (Ultram®, or (ii) two SR102 tablets plus 30 mg IR tramadol tablet. Also reproduced from FIG. 2B for comparison purposes is the M1 plasma profiles for 25, 50, 75 or 100 mg IR tramadol (Ultram® tablets), all given every 6 hours (9$^{th}$ and 10$^{th}$ doses shown for each).

Figure 20A:
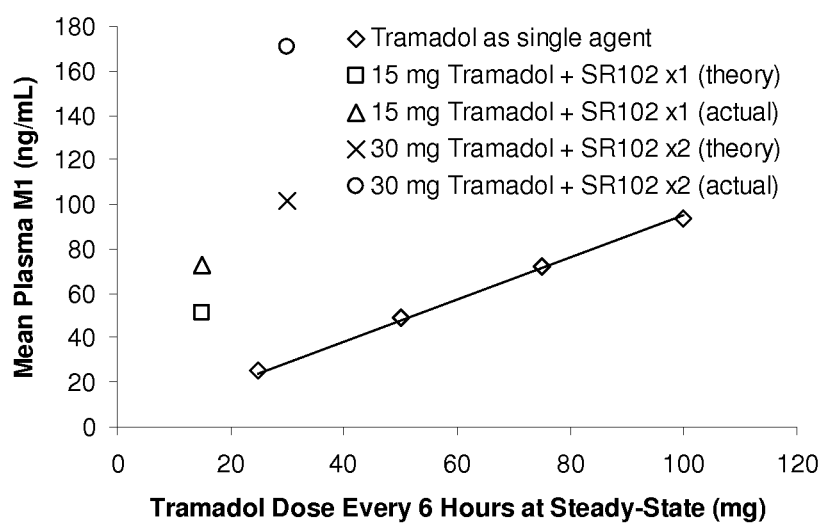

FIG. 20A shows the actual versus predicted average plasma levels for M1 tramadol after SR M1 was given simultaneously with IR tramadol HCl as a combination formulation.

Figure 20B:
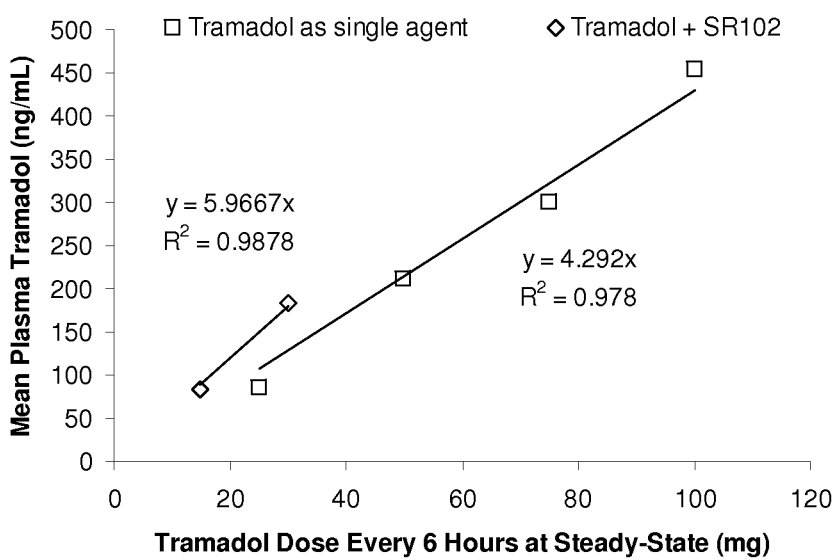

FIG. 20B shows the actual versus predicted average plasma levels for tramadol after SR M1 was given simultaneously with IR tramadol HCl as a combination formulation as in FIG. 20A.

DETAILED DESCRIPTION

This disclosure provides a pharmaceutical composition of the M1 metabolite of tramadol (i.e., O-desmethyltramadol) in an oral formulation. This finding led to the additional discovery that resistance to tramadol analgesia in subjects with reduced activity of CYP2D6 (i.e., poor metabolizers or 'PMs') is overcome by administering M1 and tramadol together, a synergistic combination of agents for relieving a disorder modulated by opiate receptor activity and/or monoamine activity, and in particular for relieving acute, chronic and neuropathic pain. Without being bound by theory, it is believed that tramadol resistance in PMs is overcome when M1 and tramadol are administered together as a result of supplementing these patients with the M1 metabolite that they are incapable of adequately generating on their own. By providing both the M1 metabolite and the parent drug, the two agents are able to act synergistically and the entire spectrum of opioid and monoaminergic activity is restored in subjects with the PM phenotype. Advantageously, analgesia is also obtained when M1 and tramadol are administered together in subjects with genotypes not resistant to tramadol, and with fewer adverse events in subjects with the UM phenotype.

The present disclosure provides tramadol and its primary metabolite, O-desmethyltramadol (M1). Tramadol and O-desmethyltramadol (M1) each exist as the trans conformational isomer, with each conformational isomer existing as a pair of enantiomers because two chiral centers are present in the cyclohexane ring of each compound. Accordingly, tramadol and O-desmethyltramadol each consist of an enantiomeric pair, designated (1R,2R)-tramadol, (1S,2S)-tramadol, (1R,2R)-O-desmethyltramadol, and (1S,2S)-O-desmethyltramadol.

As used herein, the terms 'tramadol', 'O-desmethyltramadol' and 'M1' unless specified otherwise, shall mean the racemic mixture of the 1R,2R-isomer and the 1S,2S-isomer. As used herein, the terms 'tramadol species' or 'O-desmethyltramadol species' shall mean the racemate, the 1R,2R-isomer or 1S,2S-isomer of tramadol or O-desmethyltramadol, respectively.

In preferred embodiments, a combination of O-desmethyltramadol and tramadol is provided. In certain embodiments, the combination comprises O-desmethyltramadol and tramadol in a weight ratio range of 95:5 to 5:95. A weight ratio range of 80:20 to 20:80 is preferred. Other preferred weight ratios of O-desmethyltramadol to tramadol include 90:10, 80:20, 70:30, 60:40, 50:50, 40:60, 30:70, 20:80 and 10:90. For 200 mg of the combination, the above weight ratios provide O-desmethyltramadol and tramadol in amounts of (mg:mg) 180:20, 160:40, 140:60, 120:80, 100:100, 80:120, 60:140, 40:160 and 20:180. For 100 mg of the combination, the above weight ratios provide O-desmethyltramadol and tramadol in amounts of (mg:mg) 90:10, 80:20, 70:30, 60:40, 50:50, 40:60, 30:70, 20:80 and 10:90. For 50 mg of the combination, these weight ratios provide O-desmethyltramadol and tramadol in amounts of (mg:mg) 45:5, 40:10, 35:15, 30:20, 25:25, 20:30, 15:35, 10:40 and 5:45.

Other preferred weight ratios of O-desmethyltramadol to tramadol include 20:7.5, 20:10, 20:12.5, 20:15, 20:17.5, 20:20, 20:22.5 and 20:25. For a combination tablet containing 20 mg O-desmethyltramadol, the above weight ratios provide O-desmethyltramadol and tramadol in amounts of (mg:mg) 20:7.5, 20:10, 20:12.5, 20:15, 20:17.5, 20:20, 20:22.5 and 20:25. For a combination tablet containing 40 mg O-desmethyltramadol, the above weight ratios provide O-desmethyltramadol and tramadol in amounts of (mg:mg) 40:15, 40:20, 40:25, 40:30, 40:35, 40:40, 40:45 and 40:50.

The present disclosure further provides eight additional combinations, including:
(1) racemic O-desmethyltramadol with (1R,2R)-tramadol;
(2) racemic O-desmethyltramadol with (1S,2S)-tramadol;
(3) (1R,2R)-O-desmethyltramadol with racemic tramadol;
(4) (1S,2S)-O-desmethyltramadol with racemic tramadol;
(5) (1R,2R)-O-desmethyltramadol with (1R,2R)-tramadol;
(6) (1R,2R)-O-desmethyltramadol with (1S,2S)-tramadol;
(7) (1S,2S)-O-desmethyltramadol with (1R,2R)-tramadol; and
(8) (1S,2S)-O-desmethyltramadol with (1S,2S)-tramadol.

In these embodiments, the weight ratio range for the racemate to isomer, isomer to racemate, or isomer to isomer is a weight ratio range of 95:5 to 5:95 for O-desmethyltramadol:tramadol species. Preferred weight ratios for O-desmethyltramadol:tramadol species include 90:10, 80:20, 70:30, 60:40, 50:50, 40:60, 30:70, 20:80 and 10:90. For 200 mg of the combination, the above weight ratios provide O-desmethyltramadol and tramadol species in amounts of (mg:mg) 180:20, 160:40, 140:60, 120:80, 100:100, 80:120, 60:140, 40:160 and 20:180. For 100 mg of the combination, the above weight ratios provide O-desmethyltramadol and tramadol species in amounts of (mg:mg) 90:10, 80:20, 70:30, 60:40, 50:50, 40:60, 30:70, 20:80 and 10:90. For 50 mg of the combination, these weight ratios provide O-desmethyltramadol and tramadol species in amounts of (mg:mg) 45:5, 40:10, 35:15, 30:20, 25:25, 20:30, 15:35, 10:40 and 5:45.

O-desmethyltramadol (M1) is useful for treating disorders modulated by opiate receptor activity or monoamine activity, or both opiate receptor activity and monoamine activity. Accordingly, this disclosure provides methods for such treatment. This disclosure provides a method for treating disorders modulated by opiate receptor activity or monoamine activity, or both opiate receptor activity and monoamine activity, comprising administering to a mammal in need thereof a therapeutically effective amount of O-desmethyltramadol, or a pharmaceutically acceptable salt thereof. The O-desmethyltramadol administered may be (1R,2R)-O-desmethyltramadol, (1S,2S)-O-desmethyltramadol, or a racemic mixture thereof. In some embodiments, the amount of O-desmethyltramadol species administered is 5 mg to 200 mg, 5 mg to 100 mg, 5 mg to 50 mg, 5 to 25 mg, and more preferably 20 mg to 50 mg. In other embodiments, the amount of O-desmethyltramadol species administered is 5, 10, 15, 20, 25, 30, 35, 40, 45, 50, 55, 60, 65, 70, 75, 80, 85, 90, 95 or 100 mg. Preferred amounts of O-desmethyltramadol species administered are 20, 25, 30, 35, 40, 45 and 50 mg. Administration is preferably via the oral route.

As used herein, the terms 'mammal', 'subject' or 'patient' are used interchangeably and are intended to have equivalent meanings.

In a preferred embodiment, particularly those involving the treatment of acute and chronic pain, is a method for administrating to a subject O-desmethyltramadol together with tramadol, or a pharmaceutically acceptable salt of both or either. The O-desmethyltramadol administered is, for example, (1R,2R)-O-desmethyltramadol, (1S,2S)-O-desmethyltramadol, or the racemic mixture thereof, and the tramadol administered may be (1R,2R)-tramadol, (1S,2S)-tramadol, or the racemic mixture thereof. Such methods are particularly preferred in subjects who are 'poor metabolizers' of tramadol to O-desmethyltramadol, particularly those with a genotype resulting in reduced activity of CYP2D6. Such methods are also preferred in subjects who are 'ultra-rapid metabolizers' of tramadol to O-desmethyltramadol, particularly those with a genotype resulting in abnormally high activity of CYP2D6. The terms 'poor metabolizers' and 'ultra-rapid metabolizers' of tramadol are defined in the art; see for example Kirchheiner et al. and the references therein (Kirchheiner et al., "Effects of the CYP2D6 gene duplication on the pharmacokinetics and pharmacodynamics of tramadol" J. Clin. Psychopharmacol., 2008. 28(1): p. 78-83). With respect to CYP2D6 genotypes, the human population has generally been subdivided into the following categories: poor metabolizer ('PM', two inactive alleles, ±10% of population), intermediate metabolizer ('IM', one inactive allele, 35% of population), extensive or 'normal' metabolizer ('EM', two active alleles, 50%) and ultra-rapid metabolizer ('UM', gene duplications yielding more than two active alleles, 2% in northern European whites and 7% in southern Europe). The in vivo production in humans of both enantiomers of M1 (i.e., 1R,2R-O-desmethyltramadol or '(+)-M1', and 1S,2S-O-desmethyltramadol or '(−)-M1') from racemic tramadol is dependent on the polymorphic isoenzyme of the debrisoquine-type, cytochrome P450 2D6 (CYP2D6).

Methods for administrating O-desmethyltramadol together with tramadol are provided herein, wherein the amount of O-desmethyltramadol is 5 mg to 100 mg and the amount of tramadol is 5 mg to 200 mg. In preferred embodiments, the amount of O-desmethyltramadol or a pharmaceutically acceptable salt thereof is 10 mg to 50 mg, and the amount of tramadol or a pharmaceutically acceptable salt thereof is 10 mg to 100 mg. Preferably, the O-desmethyltramadol and tramadol are each the racemate, but the isolated isomers are also suitable according to the disclosure.

In methods for administrating O-desmethyltramadol together with tramadol, any weight ratio of O-desmethyltramadol:tramadol species within the range of 95:5 to 5:95 is encompassed by the disclosure. Preferred weight ratios of O-desmethyltramadol:tramadol species include 90:10, 80:20, 70:30, 60:40, 50:50, 40:60, 30:70, 20:80 and 10:90. A weight ratio range of 80:20 to 20:80 is preferred, and more preferably 75:25 to 45:55, and in particular the ratios 20:7.5, 20:10, 20:12.5, 20:15, 20:17.5, 20:20, 20:22.5 and 20:25 are preferable.

For a combined 200 mg weight of O-desmethyltramadol and tramadol species, the above ratios provide O-desmethyltramadol:tramadol species in amounts including but not limited to (mg:mg) 180:20, 160:40, 140:60, 120:80, 100:100, 80:120, 60:140, 40:160 and 20:180. For a combined 100 mg weight of O-desmethyltramadol:tramadol species, the above ratios provide O-desmethyltramadol and tramadol species in amounts including but not limited to (mg:mg) 90:10, 80:20, 70:30, 60:40, 50:50, 40:60, 30:70, 20:80 and 10:90. For a combined 50 mg weight of O-desmethyltramadol and tramadol species, these ratios provide O-desmethyltramadol:tramadol species in amounts including but not limited to (mg:mg) 45:5, 40:10, 35:15, 30:20, 25:25, 20:30, 15:35, 10:40 and 5:45. For a combination tablet containing 20 mg O-desmethyltramadol, the above weight ratios provide O-desmethyltramadol and tramadol in amounts including but not limited to (mg:mg) 20:7.5, 20:10, 20:12.5, 20:15, 20:17.5, 20:20, 20:22.5 and 20:25. For a combination tablet containing 40 mg O-desmethyltramadol, the above weight ratios provide O-desmethyltramadol and tramadol in amounts including but not limited to (mg:mg) 40:15, 40:20, 40:25, 40:30, 40:35, 40:40, 40:45 and 40:50.

As used herein, the term "disorder" modulated by opiate receptor activity and/or monoamine activity refers to a disorder, disease or condition where modulating opiate receptor activity and/or monoamine activity is an effective means of alleviating the disorder or one or more of the biological manifestations of the disease or disorder; or interferes with one or more points in the biological cascade leading to the disorder or responsible for the underlying disorder; or alleviates one or more symptoms of the disorder. Thus, disorders subject to modulation include those for which:

(a) the lack of opiate receptor activity and/or monoamine activity is a cause of the disorder or one or more of the biological manifestations, whether the activity was altered genetically, by infection, by irritation, by internal stimulus or by some other cause;

(b) the disease or disorder or the observable manifestation or manifestations of the disease or disorder are alleviated by opiate receptor activity and/or monoamine activity. The lack of opiate receptor activity and/or monoamine activity need not be causally related to the disease or disorder or the observable manifestations thereof; or (c) opiate receptor activity and/or monoamine activity interferes with part of the biochemical or cellular cascade that results in or relates to the disease or disorder. In this respect, the opiate receptor activity and/or monoamine activity alters the cascade, and thus controls the disease, condition or disorder.

Disorders modulated by opiate receptor activity and/or monoamine activity include acute and chronic pain, neuropathic pain, affective disorders, including depression and anxiety, behavioral disorders, including attention deficit disorders, eating disorders, cerebral function disorders, substance abuse, urinary incontinence and premature ejaculation as those terms are defined in U.S. Pat. Nos. 6,780,891, 6,660,774 and 6,974,839, incorporated by reference herein. The term "neuropathic pain" is applied to any acute or chronic pain syndrome in which the sustaining mechanism for the pain is believed to involve abnormal transmission (peripheral) or processing (central) of somatosensory input.

The present disclosure relates to a method for relieving a disorder modulated by opiate receptor activity and/or monoamine activity. Most preferably, the disorder is acute pain, chronic pain or neuropathic pain. The method comprises orally administering to a mammal in need thereof a therapeutically effective amount of O-desmethyltramadol (M1), or a pharmaceutically acceptable salt thereof. In a preferred embodiment, the method comprises orally administering to a mammal in need thereof a therapeutically effective amount of O-desmethyltramadol (M1) and tramadol, or pharmaceutically acceptable salts thereof.

The present disclosure also provides a pharmaceutical composition containing a therapeutically effective amount of an O-desmethyltramadol species, or a pharmaceutically acceptable salt thereof. A pharmaceutically acceptable carrier may also be included. A pharmaceutical composition adapted for the oral delivery of an O-desmethyltramadol species is particularly preferred. Other therapeutic ingredients may also be included. A preferred therapeutic ingredient is a therapeutically effective amount of a tramadol species, or a pharmaceutically acceptable salt thereof. The pharmaceutical compositions contain O-desmethyltramadol and optional tramadol species, or their pharmaceutically acceptable salts, in amounts and in weight ratios as provided in this disclosure (vide supra).

The term "pharmaceutically acceptable salts" mean salts prepared from pharmaceutically acceptable non-toxic acids including inorganic acids and organic acids. Examples of acids that form pharmaceutically acceptable salts with tramadol and O-desmethyltramadol species include acetic acid, benzenesulfonic (besylate) acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid. The hydrochloric acid salt is particularly preferred.

Any suitable route of administration may be employed for providing the patient with an effective dosage of O-desmethyltramadol and optional tramadol species, or their pharmaceutically acceptable salts. For example, oral, rectal, parenteral (including subcutaneous, intramuscular, and intravenous) routes may be employed. Dosage forms include tablets, troches, dispersions, solutions, capsules and patches. In particular, the composition may be formulated for oral administration, and may be in the form of a tablet or capsule.

Pharmaceutically acceptable carriers for use in the compositions of the present disclosure may take a wide variety of forms, depending on the forms preparation desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Oral syrups, as well as other oral liquid formulations, are well known to those skilled in the art, and general methods for preparing them are found in any standard pharmacy school textbook, for example Remington: The Science and Practice of Pharmacy. Chapter 86 of the $19^{th}$ edition of Remington entitled "Solutions, Emulsions, Suspensions and Extracts" describes in complete detail the preparation of syrups (pages 1503-1505) and other oral liquids. Similarly, sustained (i.e., controlled) release formulations are well known in the art, and Chapter 94 of the same reference, entitled "Sustained-Release Drug Delivery Systems," describes the more common types of oral and parenteral sustained-release dosage forms (pages 1660-1675). The relevant disclosure, Chapters 84 and 96, is incorporated herein by reference. Because they reduce peak and trough plasma concentrations, as compared to conventional immediate release (IR) oral dosage forms, sustained release dosage forms are particularly useful for providing a therapeutic plasma concentration of O-desmethyltramadol while (i) avoiding the side effects associated with high peak plasma concentrations, and/or (ii) with respect to low trough O-desmethyltramadol plasma concentrations that occur with IR dosage forms, avoid a lack of synergy with tramadol or lack of efficacy altogether.

The term 'immediate release' or 'IR' shall mean that the dosage form yields a dissolution or disintegration time of less than about 90, 60, 30 or 20 minutes (preferably 20 minutes) (85% or more dissolving or disintegrating) when tested according to USP 28 <701>, USP 28<711> or the method in the online FDA CDER method database for the particular commercial formulation. As used herein, 'immediate release' shall also encompass formulations wherein the active ingredient is fully solubilized, where the dissolution time is zero by definition. As used herein, the term 'sustained release' or 'SR' shall mean that the dosage form yields a dissolution or disintegration time longer than would be required to meet the definition of immediate release.

In embodiments involving an oral dosage form of O-desmethyltramadol and tramadol, O-desmethyltramadol is preferably provided in a sustained release dosage form and tramadol is provided as an immediate release dosage form (e.g., each within discrete granules encompassed within the same capsule, wherein the O-desmethyltramadol granules provide sustained release, or alternatively as a multi-layer tablet, wherein one layer provides sustained released and the other layer provides immediate release). In other preferred embodiments of an oral dosage form, O-desmethyltramadol and tramadol are both provided in a sustained release dosage form, wherein each form provides sustained release with the same or different kinetics (e.g., each within sustained release granules encompassed within the same capsule, or alternatively, both within the same monolithic sustained release tablet). The sustained release dosage form thus comprises a substrate and a pharmaceutically effective amount of O-desmethyltramadol or tramadol or both, or pharmaceutically acceptable salts thereof, wherein the term 'substrate' refers to any material or combination of materials, or forms thereof, that results in the in vitro release (i.e., dissolution) pattern specified below for O-desmethyltramadol or tramadol or both.

In still other preferred embodiments, the sustained release or immediate release dosage forms will contain an additional active ingredient, for example, selected from the group consisting of acetaminophen, aspirin, ibuprofen, diclofenac, naproxen, indomethacin, fenoprofen, oxycodone, hydromorphone, codeine, hydrocodone and topiramate as provided in U.S. patent application Ser. Nos. 10/538,946, 12/252,117, 12/298,922, 12/604,560, 12/644,444 and U.S. Pat. Nos. 5,336,691, 5,516,803, 5,968,551 and 7,906,141, the disclosures of which are incorporated by reference herein.

A sustained release oral dosage form comprising a substrate comprising a pharmaceutically effective amount of O-desmethyltramadol or a pharmaceutically acceptable salt thereof (i.e., the active ingredient), will have a dissolution profile (i.e., rate) in vitro when measured using the USP Apparatus I Basket Method at 75 rpm in 900 ml 0.05 M phosphate buffer with a pH 7.2 at 37° C. of:

between 15 and 74% O-desmethyltramadol released after 1 hour;
between 28 and 91% O-desmethyltramadol released after 2 hours;
between 38 and 101% O-desmethyltramadol released after 3 hours;
between 47 and 105% O-desmethyltramadol released after 4 hours;
between 59 and 105% O-desmethyltramadol released after 6 hours;
between 68 and 105% O-desmethyltramadol released after 8 hours;
between 75 and 105% O-desmethyltramadol released after 10 hours;
between 79 and 105% O-desmethyltramadol released after 12 hours;
about 100% O-desmethyltramadol released after 24 hours; by weight, said sustained release oral dosage form providing a therapeutic effect for about 6 to about 12 hours after oral administration and suitable for dosing every 6 to 24 hours. The term 'suitable for dosing every 6 to 24 hours' means that the dosage forms are such that they can be administered every 6 to 24 hours and give effective blood plasma concentrations of O-desmethyltramadol, or optionally O-desmethyltramadol and tramadol, such that they are effective to treat acute, chronic and neuropathic pain, and more generally, are effective for relieving a disorder modulated by opiate receptor activity and/or monoamine activity. The sustained release oral dosage forms can be dosed every 24 hours but also can be dosed differently, e.g., every 12 hours (b.i.d.) or every 6 hours (q.i.d.).

In a preferred embodiment there is provided a sustained release oral dosage form as defined above that will have a dissolution profile, as measured using the method defined above, as follows:
between 21 and 72% O-desmethyltramadol released after 1 hour;
between 34 and 89% O-desmethyltramadol released after 2 hours;
between 44 and 99% O-desmethyltramadol released after 3 hours;
between 52 and 105% O-desmethyltramadol released after 4 hours;
between 65 and 105% O-desmethyltramadol released after 6 hours;
between 70 and 105% O-desmethyltramadol released after 8 hours;
between 81 and 105% O-desmethyltramadol released after 10 hours;
between 86 and 105% O-desmethyltramadol released after 12 hours;
about 100% O-desmethyltramadol released after 24 hours; by weight.

In a more preferred embodiment there is provided a sustained release oral dosage form as defined above that will have a dissolution profile, as measured using the method defined above, as follows:
between 25 and 54% O-desmethyltramadol released after 1 hour;
between 40 and 69% O-desmethyltramadol released after 2 hours;
between 52 and 82% O-desmethyltramadol released after 3 hours;
between 61 and 92% O-desmethyltramadol released after 4 hours;
between 78 and 101% O-desmethyltramadol released after 6 hours;
between 83 and 105% O-desmethyltramadol released after 8 hours;
between 89 and 105% O-desmethyltramadol released after 10 hours;
between 91 and 105% O-desmethyltramadol released after 12 hours;
about 100% O-desmethyltramadol released after 24 hours; by weight.

In a most preferred embodiment there is provided a sustained release oral dosage form as defined above that will have a dissolution profile, as measured using the method defined above, as follows:
between 25 and 35% O-desmethyltramadol released after 1 hour;
between 40 and 50% O-desmethyltramadol released after 2 hours;
between 52 and 62% O-desmethyltramadol released after 3 hours;
between 61 and 71% O-desmethyltramadol released after 4 hours;
between 78 and 88% O-desmethyltramadol released after 6 hours;
between 83 and 93% O-desmethyltramadol released after 8 hours;
between 89 and 99% O-desmethyltramadol released after 10 hours;
between 91 and 105% O-desmethyltramadol released after 12 hours;
about 100% O-desmethyltramadol released after 24 hours; by weight.

In embodiments of an oral dosage form wherein O-desmethyltramadol and tramadol are both provided in a sustained release dosage form, the dissolution rate of tramadol will fall within the same % ranges as a function of time as defined above for O-desmethyltramadol. In a preferred embodiment, O-desmethyltramadol and tramadol will be in the same sustained release oral dosage form together, and will have substantially the same dissolution kinetics (i.e., the 'same dissolution kinetics' shall mean the difference between the % O-desmethyltramadol and % tramadol released at a given time point will be less than or equal to 10% and more preferably 5%).

As mentioned above, in order to act synergistically, the ratios of the blood plasma levels of tramadol:M1 should be within certain ranges and in particular the blood plasma levels of these ingredients should be in the range of about 0.4:1 to about 33:1, in particular from about 0.4:1 to about 6:1 of tramadol:M1, and from about 0.5:1 to 2.0:1 of tramadol:M1. An optimum ratio for these ingredients is about 0.5:1 to 2.0:1 tramadol:M1. It further has been found that when M1 is released in vitro in the quantities outlined above, upon multiple administrations during specific periods of time, e.g., every 24 hours, or, which is preferred, every 6 hours, the plasma concentrations of M1 in vivo reach a steady-state and are constant within certain ranges during an extended period of time. It has additionally been found that in pharmaceutical preparations as described herein, containing M1 or a salt thereof and tramadol, when the release of M1 follows the release pattern as outlined above, the ratio of the plasma concentrations of tramadol vis a vis M1 is constant within certain ranges. This ratio has been found to approximate 0.5:1 to 2.0:1 (w/w) or upon selection of the appropriate concentrations of the tramadol and M1, or its salt form, and of the substrate and other carriers in a pharmaceutical dosage form, this ratio may be about 0.5:1 to 2.0:1. This equally means that upon multiple administrations of the pharmaceutical preparations herein, also during specific periods of time, e.g., every 24 hours, or, which is preferred, every 6 hours, the plasma concentrations of tramadol in vivo reach a steady-state and are constant within certain ranges during a long period of time. The above findings related to blood plasma levels of tramadol and M1 allow both agents to act synergistically in any subject irrespective of their CYP2D6 genotype, and therefore be effective in treating a disorder modulated by opiate receptor activity and/or monoamine activity, including acute, chronic and neuropathic pain, in any subject. Further, subjects with the UM phenotype will experience fewer adverse events.

As used herein, 'constant within certain ranges' means that there can be fluctuations of the M1 or tramadol plasma concentrations, or of the above stated ratio of the M1:tramadol plasma concentrations within an acceptable range, e.g., within 100% in particular, within 75%, further in particular within 50%. Alternatively, fluctuation of M1 or tramadol plasma concentrations can be expressed by the steady-state 'fluctuation index' which is defined as follows: $F_i=[Css_{max}-Css_{min}]/Css_{Av}$ wherein $F_i$ is the fluctuation index, $Css_{max}$ the maximal plasma concentration at steady-state, $Css_{min}$ the minimal plasma concentration at steady-state, and $C_{AV}$ the average plasma concentration at steady-state, where $C_{AV}=(Css_{max}+Css_{min})/2$. The fluctuation index can vary but for example is 40% to 50%, 50% to 60%, 60% to 80% and 80% to 110%.

The in vitro dissolution profiles of M1 and tramadol outlined above are supported by an in vitro/in vivo correlation (IVIVC) model that correlates plasma M1 concentrations and the in vitro release of M1 and tramadol from immediate-release and sustained-release dose forms. Administration of an effective amount of M1 or tramadol will show a particular course of M1 plasma concentrations. Ideally, plasma tramadol should follow the same course as M1 so that the ratio of the plasma concentrations of both agents remains more or less constant, although this is not essential. By consulting the IVIVC model of M1 and tramadol it has been found that it is possible to predict which plasma M1 concentration profile correlates with a given in vitro release profile and vice versa (i.e., a reversed IVIVC). The latter allows a reverse calculation of the in vitro release profile that would cause a particular in vivo plasma M1 profile.

Typically, the pharmaceutical preparations comprise M1 or its salt form in a suitable sustained release form, which may be any form that affords release of M1 within the ranges specified above.

In certain embodiments, the preparations comprise sustained release forms wherein the M1 or its salt form is incorporated in a suitable matrix, which may be a sustained release matrix or a normal release matrix having a sustained release coating. The sustained release form may take various forms, e.g., particles of different sizes, pellets (or beads), tablets, phases within a larger unit such as layers or sections of other shape within a larger unit (e.g., as in a multi-layer or a bull-eye tablet). A number of such formats as well as the unit dosage forms in which these can be incorporated will be outlined in more detail hereinafter.

As used herein the term 'phase' refers to a defined three dimensionally shaped section in a tablet dosage form that contains the same material and wherein each phase is separated from the other. Examples of phases are layers, which are incorporated in bi- or multi-layer tablets. Other examples are cylindrical, spherical or other tri-dimensionally shaped sections that can be present in tablets. This gives rise to different tablet formats such as the so-called 'bull-eye' tablets, or concentric tablets (a central cylindrically shaped section completely surrounded with one or more further cylindrical layers (i.e., a ring-like combination), or 'coated' tablets wherein the coating is a layer completely surrounding a tablet nucleus and the like tablet formats. Preference is given to bi- or multi-layer tablets.

Preferred embodiments are tablets that contain at least two phases, in particular tablets that contain at least two layers.

In particular embodiments, the major part of the M1 or its salt form and of the tramadol are in different phases of the said pharmaceutical preparations. In said embodiments, an at least one phase may contain either the major part of tramadol or the major part of M1 or a salt-form thereof. In particular embodiments, one phase contains the major part of M1 or a salt thereof and another phase contains the major part of tramadol.

As used herein, 'major part' means that the major quantity of the M1 or its salt form or of tramadol is present in a particular phase. Preferably the term 'major part' refers to a situation where at least more than about 90% of the concerned active ingredient is present in a particular phase, for example more than 95%, or more than 98%, or more than 99%, or even more than 99.5%. The same applies to the situation take particular forms such as layers.

Most preferably a phase containing one of both active ingredients should contain only a minute amount of the other active ingredient, or even none of the other active ingredient, for example a phase may contain tramadol and a minute amount, e.g., less than 1%, or less than 0.5% of M1 or a salt form thereof, or vice versa.

Preferably a phase comprising M1 or a salt form thereof is adjacent to a phase containing tramadol.

Of particular interest are tablets that are biphasic, the latter being preferred, or multiphasic, e.g., having 3, 4, 5 or more phases. At least one layer should comprise M1 or a salt form thereof but in case of multiphasic tablets, more than one layer comprising M1 or a salt form can be present. Of still further interest are those preparations in which one or more of the phases are layers.

Particularly preferred embodiments are tablets wherein tramadol is present in amounts from about 10 mg to 500 mg tramadol per unit, preferably from about 25 mg to about 200 mg of tramadol per unit, e.g., tablets having 25, 50, 100 or 200 mg per unit.

In a particular aspect, the tablets contain an effective amount of tramadol, wherein the tablets have at least one layer that contains from about 20% to about 100%, in particular from about 30% to about 90% or from about 50% to 80% of polymeric matrix material. The hygroscopic matrix material containing layer may contain other ingredients such as the ingredients mentioned hereinafter.

Formulations suitable for providing sustained release of O-desmethyltramadol and immediate release of tramadol, or the sustained release of both O-desmethyltramadol and tramadol are provided in U.S. patent application Ser. Nos. 12/225,498, 12/252,117, 12/298,922, 12/336,495, 12/406,272, 12/604,560, 12/644,444 and U.S. Pat. Nos. 5,427,799, 5,580,578, 5,591,452, 6,090,411, 6,143,327, 6,245,357, 6,254,887, 7,074,430, 7,611,730 and 7,906,141 the disclosures of which are incorporated by reference herein. The sustained release preparation should release O-desmethyltramadol, and optionally tramadol, in vitro in the quantities outlined above. In some embodiments, these are obtained by measurement using the USP Apparatus I Basket Method at 75 rpm in 900 ml 0.05 M phosphate buffer with a pH 7.2 at 37° C. and using spectrophotometry at an appropriate detection wavelength, e.g., at 270 nm in the case of O-desmethyltramadol and tramadol. Release of the active ingredients can also be measured in situ with a fiber optic dissolution system, using the second derivative correction method at a suitable wavelength range, which, in case of tramadol is in the range of 283 to 289 nm. Alternatively, release of O-desmethyltramadol and tramadol from a combination dosage form (i.e., both in one SR form, each in a different SR form, or one in an SR and the other in an IR form) can be separately measured using high performance liquid chromatography (HPLC) and a suitable detection system such as, for example, UV detection at an appropriate wavelength (e.g., at 274, 272 or 271 nm for tramadol HCl, M1 HCl and M1 free base, respectively), or with a refractive index detector.

In general, sustained release may be achieved using any of three broad categories of delivery: (1) sustained release from a matrix, (2) sustained release from a reservoir and (3) sustained release from coated-beads and multi-particulates.

Sustained Release from a Matrix.

Where the matrix is a sustained release it may comprise suitable digestible hydrophilic or hydrophobic polymeric or non-polymeric materials.

Examples of such polymeric materials are hydrophilic or hydrophobic polymers, such as polysaccharides, in particular gums (further in particular pH dependent gums), cellulose ethers, especially alkylcelluloses, in particular $C_1$-$C_6$ alkyl cellulose, especially ethyl cellulose, acrylic resins, protein-derived materials, polyalkylene glycols, polysaccharide gums such as xanthan gum, and the like. Preferred are polymers such as polyvinyl acetate and polyvinylpyrrolidone and mixtures thereof, in particular the mixture known as Kollidon® SR which is polyvinyl acetate (8 parts w/w) and polyvinylpyrrolidone (2 parts w/w).

Examples of non-polymeric materials that can be used are digestible lipids having a long chain alkyl moiety, which may be straight or branched, saturated or unsaturated, substituted or unsubstituted. Of particular interest are $C_{8-50}$, especially $C_{12-40}$ lipids. Examples comprise fatty acids, fatty alcohols, glyceryl esters of fatty acids, mineral and vegetable oils and waxes. Lipids having a melting point of between 25 and 90° C. are preferred.

The sustained release form may conveniently contain between 1% and 90%, in particular from 10% to 90%, further in particular from 20% to 80% (by weight) of one or more hydrophilic or hydrophobic polymers or digestible lipids. In embodiments where the polymeric material is a mixture of polyvinyl acetate and polyvinylpyrrolidone and mixtures such as Kollidon® SR or a polysaccharide gum such as xanthan gum, alginate or gum Arabic, the preparation may contain between 20% and 90%, in particular from 30% to 80% (by weight). As used herein, 'alginate' refers to alginate or its salts, in particular to its alkali metal salts such as sodium or potassium salts. In embodiments containing polyalkylene glycols, the preparation may in particular contain up to 60% (by weight) of one or more polyalkylene glycols. In further particular embodiments, the preparation may contain up to 60% (by weight) of at least one digestible, long chain lipid.

Of interest are sustained release matrixes comprising xanthan gum optionally in mixture with other gums, in particular with other pH dependent gums such as, for example, alginate.

Optionally, the sustained release matrix may also contain other pharmaceutically acceptable ingredients which are conventional in the pharmaceutical art such as diluents (in particular lactose), lubricants, binders, granulating aids, colorants, flavorants, surfactants, pH adjusters, anti-adherents and glidants (e.g., colloidal silica), and plasticizers (e.g., dibutyl sebacate) and other suitable ingredients (e.g., ammonium hydroxide, oleic acid). Preferred are ingredients described in U.S. Pat. No. 6,090,411 that further control the rate of matrix erosion through changes in gel thickness, electrolyte ionization, and ionic interactions (i.e., CDT® technology).

The sustained release form may conveniently be film coated using any film coating material conventional in the pharmaceutical art. A film coat is added e.g., as a finish, for coloring purposes or taste masking or a combination of these. Preferably an aqueous film coating is used.

Alternatively, the sustained release form may comprise an immediate or sustained release matrix, as a core, and further having a controlled release coating. In such embodiments the immediate release core may be prepared via art known procedures, e.g., by a suitable granulation process followed by compression, or by direct compression, followed by a coating step with a coating material that ensures controlled release. In such preparations, the immediate release section or core of the preparation may contain any of the usual ingredients usually employed to make such immediate release sections or cores. Any of the ingredients mentioned herein with respect to carriers used for immediate release forms can be conveniently employed. In the case of a sustained release core, such embodiments may be prepared via the methods herein, followed by a coating step with a coating material that ensures controlled release.

The sustained release profile of O-desmethyltramadol and optionally also tramadol can be adjusted in a number of ways. For instance a higher loading of the drug will be associated with increased initial release rates. By selecting particular ingredients and by controlling the relative amounts thereof in the preparation it is possible to adjust the release profile of O-desmethyltramadol and in embodiments that provide for tramadol in a sustained release form, also the release profile of tramadol. Such particular ingredients for example are the matrix materials mentioned above, e.g., the polymeric materials mentioned above.

Sustained Release from a Reservoir.

In further embodiments, the sustained release form comprises a reservoir containing the active ingredient or active ingredients, or a plurality of reservoirs each containing one or more active ingredients. Reservoir devices usually consist of a semi-permeable barrier that is involved in the release of the active ingredient from a central site within the tablet. The manufacturing process may involve incorporating laser-bored orifices in the semi-permeable membrane. Representative sustained release forms comprising a reservoir are disclosed in for example U.S. Pat. No. 6,245,357. Other sustained release forms comprising a reservoir include for example an osmotic dosage form for delivering various drugs to a patient is presented in U.S. Pat. Nos. 3,845,770 and 3,916,899. The dosage forms disclosed in these patents are manufactured, for example, comprising a wall that surrounds a compartment comprising a drug with an exit in the wall for delivering the drug to a patient. In U.S. Pat. Nos. 4,008,719, 4,014,334, 4,058,122, 4,116,241 and 4,160,452 are made available dosage forms comprising an inside and an outside wall made of poly(cellulose acylate) for delivering a dosage of drug to a patient in need thereof.

Sustained Release from Bead and Multi-Particulates.

In further embodiments, the sustained release form comprises spherical pellets containing the active ingredient and a spheronizing agent. The same active ingredient may also be blended in a plurality of sustained release forms so as to provide a blend of spherical pellets with differing dissolution rates for extended release or pulsitile release. The pellets may be film-coated or not. The spheronizing agent may be any suitable pharmaceutically acceptable material, which can be spheronized together with the active ingredient to form pellets. The term 'spherical pellet' is meant to comprise pellets, beads or spheroids that are more or less of regular shape. In particular embodiments the shape is round or about round, i.e., having or approaching the shape of a small sphere.

The average size of the pellets may vary but preferably the diameter is in the range of about 0.1 mm to 3 mm, in particular from about 0.5 mm to about 2 mm, more preferably about 1 mm.

The size distribution of the pellets may vary but in general it is preferred that it has limited variation. It may vary between within a range of 10 to 20%. The size distribution may vary in a statistical manner, i.e., in a bell-shaped curve wherein e.g., 90% or e.g., 95% of the number of pellets are within a size range that varies between about 10% to about 20% of the average sizes mentioned above.

The active ingredient (i.e., O-desmethyltramadol and optionally further tramadol) or its pharmaceutically acceptable salt is present in an amount, which is in the range of from about 0.1 to about 50%, in particular from about 1 to about 40%, more in particular from about 10 to about 35%, w/w relative to the total weight of the pellet.

The pellets may further comprise an appropriate carrier which may be any carrier known in the art used for making pellets. Particular carrier materials are spheronizing agents that may be any suitable pharmaceutically acceptable material, which may be spheronized together with the active ingredient to form pellets. A preferred spheronizing agent is microcrystalline cellulose. The microcrystalline cellulose used may suitably be, for example, the product sold under the trade name 'Avicel™'. The spheronizing agent is present in an amount, which is in the range of from about 25% to about 90%, in particular from about 35% to about 70% w/w, relative to the total weight of the pellet.

Optionally the pellets may contain other pharmaceutically acceptable ingredients such as binders, bulking agents and colorants. Suitable binders, some of which may also contribute to the sustained release properties of the pellets, include water-soluble polymers, e.g., water-soluble hydroxyalkyl celluloses such as hydroxypropyl cellulose and hydroxypropylmethyl cellulose, or water insoluble polymers, such as acrylic polymers or copolymers, or alkyl celluloses such as, for example, ethylcellulose. Suitable bulking agents include lactose or colloidal silicon dioxide. The amount of these other ingredients in the pellets will be relatively small, e.g., lower than 30%, or 20%, or even lower than 10% or 5% w/w relative to the total weight of the pellet.

The pellets for use in the preparations of some embodiments are made by an extrusion process followed by spheronization. The mixture used in the extrusion process comprises active ingredient, a suitable carrier material and other optional ingredients, and a suitable lubricant. The lubricant usually is water and the mixture for extrusion typically is converted into a granulate. After extrusion, the extrudate is spheronized to obtain pellets. If desired, the latter may be coated with a suitable coating material.

If the active ingredients act as an additional binder in the mixture that is extruded and spheronized (i.e., form a sticky mass upon contact with water and/or the other excipients used in the extrudate mixture), the addition of a dry lubricant will be preferable. Apart from providing lubrication, the dry lubricant also allows the material to be extruded at a much lower moisture content thereby reducing the sticking observed in the spheronizer.

Further embodiments thus are spherical pellets for sustained release comprising O-desmethyltramadol or tramadol or a salt thereof, or O-desmethyltramadol and tramadol or salts thereof, a spheronizing agent and dry lubricant. In a further aspect, said pellets have a low water content. If desired, the pellets may be coated.

The dry lubricant in particular is a mono-, di- or triglyceride, or mixtures thereof. Suitable mono-, di- or triglycerides are the mono-, di- or triesters of glycerine and one or more fatty acids. The mono-, di- or triglycerides may contain the same or different fatty acid residues or mixtures thereof, e.g., technical mixtures obtained from saponification of natural oils. Of particular interest are fatty acid triglycerides wherein the fatty acid residue has from 12 to 30 carbon atoms and is saturated or partially unsaturated or may be substituted, e.g., with one or more hydroxy functions. Preferred are mono-, di- or triglycerides derived from $C_{18-30}$ fatty acids, in particular derived from $C_{22-26}$ fatty acids. Of particularly preferred interest are behenic acid mono-, di- or triglycerides.

The dry lubricant preferably is solid at room temperature and has a melting point or melting range which is in the range of 60° C. to 90° C., in particular is in the range of 70° C. to 80° C. A particularly suitable dry lubricant is the glyceride mixture sold under the trade name 'Compritol™ 888ATO' which is a mixture of glyceryl mono-, di- and tribehenate, the dibehenate fraction being predominant, and having a melting range of about 69-74° C.

Preferably, the dry lubricant is selected such that it does not impact the dissolution behavior of the active ingredient.

The dry lubricant is present in an amount, which is in the range of from about 2% to about 50%, in particular between 10% and 35% w/w, relative to the total weight of the pellet.

Of particular interest are pellets that have a low water content. In particular embodiments, the water contents in the pellets is lower than 5%, more in particular lower than 3%, w/w relative to the total weight of the pellet.

The spherical pellets, containing a dry lubricant, can be prepared by a process comprising extruding a mixture of the active ingredient with a suitable carrier in the presence of a dry lubricant and spheronizing the extrudate, wherein the dry lubricant is a triglyceride. The amount of dry lubricant in this mixture may vary but in general is comprised between 10% and 35% (w/w). A small amount of water may be added to the mixture. In a particular execution, the amount of water is 5% or lower, or 3% or lower, or 1.5% or lower, w/w, relative to the total weight of the mixture for extrusion. In a specific process the pellets are subsequently coated with a suitable coating.

The ingredients may be mixed together in any given sequence. In one embodiment, the dry lubricant is added to a mixture of active ingredient and the carrier material at room temperature. The mixture is subsequently extruded through a small orifice. The diameter of the latter is in relation to the size of the pellets that are eventually produced from the extrudate. In one embodiment, the diameter of the orifices is in the range of 0.5 mm to 2.0 mm. The extrusion may be done at slightly elevated temperature but preferably is performed without applied heating. The extruded material is subsequently placed into a spheronizer where it is spun at high speed.

In specific embodiments of this disclosure, the pellets (or spheroids), with or without dry lubricant, are subsequently coated with a suitable coating using art known methods. The coating can either be a functional coating or a diffusion controlling coating.

A functional coating may be applied for e.g., taste masking, protection of the pellets, to have improved stability (shelf-life) or for identification (for example by coloring). Functional coating often will be film coating, using any film coating material conventional in the pharmaceutical art. Preferably an aqueous film coating is used.

Diffusion controlling coatings are designed to achieve a target release profile such as controlled or sustained release permitting release of the active ingredient at a controlled rate in an aqueous medium. Suitable controlled or sustained release coating materials include water-insoluble waxes and polymers such as polymethacrylates, for example Eudragit™ polymers, or water insoluble celluloses, in particular alkyl celluloses such as ethylcellulose.

Optionally, water-soluble polymers such as polyvinylpyrrolidone or water-soluble celluloses such as hydroxypropylmethyl cellulose (HPMC) or hydroxypropylcellulose (HPC) may be included. Further components that may be added are water-soluble agents such as polysorbate. Of particular interest is ethylcellulose (EC). Preferably, a suitable plasticizer is added. A coating material that is particularly suitable is the coating material sold under the trade name Surelease™ (Colorcon), which is a dispersion of ethylcellulose.

Alternatively the active ingredient or its salt-form may be coated onto inert non-pareil beads, in particular onto sugar beads, and the drug loaded beads coated with a material, which permits control of the release of the active ingredient into the aqueous medium.

Because of the bitter taste of one or more of the active ingredients, the pellets may be coated for taste-masking purposes although this may be of less importance if the pellets are used in a capsule dosage form.

Placement of Active Ingredients in the Dose Form.

The tramadol in the preparations can be present throughout the pharmaceutical preparations disclosed herein, or in particular sections thereof. In particular embodiments it is present in one or more phases of the preparations. Preferably, the tramadol is present in one or more phases that do not contain M1.

The phases can take a variety of forms, e.g., sections in a tablet, or they can take the form of pellets. These forms can be prepared following art-known procedures. In the particular case of sections in a tablet preparation, procedures can be applied such as granulation followed by partial or complete compression, or direct partial or complete compression.

Usually, the tramadol is formulated into a suitable formulation. This is prepared by mixing tramadol with suitable ingredients into different formulation types such as powders, granulates, pellets and the like. The powder or granulate formulations may be compressed partially or completely to form appropriate phases for incorporation in bi- or multiphasic preparations. Particular phases are layers for incorporation in bi- or multi-layer tablets. Most preferably, the tramadol formulation will be for immediate release, i.e., the ingredients and the formulation form are selected such that release of tramadol is as quickly and as complete as possible. Ideally, release is 100% after a short period of time, e.g., within ½ hour.

In tablet preparations, suitable tableting excipients may be added e.g., one or more of the standard excipients such as diluents, lubricants, binding agents, flow aids, disintegrating agents, surface active agents or water soluble polymeric materials. Suitable diluents are e.g., microcrystalline cellulose, lactose and dicalcium phosphate. Suitable lubricants are e.g., magnesium stearate and sodium stearyl fumarate. Suitable binding agents are e.g., hydroxypropyl methyl cellulose, polyvidone and methyl cellulose. Suitable disintegrating agents are starch, sodium starch glycolate, crospovidone and croscarmellose sodium. Suitable surface active agents are Poloxamer 188®, Polysorbate 80 and sodium lauryl sulfate. Suitable flow aids are talc, colloidal anhydrous silica.

Double Layer Tablets.

One particular execution of the sustained release preparations of the present disclosure are double layer (or bilayer) tablets. These comprise one layer containing M1 dispersed in a suitable matrix and another layer that contains tramadol.

The tramadol containing layer preferably is composed of excipients typically used for tramadol oral dosage forms such as tablets. Examples of such excipients comprise any of those mentioned above in relation to the immediate-release formulation of tramadol.

The M1 layer comprises any of the sustained release matrix materials described above. The matrix may in particular comprise polyvinyl acetate and polyvinylpyrrolidone and mixtures thereof, more in particular the mixture known as Kollidon® SR. Or alternatively, the M1 layer may comprise a hydrophilic swellable polymeric matrix such as hydroxypropylmethyl cellulose and a salt (i.e., an 'electrolyte') as described more fully in U.S. Pat. No. 6,090,411.

The M1 layer may contain from about 10 mg to 100 mg M1 hydrochloride per unit, preferably from about 15 mg to about 75 mg of M1 hydrochloride per unit, or from about 20 mg to about 40 mg of M1 hydrochloride per unit. In case of application of M1-free base or other salts, an equivalent amount of active on a molar basis is used.

In particular embodiments, the M1 layer contains an effective amount of M1, or a pharmaceutically acceptable salt thereof, dispersed in a matrix wherein the matrix contains from about 20% to about 90%, in particular from about 30% to about 80% of polyvinyl acetate and polyvinylpyrrolidone, more in particular a mixture thereof, still more in particular the 8:2 (w/w) polyvinyl acetate:polyvinylpyrrolidone mixture known as Kollidon® SR. The percentages mentioned herein are w/w relative to the total weight of the dosage form.

The M1 layer may additionally contain further ingredients such as the ingredients mentioned previously in relation to the tramadol layer, in particular starches, kaolin, lubricants, binders and the like. Preferred additional carriers are lubricants, e.g., magnesium stearate, flow enhancers or fillers, e.g., silica (silicon dioxide), cellulose, fillers such as sugars, in particular lactose, titanium dioxide and the like.

In further particular embodiments, the M1 layer contains microcrystalline cellulose (MCC) as a filler and magnesium stearate as a lubricant. MCC is added to improve compressibility of the blend. Magnesium stearate is added to avoid tablet sticking on the lower or upper punch during the compression. The concentration of magnesium stearate in the M1 layer may vary but good results are obtained when adding it in amounts ranging from about 0.5 to about 1.5% (w/w relative to the total weight of the dosage form). The concentration of MCC in the M1 layer may vary but good results are obtained when adding it in amounts which range from about 5% to about 80%, preferably from about 10% to about 65%, more preferably from about 20% to about 50% (w/w relative to the total weight of the dosage form).

The M1 layer can be prepared by mixing M1 or its salt form with polyvinyl acetate and polyvinylpyrrolidone, more in particular the mixture thereof, still more in particular with Kollidon® SR while adding optional ingredients. The latter may also be added after the mixing of M1 and Kollidon® SR. The thus obtained mixtures are subsequently compressed, either by direct compression, which is preferred or by preparing a granulate and subsequent compression.

It has been found that when using M1 and polyvinyl acetate and polyvinylpyrrolidone mixtures, the tablets can be prepared by direct compression. The mixtures for direct compression preferably contain a lubricant, in particular magnesium stearate. They may additionally contain a filler, in particular a sugar such as lactose. They may furthermore contain a flow enhancer (i.e., a glidant) such as colloidal silica (silicon dioxide). In the mixtures for direct compression the lubricant preferably is present in concentrations in the range of about 0.5% to about 1.0%. The filler is present in concentrations from about 5% to about 80%, preferably from about 10% to about 65%, more preferably from about 20% to about 50%. The flow enhancer is present in concentrations from about 0.4% to about 1.5%, preferably about 0.5% to about 1.0%. All percentages herein are w/w relative to the total weight of the M1 containing phase or phases.

Particular embodiments are coated tablets, in particular film-coated tablets. Coated tablets are easier to swallow than uncoated tablet cores, are usually easier to distinguish from other tablet, in particular when the film-coat contains a dye or a pigment, and may furthermore have an improved stability (shelf-life). In the present instance coating is mainly for taste masking purposes because of the bitter taste of M1 and tramadol. Coatings are applied using art known methods using art known materials usually applied for this purpose. Particularly attractive coating products are based on suitable film-forming polymers such as hydroxypropylmethylcellulose (HPMC) or polyvinylalcohol (PVA). Preferably, a plasticizer is added. Examples of suitable plasticizers are polyethylene glycol or derivatives thereof such as polyethoxylated alkylglycerides, e.g., polyethoxylated stearyl monoglyceride, in particular the material sold under the trade name Macrogol™. Further ingredients may be added to the coating such as fillers, dyes or pigments, flavors, sweeteners and the like components. Examples of such further ingredients are lactose, titanium dioxide, starch and the like. Particularly suited as coating materials are the Opadry™ materials which mainly contain the before mentioned materials and further ingredients such as plasticizers, e.g., polyethylene glycol.

In a preferred embodiment, first the M1 layer is produced by direct compression whereupon tramadol granules are placed on top of the compressed M1 layer as to form a second layer whereupon the whole is compressed to form a bi-layer tablet.

In particular embodiments there are provided bi-layer tablets comprising an M1 layer and a tramadol layer wherein both layers are separated by a suitable layer that may function as an isolator. This third layer may be comprised of suitable inert materials such as cellulose or lactose. Such embodiments may be prepared by first producing the M1 layer by partial or complete compression of a suitable M1 containing mixture whereupon the isolator material is put on the M1 layer followed by a second compression, whereafter a suitable tramadol containing mixture is put on top of the isolator layer as to form a third layer whereupon the whole is compressed to form a tri-layer tablet. The suitable M1 containing mixture or suitable tramadol mixture may be a powder suitable for direct compression or a granulate obtained by a granulation process. The isolator layer may be desirable e.g., to avoid certain interactions between the components in each layer or to shield off humidity.

Multi-Layer Tablets.

Further embodiments are multi-layer tablets having multiple layers of tramadol and M1, optionally separated by one or more isolator layers.

Further Tablet Formulations.

In still further embodiments are M1 tablets coated with a tramadol coating. In this type of preparations, a suitable core containing M1 or a salt thereof in a sustained release form is coated with a tramadol-containing coating, e.g., by spraying with a suitable liquid formulation that contains tramadol. The core itself can be a tablet or another shaped phase.

Still further embodiments are so-called "bull-eye" tablets, which are tablets with a cavity in which another tablet fits. The tablet with the cavity in particular is U-shaped.

The tablet with a cavity may contain the M1 and the other tablet the tramadol or vice versa. Bull-eye tablets can be made following art-known procedures using specially adapted punches in a tableting machine.

In any of the preparations that are tablets, the latter may be coated with a suitable coating material.

Preparations with Pellets.

Further embodiments are dosage forms comprising M1 formulated in pellets, hereafter referred to as 'M1 pellets'. The M1 pellets may be prepared according to methods as described above and may be coated, if desired.

The M1 pellets in turn may be coated with a tramadol containing coating, e.g., by spraying the M1 pellets with an appropriate formulation containing tramadol. These M1 pellets with a tramadol coating may be filled into capsules.

The M1 pellets can be filled in capsules together with an appropriate formulation of tramadol e.g., formulated as a powder, granulate, or formulated itself as a pellet. The M1 pellets and the tramadol formulation may be filled into the capsule in any give sequence, first the M1 pellets followed by the tramadol formulation or vice versa or the two together or the two together as a mixture, e.g., a mixture of tramadol and M1 pellets.

In further embodiments there are provided capsules containing M1 pellets and one or more tramadol tablets. The tramadol tablets will evidently be of such size and shape that it fits into a capsule. Preferably only one tramadol tablet is filled into one capsule.

In still further embodiments there is provided a so-called 'capsule into capsule' dosage form, i.e., a capsule containing a suitable tramadol formulation is put into a bigger capsule containing M1 pellets. Or vice versa, a capsule containing M1 pellets is put into a bigger capsule containing a suitable tramadol formulation. A suitable tramadol formulation can be a powder or a pellet formulation.

Still other embodiments are sachets filled with amounts of M1 pellets and a suitable tramadol formulation.

In still another aspect, an embodiment concerns a process for manufacturing a pharmaceutical dosage from, said method comprising filling the M1 pellets into a suitable container and further adding a suitable tramadol formulation. In a preferred aspect the container is a capsule. Another type of container is a sachet.

A particular embodiment provides unitary dosage forms which comprise M1 HCl pellets as described herein in an amount that is such that the dosage form contains an effective amount of M1 HCl. Particular embodiments of such dosage forms may contain from about 10 mg to 100 mg M1 HCl per unit, preferably from about 15 mg to about 75 mg of M1 HCl per unit, or from about 20 mg to about 50 mg of M1 HCl per unit.

In general, the all the compositions above may be presented in unit dosage form. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient.

In general, the total daily dose of M1 ranges from about 40 mg per day to about 200 mg per day, preferably about 60 mg per day to about 160 mg per day, and more preferably, about 80 mg per day to about 160 mg per day, in single or divided doses. If given together with M1 in optional embodiments, the total daily dose of tramadol ranges from about 20 mg per day to about 400 mg per day, preferably about 40 mg per day to about 300 mg per day, and more preferably, about 60 mg per day to about 200 mg per day, in single or divided doses. It is further recommended that children, patients over 65 years old, and those with impaired renal or hepatic function, initially receive low doses and that the dosage is titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Tramadol is commercially available from a variety of sources, or may be made. O-desmethyltramadol may be synthesized from tramadol by demethylation of tramadol according to methods in the art, using for example, DIBAL or Ph$_2$PH and an alkyl lithium compound. Racemic O-desmethyltramadol may thus be obtained by demethylation of racemic tramadol, which is commercially available as a racemic mixture of the (R,R)- and (S,S)-enantiomers. Racemic tramadol may be resolved to yield its individual enantiomers and demethylated accordingly to yield the corresponding enantiomer of O-desmethyltramadol. Thus, demethylation of (1R,2R)-tramadol will yield (1R,2R)-O-desmethyltramadol, and demethylation of (1S,2S)-tramadol will yield (1S,2S)-O-desmethyltramadol.

The enantiomers of tramadol HCl may be resolved using D- or L-dibenzoyl tartaric acid (DBTA). Other methods that may be used for the resolution of enantiomers include formation of diastereoisomeric salts or complexes or derivatives which may be separated, for example, by crystallization, gas-liquid or liquid chromatography; selective reaction of one enantiomer with an enantiomer-specific reagent, for example, enzymatic oxidation or reduction, followed by separation of the modified and unmodified enantiomers; and gas-liquid or liquid chromatography in a chiral environment, for example, on a chiral support, such as silica with a bound chiral ligand or in the presence of a chiral solvent. It will be appreciated that where the desired enantiomer is converted into another chemical entity by one of the separation procedures described above, a further step is typically required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Part I. Active Pharmaceutical Ingredient

Example 1 (+/−)-Tramadol Free Base

Racemic tramadol hydrochloride (5.00 g, 16.7 mmol, Fluka) was dissolved in H$_2$O (50 ml). 10 N NaOH (2 ml) was added dropwise at room temperature, and a cloudy emulsion formed. The mixture was stirred for 15 minutes, then extracted into CH$_2$Cl$_2$. The combined organic filtrates were pooled, and washed with saturated NaCl, then dried over Na$_2$SO$_4$. The solution was filtered, then evaporated to yield a clear oil (4.30 g, 98%).

Example 2 (+/−)-O-Desmethyltramadol Free Base (M1)

Tramadol free base (50.3 g, 191 mmol) was dissolved in anhydrous toluene (130 mL) in an oven-dried 2 liter round bottom flask. The solution was cooled in an ice bath, and 1M diisobutylaluminum hydride (DIBAL) in toluene (500 mL, 500 mmol, 2.6 eq.) was added dropwise to the cooled solution under a nitrogen atmosphere. The addition took place over a period of 4.5 hours. Following addition, the solution was kept in the ice bath for 30 minutes, then allowed to warm to room temperature, then refluxed for 18 hours. The solution was removed from heat, and allowed to cool to room temperature, then placed in an ice bath. Anhydrous ethanol (250 mL) was then added dropwise to the solution over a period of 2 hours. Following addition, the solution was transferred to a 2 liter beaker, and water (250 mL) was added with vigorous stirring. The reaction mixture was filtered, and the toluene layer washed with water, saturated aqueous sodium chloride, and dried over sodium sulfate. The solution was filtered and evaporated to yield 38.1 grams of a while solid (80% yield). Analysis of this material by LC-MS in positive mode indicated that the material was >95% pure with the main peak having a mass consistent with M1 (m/z=250). Elemental analysis: (theory) C, 72.25; H, 9.30; N, 5.62, and O, 12.83; (found) C, 72.43; H, 9.35; N, 5.66; and O, 12.79.

Example 3 (+/−)-O-Desmethyltramadol HCl (M1 HCl)

In a three necked flask equipped with a thermometer, M1 free base (33.5 g, 135 mmol) was dissolved in anhydrous isopropyl alcohol (230 mL) and cooled in an ice bath. Anhydrous hydrogen chloride (g) was bubbled into the solution slowly as to keep the reaction temperature below 25° C. After the introduction of >7 grams of HCl (>195 mmol), the reaction flask was stoppered, and removed from the ice bath. A white precipitate formed upon cessation of HCl. The reaction mixture was allowed to warm to room temperature over 30 minutes, then vacuum filtered with a Buchner funnel. The filtered material was washed with anhydrous isopropyl alcohol, and dried under vacuum to constant weight to yield 33 grams of a white solid (86%). Analysis of this material by LC-MS in positive mode indicated that the material was >98% pure having a mass consistent with M1 (m/z=250). Elemental analysis: (theory) C, 63.04; H, 8.46; N, 4.90; and O, 11.20; (found) C, 63.13; H, 8.53; N, 4.90; and O, 11.20.

Part II. Immediate Release Dosage Forms

Example 4 Liquid Immediate-Release Oral Dosage Form

Racemic M1 was fully solubilized in water at a concentration of 1 mg/ml by adding 50 mg M1 HCl to 50 ml of water to provide Solution A. The appropriate amount of M1 was provided to a human subject by dispensing the appropriate volume of Solution A.

Example 5 Tablet Immediate-Release Oral Dosage Form

Table 1 provides the ingredients for an immediate-release tablet dosage form. The active ingredients are blended with the cellulose until a uniform blend is formed. The smaller quantity of starch is blended with a suitable quantity of water to form a starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen.

The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous technique. Tablets of other strengths may be prepared by altering the ratio of active ingredients to pharmaceutically acceptable carrier, the compression weight, or by using different punches.

TABLE 1

| Component | Quantity per Tablet (mg) | | | | |
|---|---|---|---|---|---|
| | Formula A | Formula B | Formula C | Formula D | Formula E |
| Racemic O-desmethyltramadol HCl | 40 | 40 | 20 | 20 | 20 |
| Racemic tramadol HCl | 0 | 30 | 15 | 12.5 | 10.0 |
| Microcrystalline cellulose NF | 114.5 | 84.5 | 119.5 | 122 | 124.5 |
| Starch NF | 30 | 30 | 30 | 30 | 30 |
| Pregelatinized maize starch NF | 15 | 15 | 15 | 15 | 15 |
| Magnesium stearate | 0.5 | 0.5 | 0.5 | 0.5 | 0.5 |
| Compression Weight | 200 | 200 | 200 | 200 | 200 |

Example 6 Human Single-Dose Pharmacokinetics of Immediate Release Tramadol and O-Desmethyltramadol An 88 kg healthy male subject who met certain inclusion/exclusion criteria was enrolled in an open-label pharmacokinetic study. The subject has a CYP2D6*1/*4 intermediate metabolizer genotype (±35% of population). He received a 100 mg oral dose of racemic tramadol HCl in the form of a commercially available immediate-release tablet (i.e., two 50 mg Ultram® tablets, the reference listed drug per FDA Orange Book), followed by escalating weekly oral doses of racemic O-desmethyltramadol HCl given as the liquid immediate-release oral dosage form (i.e., Solution A from Example 4). In vitro dissolution data for the Ultram® tablets were obtained by us per the FDA CDER method database. In vitro dissolution of the immediate-release Ultram® tablets was 70% at 10 min, and 100% at 20 min.

All doses were separated by a 7 day washout period. In particular, after an overnight fast, the subject received a single oral dose of 100 mg racemic tramadol HCl consisting of two 50 mg tablets of a commercial immediate-release formulation with tap water. Seven days later, the same subject received a single oral dose of 20 ml of 1 mg/ml O-desmethyltramadol HCl fully solubilized in water (i.e., Solution A, 20 mg dose total), followed by the ingestion of additional tap water. Seven days after that, the same subject received a single oral dose of 40 ml of 1 mg/ml O-desmethyltramadol HCl fully solubilized in water (i.e., Solution A, 40 mg dose total), followed by the ingestion of additional tap water. No food was allowed until 4 hours after administration.

For pharmacokinetic analysis, venous blood samples with EDTA as anticoagulant were taken before each dosing and at 0.5, 1, 1.5, 2, 3, 4, 6, 8, 10, 12, and 24 hours after each dosing. Samples were centrifuged, and the plasma collected and stored frozen at −20° C. for analysis. There was no urine sampling in this study.

Tramadol and O-desmethyltramadol in plasma samples were quantitated by an LC/MS assay using an internal standard consisting of isotopically labeled tramadol (Cantest, Burnaby, British Columbia, Canada). The quantitation range of the LC/MS assay was 1.00-500 ng/mL for both tramadol and O-desmethyltramadol.

Figure 1A:
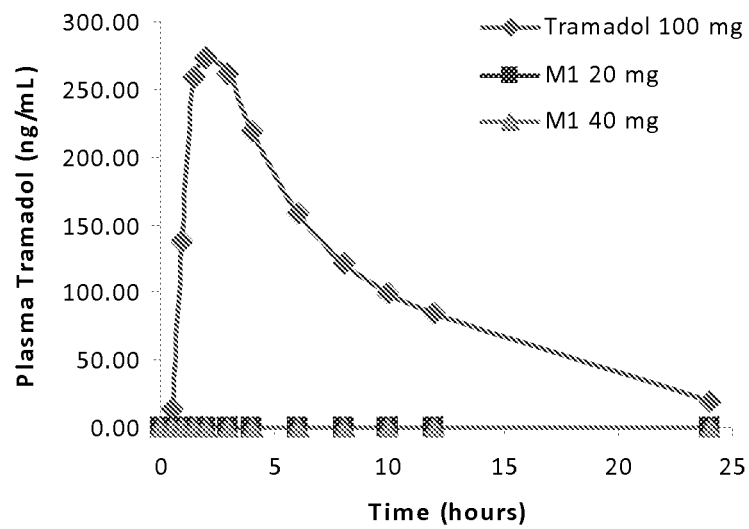
FIG. 1A shows a graphical representation of plasma tramadol in a subject after a single oral dose of IR forms of 100 mg racemic tramadol (Ultram® tablets) and 20 mg and 40 mg racemic O-desmethyltramadol.
Figure 1B:
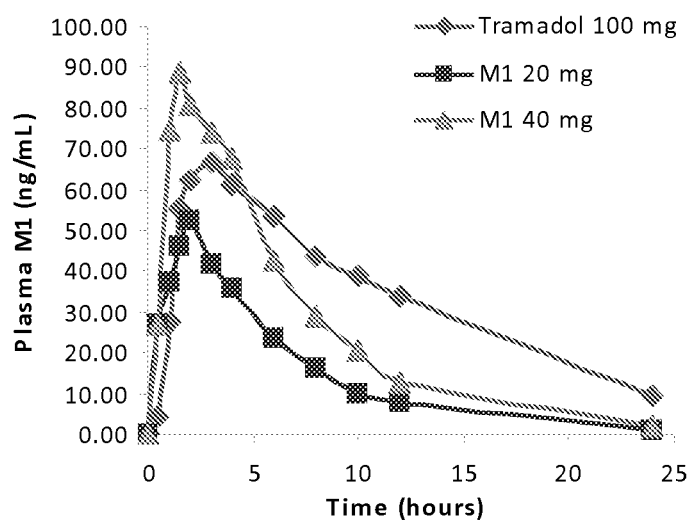
FIG. 1B shows a graphical representation of plasma O-desmethyltramadol concentrations in the same subject as in FIG. 1A after a single oral dose of IR forms of 100 mg racemic tramadol (Ultram® tablets) and 20 mg and 40 mg racemic O-desmethyltramadol.

Noncompartmental methods of analysis were used to calculate pharmacokinetic parameters using PK Solutions Version 2.0. The method of residuals (i.e., curve stripping or feathering) was used to resolve the concentration-time profile curve of parent or M1 into a series of exponential terms corresponding to the absorption, distribution, and elimination phases occurring during the time course in the blood. These exponential terms were then used to calculate the single-dose pharmacokinetic parameters following well established formulae. The single-dose pharmacokinetic data from this study are shown graphically in FIG. 1A for plasma tramadol and FIG. 1B for plasma M1, and the single-dose pharmacokinetic parameters summarized in Table 2.

The single-dose pharmacokinetic parameters for this male subject obtained for 100 mg tramadol agreed well with the mean single-dose pharmacokinetic parameters in the drug labeling (label data for parent: $C_{max}$=308 ng/mL; $T_{max}$=1.6 hr; half-life=5.6 hr; and label data for M1: $C_{max}$=55 ng/mL; $T_{max}$=3.0 hr; half-life=6.7 hr). However, compared with immediate-release tramadol, the half-life of plasma M1 from immediate-release M1 was surprisingly very different, being significantly reduced by about half. Without wishing to be limited by theory, it is hypothesized that this is due to tramadol serving as a circulating slow-release depot for M1, where tramadol is a prodrug that is metabolized in the liver slowly over time.

TABLE 2

| Substance Dosed | Dose (mg) | Dosage (mg/kg) | $AUC_{(0-t)}$ (hr-ng/mL) | AUC (hr-ng/mL) | $T_{max}$ (hr) | $C_{max}$ (ng/mL) | Clearance (ml/hr/kg) | Half-Life (hr) |
|---|---|---|---|---|---|---|---|---|
| Tramadol HCl | 100 | 1.14 | 2463* | 2626* | 2.0 | 274* | 433* | 5.9* |
| | | | 812** | 906** | 3.0 | 66.8** | 1255** | 7.1** |
| M1 HCl | 20 | 0.23 | 351 | 357 | 2.0 | 52.3 | 638 | 4.1 |
| M1 HCl | 40 | 0.46 | 619 | 633 | 1.5 | 88.6 | 719 | 4.4 |

*The parent, tramadol.
**The M1 metabolite, O-desmethyltramadol.

The human data for tramadol and its M1 metabolite in this example demonstrated, (i) efficient oral bioavailability of M1 in the human that does not depend on tramadol metabolism, and (ii) a correlation between the M1 AUC for an oral M1 dose vs. an oral tramadol dose (i.e., 40 mg of M1 yielded an M1 AUC about 70% of that obtained from 100 mg tramadol).

Example 7 Human Steady-State Pharmacokinetics of Immediate Release Tramadol and O-Desmethyltramadol The same 88 kg healthy male subject in Example 6 was enrolled in an open-label steady-state pharmacokinetic study. He received 10 consecutive oral doses with water every 6 hours (sufficient to reach steady-state) of either 25 mg, 50 mg, 75 mg or 100 mg racemic tramadol HCl in the form of a half, 1 whole, 1 whole and 1 half, or 2 whole tablets of the commercially available immediate-release tablet formulation (i.e., 50 mg Ultram®), respectively. In addition to these four ten-dose sequences, he also received a dosing sequence consisting of 10 doses every 6 hours of 20 mg racemic O-desmethyltramadol HCl given as an immediate-release gelatin capsule containing 20 mg O-desmethyltramadol HCl powder (i.e., '20 mg M1 IR'). Each ten-dose sequence was separated by at least a 12 hour washout, although a washout period was not strictly required in this study since steady-state is established by the $8^{th}$ dose, a time when there is effectively no remnant of the previous sequence. There were no food or fasting restrictions.

For pharmacokinetic analysis, 23 venous blood samples (EDTA) were taken at 0.0, 0.25, 0.50, 0.75, 1.0, 1.25, 1.5, 2, 3, 4, 5 and 6 hours after the $9^{th}$ and 0.25, 0.50, 0.75, 1.0, 1.25, 1.5, 2, 3, 4, 5 and 6 hours after the $10^{th}$ doses (i.e., the 6 hour time point of the $9^{th}$ dose is equivalent to the 0.0 time point for the $10^{th}$ dose). Samples were centrifuged, and the plasma collected and stored frozen at $-20°$ C. for analysis. There was no urine sampling in this study. Tramadol and O-desmethyltramadol in plasma samples were quantitated by an LC/MS assay (Warnex, Canada).

Figure 2A:
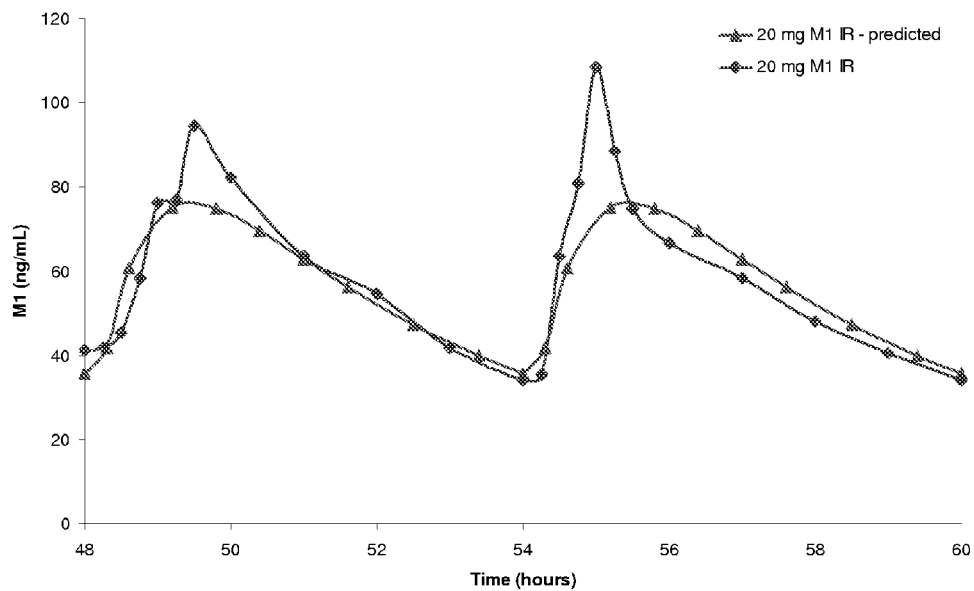
FIG. 2A shows a graphical representation of (A) predicted (based on single-dose pharmacokinetic parameters) and actual plasma O-desmethyltramadol concentrations in the subject after having received 10 doses of 20 mg IR O-desmethyltramadol every 6 hours ($9^{th}$ and $10^{th}$ dose shown).
Figure 2B:
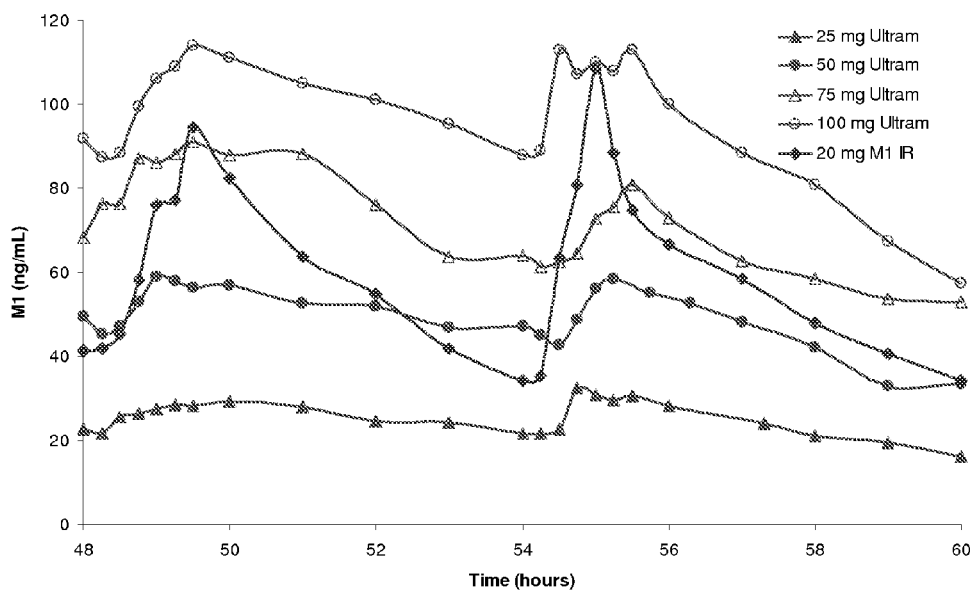
FIG. 2B shows the same plasma profile for the 20 mg O-desmethyltramadol IR formulation as in FIG. 1A vs. the plasma O-desmethyltramadol concentrations in the same subject after having received 10 doses of 25, 50, 75 or 100 mg IR tramadol (Ultram® tablets) every 6 hours ($9^{th}$ and $10^{th}$ dose shown).

The steady-state pharmacokinetic data for the plasma M1 concentrations from this study are shown graphically in FIG. 2A and the steady-state pharmacokinetic parameters for the plasma parent and FIG. 2B for M1 concentrations, as summarized in Table 3. The steady-state pharmacokinetic parameters for this male subject dosed with 100 mg racemic tramadol HCl agreed well with the mean steady-state pharmacokinetic parameters for the same dose in the drug labeling (label data for parent: $C_{max}$=592 ng/mL; $T_{max}$=2.3 hr; and label data for M1: $C_{max}$=110 ng/mL; $T_{max}$=2.4 hr).

Ultram® (i.e., $\Delta Css$=41 ng/mL). Furthermore, the values for $Css_{max}$ and $Css_{min}$ traversed and undershot the M1 therapeutic window provided by Ultram® dosing per label (i.e., 50 to 100 mg q 6 hrs). Thus, both the single-dose and steady-state plasma M1 profiles for M1 administered as an immediate-release formulation were surprisingly very different than the plasma M1 profiles provided by therapeutically effective doses of racemic tramadol HCl administered as an immediate-release formulation (i.e., Ultram® tablets). Again, without wishing to be limited by theory, it is hypothesized that when M1 is administered directly as an immediate release formulation it is rapidly cleared by liver metabolism and renal excretion. In contrast, when tramadol is administered as an immediate release formulation, it serves as the molecular equivalent of a circulating slow-release depot for M1, prolonging the release of M1 and thus dampening the difference between $Css_{max}$ and $Css_{min}$ plasma M1 concentrations during dose cycles.

Figure 3:
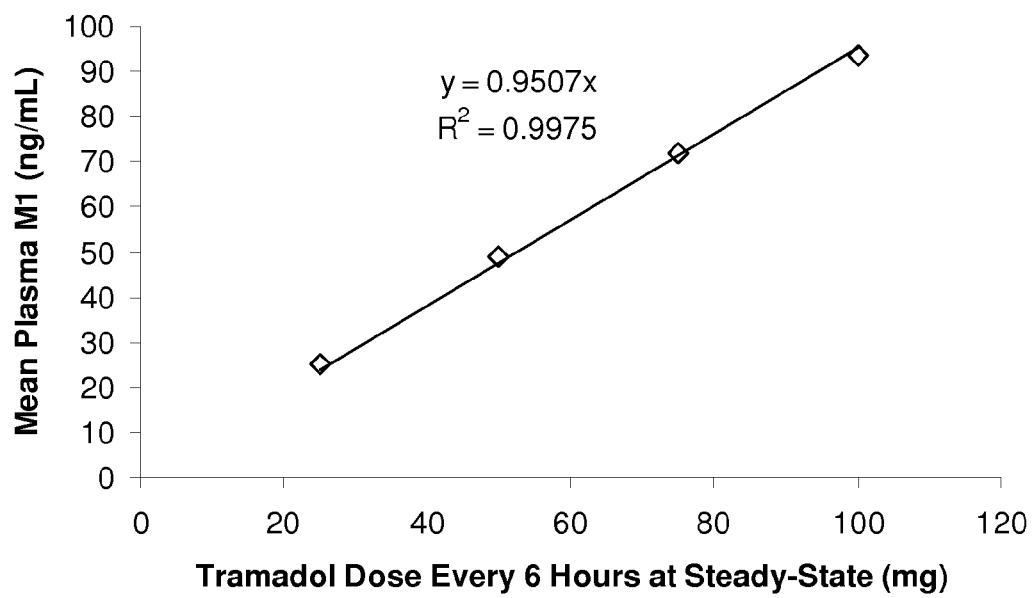
FIG. 3 shows a graphical representation of the mean plasma O-desmethyltramadol (M1) concentration as a function of dose of IR tramadol (Ultram® tablets) given every 6 hours for the 9$^{th}$ and 10$^{th}$ dose data from FIG. 2 (i.e., mean M1 during hours 48-60 from start of dosing).

FIG. 3 shows the mean steady-state M1 plasma concentration during doses 9 and 10 as a function of the dose of racemic tramadol HCl administered as an immediate-release formulation (i.e., Ultram® tablets). There was excellent linear dose proportionality for mean plasma M1 as a function of tramadol dose (mean M1=0.95.times.dose, $R^2$=0.9975).

TABLE 3

| Substance[†] | Dose (mg) | Dose 9 $Css_{min}$ (ng/mL) | Dose 9 $Css_{max}$ (ng/mL) | Dose 10 $Css_{min}$ (ng/mL) | Dose 10 $Css_{max}$ (ng/mL) | Mean* $Css_{min}$ (ng/mL) | Mean* $Css_{max}$ (ng/mL) | Mean* $\Delta Css$ (ng/mL) | $T_{max}$* (hr) |
|---|---|---|---|---|---|---|---|---|---|
| Plasma M1 | | | | | | | | | |
| Tramadol HCl | 25 | 22 | 29 | 16 | 33 | 19 | 31 | 12 | 1.38 |
| Tramadol HCl | 50 | 45 | 59 | 33 | 58 | 39 | 59 | 20 | 1.13 |
| Tramadol HCl | 75 | 64 | 91 | 53 | 81 | 58 | 86 | 28 | 1.50 |
| Tramadol HCl | 100 | 88 | 114 | 58 | 113 | 73 | 114 | 41 | 1.50 |
| M1 HCl | 20 | 34 | 94 | 34 | 108 | 34 | 101 | 67 | 1.25 |
| Plasma Parent | | | | | | | | | |
| Tramadol HCl | 25 | 53.6 | 101 | 50.5 | 137 | 52 | 119 | 67 | 1.00 |
| Tramadol HCl | 50 | 136 | 269 | 141 | 294 | 139 | 282 | 143 | 1.13 |
| Tramadol HCl | 75 | 198 | 368 | 193 | 438 | 196 | 403 | 208 | 1.38 |
| Tramadol HCl | 100 | 316 | 560 | 310 | 627 | 313 | 594 | 281 | 1.13 |
| M1 HCl | 20 | ND | ND | ND | ND | ND | — | — | — |

[†]All in immediate-release (IR) forms.
*Mean of dose 9 and dose 10.
ND = Not detected.
$\Delta Css = Css_{max} - Css_{min}$.

FIG. 2A shows the steady-state plasma M1 profile for the 20 mg M1 IR formulation vs. the predicted steady-state plasma M1 profile based on the single-dose pharmacokinetic parameters for Solution A from Example 6. FIG. 2B shows the steady-state plasma M1 profile for the 20 mg M1 IR formulation vs. the steady-state plasma M1 profile for the different doses of the commercially available immediate-release tramadol tablet (Ultram® tablets).

Compared to Ultram® tablets, the steady-state plasma profile for 20 mg IR M1 revealed a large difference in the mean steady-state maximum ($Css_{max}$) and mean steady-state minimum ($Css_{min}$) plasma M1 concentrations (i.e., $\Delta Css$) during dose cycles 9 and 10 (i.e., 67 ng/mL) that exceeded the corresponding value for even the largest dose of Part III. Sustained-Release Dosage Forms Example 8 Sustained Release Oral Dosage Forms IIIa A series of monolithic sustained release (SR) formulations based on CDT® technology as described in U.S. Pat. No. 6,090,411 were developed.

Manufacturing.

M1.HCl SR tablets were prepared through dry-blend and direct compression. The raw materials minus the lubricant were screened through a 30 mesh sieve and charged in a V-blender (Patterson-Kelly/Harsco Corporation. East Stroudsburg, Pa.) for 10 minutes of blending. The lubricant was then screened through a 30 mesh sieve and added to the mix for an additional 3 minutes of blending time. Batch formulae are depicted in Table 4.

The dissolution kinetics of formulations SR100 to SR105 were substantially independent of pH, with data from SR100 shown in FIG. 4 as being representative. In vitro dissolution

TABLE 4

| Formulation (mg/tablet) | | | SR Dosage Forms | | | | | |
|---|---|---|---|---|---|---|---|---|
| Raw Material | Purpose | Manufacturer | SR100 | SR101 | SR102 | SR103 | SR104 | SR105 |
| M1 HCl | API | In-House | 20.0 | 20.0 | 20.0 | 40.0 | 40.0 | 40.0 |
| HPMC K4M | Polymer | Colorcon | 25.0 | 25.0 | 50.0 | 25.0 | 50.0 | 100.0 |
| Na Citrate | Electrolyte | Gadot | 12.5 | 12.5 | — | 25.0 | 25.0 | — |
| Na Bicarbonate | Electrolyte | Natrium | — | — | 25.0 | — | — | 50.0 |
| Avicel MCC PH 102 | Flow Agent | FMC | 50.0 | 75.0 | 50.0 | 100.0 | 150.0 | 100.0 |
| Mg Stearate | Lubricant | Mallinckrodt | 1.5 | 1.5 | 1.5 | 3.0 | 3.0 | 3.0 |
| Total mg/tablet | | | 109.0 | 134.0 | 146.5 | 193.0 | 268.0 | 293.0 |
| | | | | | Compression | | | |
| Pre-compression (KN) | | | 0 | 0 | 0 | 0 | 0 | 0 |
| Main compression (KN) | | | 10 | 10 | 10 | 10 | 17 | 12 |
| Full travel ejection (N) | | | 80 | 80 | 80 | 80 | 80 | 80 |
| Take-off (N) | | | 1 | 1 | 1 | 1 | 1 | 1 |
| Turret speed (rpm) | | | 10 | 10 | 45 | 45 | 45 | 40 |
| Tooling | | | A | A | A | A | B | C |

Punch and die codes (Natoli Engineering):
A = 0.2812" (HOB 91270);
B = 0.2347" × 0.5501" (HOB 67146);
C = 0.2812" × 0.5000" (HOB 58651).
HPMC = hydroxypropylmethyl cellulose;
MCC = microcrystalline cellulose.

The blend was charged to the hopper of a Piccola (Riva) 10-station rotary press (Specialty Measurements Inc. Lebanon, N.J.). The rotary press was fitted with the appropriate punch and die tooling and instrumented with main compression, pre-compression, ejection, take-off and turret speed sensors. Settings for each batch are summarized in Table 4.

Tablet Characterization.

The mean physical characteristics: weight, thickness, hardness and friability were tested along with in vitro dissolution testing in various physiological relevant media of pH 1.2, 4.5 and 7.2 (Table 5). Dissolution of each SR formulation was determined with six tablets per formulation using a USP Type I dissolution assembly (VanKel VK-7000, Cary, N.C.) with a paddle speed of 75.+−0.0.1 rpm and bath temperature of 37.0.+−0.0.5° C. The dissolution medium was 900 mL of 0.1N HCl; pH 1.2, 0.05M Acetate Buffer; pH 4.5 or 0.05M Phosphate Buffer; pH 7.2 (6 replicates per pH). Samples were detected on-line each hour throughout the duration of release using a UV/vis spectrophotometer at 270 nm (Varian Cary 50, Cary, N.C.). Maximum absorbance values after a 1 hour infinity spin were used to calculate release.

kinetics that are independent of pH is considered evidence that in vivo dissolution kinetics will likewise be independent of pH, and thus unaffected by variations in gastrointestinal motility and pH. This is considered a desirable property for an SR tablet that improves consistency of in vivo release kinetics from subject-to-subject and from dose-to-dose in the same subject.

The dissolution data of formulations SR100, SR101 and SR102 are depicted in FIG. 5A, with select data from testing presented in Table 5. The dissolution data of formulations SR103, SR104 and SR105 are depicted in FIG. 5B, with select data from testing presented in Table 5. As shown in the inset to FIG. 5B, plots of the fraction M1 released as a function of the square root of time (t charts) reveal linear correlations ($R^2 > 0.99$) consistent with these formulations conforming to Higuchi release kinetics (Higuchi T. 'Mechanism of sustained action medication: theoretical analysis of rate of release of solid drugs dispersed in solid matrices' J Pharm Sci. 1963; 52:1145-1149).

The SR100 to SR102 series was designed to substantially replicate at half the M1 HCl dose (i.e., 20 mg vs. 40 mg M1

TABLE 5

| | SR Dosage Forms | | | | | |
|---|---|---|---|---|---|---|
| Characterization | SR100 | SR101 | SR102 | SR103 | SR104 | SR105 |
| *Weight (mg) | 115.4 | 137.7 | 151.7 | 194.0 | 280.0 | 300.9 |
| *Thickness (inch) | 0.120 | 0.132 | 0.134 | 0.175 | 0.158 | 0.175 |
| *Hardness (kp) | 7.6 | 11.5 | 10.1 | 10.1 | 13.8 | 13.9 |
| *Friability (% loss) | 0.28% | 0.09% | 0.05% | 0.07% | 0.13% | 0.20% |
| **Dissolution in vitro | | | | | | |
| Hrs to release 25% | 0.29 | 0.34 | 0.53 | 0.34 | 0.45 | 1.0 |
| Hrs to release 50% | 1.0 | 1.4 | 2.2 | 1.1 | 1.7 | 3.0 |
| Hrs to release 75% | 2.0 | 3.1 | 4.7 | 2.3 | 3.9 | 7.0 |
| Hrs to release >90% | 3.0 | 5.1 | 7.4 | 3.2 | 5.7 | 12.0 |

*Mean.
**The hours ('Hrs') to the indicated % dissolution in vitro were determined from an equation (power or polynomial) fitted ($R^2 > 0.99$ for all) to the mean dissolution data for all media (i.e., pH 1.2, 4.5 and 7.2).

HCl) the dissolution kinetics of the SR103 to SR105 series, respectively. The direct comparisons of each SR form at 20 mg and 40 mg dose strength, confirms that the dissolution kinetics of SR100 is similar to that of SR103 (FIG. 6A), and SR101 is similar to that of SR104 (FIG. 6B), and SR102 is similar (but less so than the other two pairs) to that of SR105 (FIG. 6C).

Example 9 Sustained Release Oral Dosage Forms IIIb

A series of sustained release (SR) formulations comprising uncoated and coated hydrophilic polymer cores were developed. Except for SR311, that delivered a 20 mg M1 HCl dose, all others in this section delivered a 40 mg HCl dose or the molar equivalent of the M1 free base.

Materials.

All materials utilized for the preparation of tablets were pharmaceutical grade.

Active pharmaceutical ingredients (API) M1 (i.e., the free base) and M1 HCl were obtained in house using syntheses described above. Tramadol HCl extended release tablets (i.e., Ultram ER®) were procured from Par Pharmaceuticals (Woodcliff, N.J.) and used as a control.

Tablet Manufacture.

Table 6, Table 7 and Table 8 list the excipient sources and compositions of M1 and M1 HCl tablets prepared. Except for formulation SR311, all powders were ground and screened through a 325 μm mesh screen. Formulations were prepared in 3-5 g batches. Powders for each formulation were premixed in a V-blender for 30 min. A 7 mm biconvex tooling and die set was used for compression of the powders. Each biconvex tablet was individually compressed on a Carver press (Model C, Fred S. Carver Press, Menomonee Falls Wis.) at 5000±100 lbs of force and a dwell time of 30 sec for tablets containing HPMC K4M Premium CR and at 3000±100 lbs of force and a dwell time of 30 sec for tablets containing Kollidon SR. All tablets were allowed to stand at room temperature overnight in a sealed scintillation vial to allow for any elastic recovery.

Formulation SR311 was prepared through dry-blend and direct compression. The raw materials minus the lubricant were screened through a 30 mesh sieve and charged in a V-blender (Patterson-Kelly/Harsco Corporation. East Stroudsburg, Pa.) for 10 minutes of blending. The lubricant was then screened through a 30 mesh sieve and added to the mix for an additional 3 minutes of blending time. The blend was charged to the hopper of a Piccola 10-station rotary press (Specialty Measurements Inc. Lebanon, N.J.). Due to the extremely small amount of blend, the blend was manually fed into the die to reduce waste of material. The tooling used was a round shaped, stainless steel punch and die with a 0.1875" diameter from Elizabeth Carbide. The rotary press was instrumented with main compression, pre-compression, ejection, take-off and turret speed sensors. Pre compression was set to zero, main compression was measured to be ±1.2 KN (maximum compression for tooling is 3.94 KN), full travel ejection was measured at ±80N, take-off averaged ±1N and the turret speed ran at 10 rpm.

TABLE 6

| Formulation (% w/w) | | | SR Dosage Forms | | | | | |
|---|---|---|---|---|---|---|---|---|
| Raw Material | Purpose | Manufacturer | SR201 | SR202 | SR203 | SR204 | SR205 | SR206 |
| M1 (free base) | API | In-House | 39.02 | 39.02 | 39.02 | 39.02 | 39.02 | — |
| M1 HCl | API | In-House | — | — | — | — | — | 39.02 |
| Avicel MCC PH 101 | Binder/Filler | FMC | 48.79 | 39.04 | 29.26 | 19.53 | 9.77 | 19.53 |
| HPMC K4M | Hydrogel | Dow | 9.76 | 19.51 | 29.29 | 39.02 | 48.78 | 39.02 |
| Colloidal Silica | Glidant | Cabot | 1.46 | 1.46 | 1.46 | 1.46 | 1.46 | 1.46 |
| Mg Stearate | Lubricant | Mallinckrodt | 0.97 | 0.97 | 0.97 | 0.97 | 0.97 | 0.97 |
| | Total % | | 100 | 100 | 100 | 100 | 100 | 100 |
| | Tablet (mg) | | 102.5 | 102.5 | 102.5 | 102.5 | 102.3 | 102.5 |

HPMC = hydroxypropylmethyl cellulose;
MCC = microcrystalline cellulose.

Tablet Coating.

Where indicated in Table 7, tablets were coated on a pilot scale pan coater (Bolden, Chicago, Ill.). The rotation speed was set to 60 rpm. A Wheaton bench top glass atomizer/sprayer was placed 30 cm from the bed of the coating pan with a constant flow rate of 10 ml/min. The coating solution was prepared by dissolving the polymer, plasticizer and/or pore former in acetone. Coating was performed until the desired gain in tablet weight was achieved. A heat gun that had been set at 45° C. was employed for drying the coating solution after application on the tablets. The coated tablets were placed in an oven at 45° C. for 1 hr and then allowed to stand overnight at room temperature.

TABLE 7

| Formulation (% w/w) | | | SR Dosage Forms | | | | | |
|---|---|---|---|---|---|---|---|---|
| Raw Material | Purpose | Manufacturer | SR301 | SR302 | SR303 | SR304 | SR305 | SR306 |
| M1 HCl | API | In-House | 39.02 | 39.02 | 39.02 | 39.02 | 39.02 | 39.02 |
| Avicel MCC PH 101 | Binder/Filler | FMC | 39.02 | 39.02 | 39.02 | 39.02 | 39.02 | 39.02 |
| HPMC K4M | Hydrogel | Dow | 19.51 | 19.51 | 19.51 | 19.51 | 19.51 | 19.51 |

TABLE 7-continued

| | | | | | | | | |
|---|---|---|---|---|---|---|---|---|
| Colloidal Silica | Glidant | Cabot | 1.46 | 1.46 | 1.46 | 1.46 | 1.46 | 1.46 |
| Mg Stearate | Lubricant | Mallinckrodt | 0.97 | 0.97 | 0.97 | 0.97 | 0.97 | 0.97 |
| | Total % | | 100 | 100 | 100 | 100 | 100 | 100 |
| | Uncoated (mg) | | 102.5 | 102.5 | 102.5 | 102.5 | 102.5 | 102.5 |
| Coating | | | | | | | | |
| Acetone* | Solvent | Fisher | — | 500 | 500 | 500 | 500 | 500 |
| Ethylcellulose** | Film Former | Dow | — | 99 | 95 | 90 | 85 | 89 |
| PVP K-25** | Pore Former | ISP | — | | | | | 10 |
| Dibutyl Sebacate** | Plasticizer | Kodak | — | | | | | 1 |
| Triethyl Citrate** | Plasticizer/Pore | Morflex | — | 1 | 5 | 10 | 15 | |
| | Coated (mg) | | — | 113.0 | 112.8 | 112.9 | 112.9 | 107.6 |

HPMC = hydroxypropylmethyl cellulose;
MCC = microcrystalline cellulose;
PVP = poly(vinyl pyrrolidone).
*mL,
**% w/w.

Dissolution Testing Methodology.

Except for formulation SR311, the in vitro release profiles of M1 and M1.HCl from the tablets were examined in pH 1.2 and/or 7.4 buffer solution(s) (900 ml) at 37° C. and 50 rpm using a Hansen's six-station USP Type II paddle dissolution assembly (model SR-8, Hansen Research Corp., CA). The buffer solutions were prepared according to the USP 31/NF 26 procedures (United States Pharmacopeia 31/National Formulary, Vol. 1, p. 813, Washington, D.C.). Aliquots (1 ml each) were withdrawn at predetermined time intervals and immediately replaced with an equal volume of the fresh dissolution medium. The removed sample was diluted with 1 ml of 0.1N HCl and analyzed by high performance liquid chromatography (HPLC) (vide infra). All dissolution tests were performed in triplicate.

TABLE 8

| Formulation (% w/w) | | | SR Dosage Forms | | | | |
|---|---|---|---|---|---|---|---|
| Raw Material | Purpose | Manufacturer | SR307 | SR308 | SR309 | SR310 | SR311 |
| M1 HCl | API | In-House | 33.33 | 36.36 | 40.00 | 44.44 | 32.83 |
| Kollidon ® SR | Matrix Former | BASF | 66.66 | 63.63 | 60.00 | 55.56 | 65.68 |
| Colloidal Silica | Glidant | Cabot | — | — | — | — | 0.99 |
| Mg Stearate | Lubricant | Mallinckrodt | — | — | — | — | 0.49 |
| | Total % | | 100 | 100 | 100 | 100 | 100 |
| | Tablet (mg) | | 120 | 110 | 100 | 90 | 60.90 |

HPMC = hydroxypropylmethyl cellulose;
MCC = microcrystalline cellulose;
Kollidon ® SR = polyvinyl acetate (8 parts w/w) and polyvinylpyrrolidone (2 parts w/w).

HPLC Methodology.

A fully automated Shimadzu SCL-10 chromatographic system, equipped with a $C_{18}$ analytical column (Phenomenex Gemini, 150×3 mm, 110 degrees, particle size 3 μm) was employed. The drug was eluted with a 3:1 (v/v) mixture of water:methanol containing 2% acetic acid and 1% triethylamine. The flow rate was 0.2 ml/min, and the detector was set at 274, 272 or 271 nm for tramadol HCl, M1 HCl and M1 free base, respectively. The drug content in the sample was determined by the absolute calibration curve method.

SR311 Dissolution Testing Methodology.

Dissolution of SR311 was determined with six tablets per formulation using a USP Type I dissolution assembly (Van-Kel VK-7000, Cary N.C.) with a paddle speed of 75±0.1 rpm and bath temperature of 37.0±0.5° C. The dissolution medium was 900 mL of 0.1N HCl, pH 1.2; 0.05M acetate buffer, pH 4.5; or 0.05M phosphate buffer, pH 7.2 (6 replicates per pH). Samples were detected on-line each hour throughout the duration of release using a UV/vis spectrophotometer at 270 nm (Varian Cary 50). Maximum absorbance values after a 1 hour infinity spin were used to calculate release.

Results 1—Uncoated Monolithic HPMC-Based Tablets.

Monolithic HPMC-based tablets were prepared as formulations SR201 to SR206, and data from in vitro dissolution testing in physiological relevant medium of pH 7.4 are shown in Table 9 for SR201 to SR205. Without being limited by theory, it is speculated that the release mechanism for SR201 to SR206 involves (i) the hydration of the tablet and formation of a hydrogel matrix, and (ii) solubilization and subsequent diffusion of the API through the hydrogel matrix. Thus, the higher the HPMC K4M amount, the greater the diffusion barrier and consequently, the slower the drug release. The dissolution kinetics of formulations SR201 to SR205 were dependent on pH, with data from SR204 in media at pH 1.2 and 7.4 being representative. Without wishing to be limited by theory, it was hypothesized that the relative insolubility of the M1 free base makes the dissolution of these formulations highly pH dependent due to pH influencing the rate of conversion to the more soluble M1 HCl salt. The development of SR206 that employed the M1 HCl salt, but otherwise had the same formulation as SR204, was intended to make SR206 dissolution pH independent (dissolution kinetics for SR206 herein are those of SR204 at pH 7.4). Consistent with this notion, the release profile of M1 HCl from another uncoated HPMC K4M-based tablet SR301 was relatively pH independent, with data in media at pH 1.2 and 7.4 shown in FIG. 7. The tramadol HCl extended release (Ultram ER®) control is shown for comparison. The advantages of SR tablet dissolution that is pH independent in terms of consistency of in vivo release kinetics from subject-to-subject, and from dose-to-dose in the same subject have been discussed above.

TABLE 9

| | Hours to Release Indicated Percent of API* Dissolution Medium Having pH = 7.4 | | | | pH Independent |
|---|---|---|---|---|---|
| | 25% | 50% | 75% | >90% | Dissolution |
| SR201 | <0.02 | <0.02 | 0.11 | 1.7 | No |
| SR202 | <0.02 | <0.02 | 0.33 | 3.7 | No |
| SR203 | <0.02 | 0.30 | 1.9 | 7.0 | No |
| SR204 | 0.36 | 1.8 | 4.7 | 9.2 | No |
| SR205 | 3.5 | 8.3 | 13.8 | 19.8 | No |
| SR307 | 0.24 | 1.9 | 6.0 | 14 | Yes |
| SR308 | 0.14 | 1.0 | 3.5 | 8.0 | Yes |
| SR309 | 0.10 | 0.72 | 2.3 | 5.2 | Yes |
| SR310 | 0.04 | 0.38 | 1.5 | 3.7 | Yes |
| SR311 | 0.23 | 1.0 | 3.5 | 7.5 | Yes |

*The hours to the indicated % dissolution in vitro were determined from an equation (power or polynomial) fitted ($R^2$ > 0.99 for all) to the mean dissolution data for the indicated dissolution medium.

Results 2—Coated Tablets.

To further prolong the profile of SR301, coated formulations SR302 to SR305 were developed that had the same tablet core, but were now coated with ethylcellulose containing 1, 5, 10 and 15% of triethyl citrate as a plasticizer. As shown in FIG. 8, these formulations provided sustained release profiles of longer duration than the Tramadol HCl ER (Ultram ER®) control, and consistent with the pH independence seen previously for the same uncoated SR301 core, were pH independent in their coated form with data from SR302 in FIG. 9 being representative.

With the addition of the pore-forming agent PVP K-25 and the substitution of dibutyl sebacate for triethyl citrate as the plasticizer in the coating, the sustained release profile of SR306 shortened and substantially replicated that of the Tramadol HCl ER (Ultram ER®) control as shown in FIG. 10 (note that SR306 contains a different API than the Ultram ER® control). It is known that (i) coated sustained release tablet formulations can be defeated by drug abusers through simple crushing of the tablet, and (ii) maintaining control over dissolution characteristics during commercial manufacturing can be challenging. Accordingly, uncoated monolithic sustained release tablets are generally more preferred over coated sustained release tablets.

Results 3—Uncoated Monolithic Kollidon® Based Tablets.

Monolithic Kollidon® based tablets were prepared as formulations SR307 to SR311, and data from in vitro dissolution testing in physiological relevant medium of pH 7.4 are shown in Table 9, and the release profiles shown in FIG. 11. In all cases, an initial burst release, followed by a slow release of M1 was observed. The dissolution of the Kollidon® based tablets was independent of pH, as shown for SR311 in FIG. 12 as being representative.

Example 10 Human Single-Dose Pharmacokinetics of Sustained Release O-Desmethyltramadol The same 88 kg healthy male subject in Example 6 was enrolled in an open-label single-dose pharmacokinetic study (genotype: CYP2D6*1/*4 intermediate metabolizer, ±35% of population). The subject received a single oral dose of each of 12 different (i) SR formulations and (ii) SR+IR combination formulations having a variety of in vitro dissolution kinetics, as summarized in Table 10. Data for single-dosings of IR controls Tramadol HCl ($T_1$=100 mg) and M1 HCl ($M_1$=20 mg, $M_2$=40 mg) formulations are reproduced from Table 2 for comparison purposes. In addition, the subject received a second single-dosing of the IR Tramadol HCl ($T_2$=100 mg) control.

All doses were separated by at least a one day washout. Food was limited for 30 minutes before and after a dose, but was otherwise not restricted. For pharmacokinetic analysis, venous blood samples with EDTA as anticoagulant were taken before each dosing and over 24 hours after each dosing (typically 14-16 samples). Samples were centrifuged, and the plasma collected and stored frozen at −20° C. for analysis. There was no urine sampling in this study. Tramadol and O-desmethyltramadol in plasma samples were quantitated by an LC/MS assay (Warnex, Canada).

Noncompartmental methods of analysis were used to calculate pharmacokinetic parameters using PK Solutions Version 2.0. The method of residuals (i.e., curve stripping or feathering) was used to resolve the concentration-time profile curve of M1 into a series of exponential terms corresponding to the absorption, distribution, and elimination phases occurring during the time course in the blood. These exponential terms were then used to calculate the single-dose pharmacokinetic parameters following well established formulae. The single-dose pharmacokinetic parameters were then used to calculate predicted steady-state pharmacokinetic parameters, including $Css_{min}$ and $Css_{max}$, and their difference ($\Delta Css$).

TABLE 10

| Form | dose M1 mg | dose tramadol mg | >90% Released Hr | Single-Dose M1 PK Actual | | | | | Steady-State M1 PK Predicted | | |
|---|---|---|---|---|---|---|---|---|---|---|---|
| | | | | $C_{max}$ ng/ml | $T_{max}$ hr | $AUC_{(0-t)}$ ng-hr/ml | $AUC_\infty$ ng-hr/ml | $t_{1/2}$ hr | $Css_{max}$ ng/ml | $Css_{min}$ ng/ml | $\Delta Css$ ng/ml |
| $M_1$ | 20 | — | instant | 52.3 | 2.0 | 351 | 357 | 4.1 | 74 | 36 | 39 |
| $M_2$ | 40 | — | instant | 88.6 | 1.5 | 619 | 633 | 4.4 | 127 | 65 | 62 |
| $T_1$ | — | 100 | 0.3 | 66.8 | 3.0 | 812 | 906 | 7.1 | 163 | 125 | 38 |
| $T_2$ | — | 100 | 0.3 | 54.2 | 3.0 | 587 | 749 | 12 | 120 | 73 | 46 |
| SR103 | 40 | — | 3.8 | 73.1 | 3.0 | 504 | 519 | 4.2 | 108 | 17 | 91 |
| SR104 | 40 | — | 6.9 | 53.8 | 5.0 | 538 | 566 | 6.3 | 94 | 67 | 27 |
| SR105 | 40 | — | 12.2 | 45.1 | 4.0 | 505 | 549 | 6.3 | 98 | 73 | 25 |
| SR310 | 40 | — | 3.7 | 68.5 | 2.0 | 532 | 554 | 5.4 | 105 | 55 | 50 |
| SR308 | 40 | — | 8.0 | 71.6 | 1.5 | 593 | 705 | 10.7 | 133 | 76 | 57 |
| SR206 | 40 | — | 9.2 | 64.1 | 2.0 | 554 | 638 | 11.1 | 105 | 74 | 31 |
| SR307 | 40 | — | 14 | 42.8 | 5.0 | 470 | 544 | 9.2 | 92 | 64 | 28 |
| SR203* | 40 | — | 7.0 | 42.2 | 3.0 | 498 | 630 | 10.8 | 112 | 72 | 41 |

TABLE 10-continued

| Form | dose M1 mg | dose tramadol mg | >90% Released Hr | Single-Dose M1 PK Actual | | | | | Steady-State M1 PK Predicted | | |
|---|---|---|---|---|---|---|---|---|---|---|---|
| | | | | $C_{max}$ ng/ml | $T_{max}$ hr | $AUC_{(0-t)}$ ng-hr/ml | $AUC_\infty$ ng-hr/ml | $t_{1/2}$ hr | $Css_{max}$ ng/ml | $Css_{min}$ ng/ml | $\Delta Css$ ng/ml |
| SR306 | 40 | — | 12.0 | ** | ** | ** | ** | ** | ** | ** | ** |
| SR102 | 20 | | 7.4 | 28.8 | 3.6 | 219 | 229 | 6.0 | 44 | 9 | 36 |
| SR307 + T$_3$ | 40 | 30 | 14 | 61.9 | 2.5 | 526 | 647 | 16 | 103 | 58 | 45 |
| SR105 + T$_3$ | 40 | 30 | 12 | 67.7 | 3.0 | 734 | 892 | 9.9 | 164 | 115 | 49 |

Abbreviations:
M$_1$ = single-dose 20 mg M1 IR (solution A);
M$_2$ = single-dose 40 mg M1 IR (solution A);
T$_1$ = first single-dose 100 mg Tramadol IR (Ultram ®);
T$_2$ = second single-dose 100 mg Tramadol IR (Ultram ®) where T$_1$ and T$_2$ were separated by 25 months (January 2009 vs. February 2011);
T$_3$ = 30 mg Tramadol IR (Ultram ®) given as a combination with an SR formulation;
$\Delta Css = Css_{max} - Css_{min}$;
*M1 free base, dose expressed as HCl salt equivalent;
** Release delayed >12 hr and pharmacokinetic parameters could not be computed.

The single-dose pharmacokinetic parameters and predicted steady-state pharmacokinetic parameters are summarized in Table 10. The pharmacokinetic profiles for the SR+IR combination formulations, SR307+T$_3$ and SR105+T$_3$ are shown graphically in FIG. 13A and FIG. 13B, respectively. The human data in this example demonstrated, (i) that different in vitro dissolution kinetics resulted in different single-dose pharmacokinetic parameters, (ii) that different single-dose pharmacokinetic parameters result in different predicted values for $Css_{min}$, $Css_{max}$ and $\Delta Css$, and (iii) that surprisingly, SR M1+IR tramadol combination formulations with certain dissolution kinetics and certain M1 and tramadol doses substantially replicate the single-dose M1 plasma profile obtained from a single dose of 100 mg tramadol. The latter is in sharp distinction to the very different single-dose M1 plasma profile unexpectedly obtained when M1 was given as an IR formulation versus that from IR tramadol (see FIG. 1B and Example 6).

Example 11 In Vitro-In Vivo Correlation Model of Sustained Release O-Desmethyltramadol In vitro-in vivo correlation (IVIVC) is defined as the correlation between an in vitro drug dissolution profile and its in vivo drug absorption profile. Using the single-dose human pharmacokinetic and in vitro dissolution data for IR and SR dosage forms of M1 herein, an IVIVC model was developed that represented a point-to-point relationship between in vitro dissolution rate and in vivo input rate of M1 for each SR dosage form. The IVIVC model was developed in a two-stage process that consisted of deconvolution and convolution. Deconvolution, convolution and other computations related to developing the IVIVC model were performed in IVIVC$_{--0.1.5}$, a freely distributed software package for IVIVC modeling and validation.

Stage (1)—Deconvolution:

An oral solution of M1 HCl completely dissolved in water was employed to obtain the 'reference plasma concentration profile' for when there is zero delay in dissolution (i.e., no sustained release by definition). In particular, data from the oral dosing of 40 mg M1 dissolved in water (i.e., 40 ml of Solution A from Example 4) was collected in the prescribed comma delimited csv format and submitted to IVIVC$_{--0.1.5}$ as the reference plasma concentration profile. Pharmacokinetic parameters ($k_a$, $k_{el}$, $V_d$) were determined for the reference plasma concentration profile using the Nelder-Mead Simplex algorithm available in IVIVC$_{--0.1.5}$. Using the pharmacokinetic parameters of the reference plasma concentration profile and the in vitro dissolution data for each SR formulation, the fraction of M1 absorbed in vivo as a function of time was predicted for each SR formulation by deconvolution using the Wagner-Nelson method available in IVIVC$_{--0.1.5}$.

Stage (2)—Convolution:

The predicted fraction of M1 absorbed in vivo as a function of time was then convolved to the predicted plasma concentrations by using the convolution method available in IVIVC$_{--0.1.5}$.

TABLE 11

| Formulation | Time (hr) to >90% Released | Mean Prediction Error (%) AUC | Mean Prediction Error (%) $C_{max}$ |
|---|---|---|---|
| Monolithic CDT ® Series | | | |
| SR103 | 3.8 | 5.4% | 4.4% |
| SR104 | 6.9 | 11.8% | 10.1% |
| SR105 | 12.2 | 7.6% | 22.8% |
| Monolithic HPMC Series | | | |
| SR203 | 7.0 | 9.1% | 41.4% |
| SR206 | 9.2 | 15.8% | 34.2% |
| Coated Series | | | |
| SR306 | 12.0 | ** | ** |
| Monolithic Kollidon Series | | | |
| SR307 | 14 | 1.7% | 9.0% |
| SR308 | 8.0 | 22.2% | 31.9% |
| SR310 | 3.7 | 10.8% | 4.3% |

** Release delayed >12 hr and pharmacokinetic parameters could not be computed.

The IVIVC model so developed was validated in IVIVC$_{--0.1.5}$ by evaluating the predictability of the correlation. The average 'prediction error' in $C_{max}$ and AUC for each SR formulation versus the actual data was calculated by IVIVC$_{--0.1.5}$ (Table 11).

The correlation coefficient between the predicted fraction absorbed in vivo and the fraction released in vitro was computed ($R^2=0.80$) for all SR formulations (FIG. 14). The actual versus IVIVC-model-predicted plasma concentration profiles are graphically depicted for each SR formulation series in FIG. 15A, FIG. 15B, and FIG. 15C for monolithic CDT® tablets; FIG. 16A and FIG. 16B for monolithic HPMC tablets; and FIG. 17A, FIG. 17B, and FIG. 17C for monolithic Kollidon® tablets.

Example 12 Human Steady-State Pharmacokinetics of Sustained Release O-Desmethyltramadol The same 88 kg healthy male subject in Example 6 was enrolled in an open-label steady-state pharmacokinetic study. He received 10 consecutive oral doses every 6 hours, each with water (sufficient to reach steady-state), of either SR100, SR101, SR102 or SR311. Each ten-dose sequence was separated by at least a 12 hour washout, although a washout period was not strictly required in this study since steady-state is established by the $8^{th}$ dose, a time when there is effectively no remnant of the previous dosing sequence. There were no food or fasting restrictions.

For pharmacokinetic analysis, 23 venous blood samples (EDTA) were taken at about 0.0, 0.25, 0.50, 0.75, 1.0, 1.25, 1.5, 2, 3, 4, 5 and 6 hours after the $9^{th}$ and 0.25, 0.50, 0.75, 1.0, 1.25, 1.5, 2, 3, 4, 5 and 6 hours after the $10^{th}$ doses (i.e., the 6 hour time point of the $9^{th}$ dose is equivalent to the 0.0 time point for the $10^{th}$ dose). Samples were centrifuged, and the plasma collected and stored frozen at −20° C. for analysis. There was no urine sampling in this study. O-desmethyltramadol in plasma samples was quantitated by an LC/MS assay (Warnex, Canada).

The steady-state pharmacokinetic parameters for the plasma M1 concentrations are summarized in Table 12 for SR100, SR101, SR102 and SR311 (M1 IR HCl is also presented from Example 7 for comparison). The steady-state plasma M1 concentrations for the $9^{th}$ and $10^{th}$ dose of SR102 are shown graphically in FIG. 18. For comparison, FIG. 18 also shows the steady-state plasma M1 profiles from Example 7 for the IR formulations of 20 mg M1 HCl, and 25, 50, 75 and 100 mg tramadol HCl (i.e., the commercially available immediate-release Ultram® tablets).

ence between mean $Css_{max}$ and $Css_{min}$ (i.e., $\Delta Css$) for plasma M1 (Table 12). Surprisingly, the steady-state plasma M1 profile for SR102 substantially replicated the steady-state plasma M1 profile for Ultram® tablets at a dose of between 25-50 mg (FIG. 18), as well as the $\Delta Css$ of 50 mg Ultram® (i.e., 21 vs. 20 ng/mL, compare Table 3 to Table 12).

The human data in this example demonstrated that (i) SR M1 formulations with different in vitro dissolution kinetics resulted in different steady-state pharmacokinetic parameters, and that (ii) surprisingly, SR M1 formulations with certain dissolution kinetics substantially replicate the steady-state M1 plasma profile obtained from steady-state dosing of tramadol. In contrast to the inadequate (i.e., limited or non-existent) M1 plasma profile seen in CYP2D6 poor metabolizers administered tramadol who are resistant to its analgesic effects, SR M1 formulations as provided herein provide an adequate therapeutic M1 profile in all subjects irrespective of their CYP2D6 genotype.

Example 13 Human Steady-State Pharmacokinetics of Sustained Release Combination Formulations The same 88 kg healthy male subject in Example 6 was enrolled in an open-label steady-state pharmacokinetic study. The study was performed, as in Example 12, with the subject administered (i) one SR102 tablet (i.e., 20 mg M1 in a sustained released formulation) simultaneously with 15 mg IR tramadol HCl (i.e., Ultram®), or (ii) two SR102

TABLE 12

| Formula | >90% released (hr) | Dose M1 HCl (mg) | Dose 9 $Css_{min}$ (ng/mL) | Dose 9 $Css_{max}$ (ng/mL) | Dose 10 $Css_{min}$ (ng/mL) | Dose 10 $Css_{max}$ (ng/mL) | Mean* $Css_{min}$ (ng/mL) | Mean* $Css_{max}$ (ng/mL) | Mean* $\Delta Css$ (ng/mL) | $T_{max}$* (hr) |
|---|---|---|---|---|---|---|---|---|---|---|
| | | | | | Plasma M1 | | | | | |
| SR100 | 3.0 | 20 | 39 | 66 | 24 | 75 | 31 | 71 | 40 | 2.5 |
| SR101 | 5.1 | 20 | 43 | 69 | 27 | 62 | 35 | 65 | 30 | 1.6 |
| SR102 | 7.4 | 20 | 31 | 46 | 21 | 48 | 26 | 47 | 21 | 0.9 |
| SR311 | 7.5 | 20 | 40 | 72 | 28 | 59 | 34 | 65 | 31 | 1.25 |
| M1 IR† | instant | 20 | 34 | 94 | 34 | 108 | 34 | 101 | 67 | 1.25 |

*Mean of dose 9 and dose 10.
†From Example 7.
$\Delta Css = Css_{max} - Css_{min}$.

Compared to the 20 mg IR HCl steady-state profile, SR100, SR101, SR102 and SR311 all dampened the differtablets (i.e., 40 mg M1) simultaneously with 30 mg IR tramadol HCl.

TABLE 13

| Substance† | Dose 9 $Css_{min}$ (ng/mL) | Dose 9 $Css_{max}$ (ng/mL) | Dose 10 $Css_{min}$ (ng/mL) | Dose 10 $Css_{max}$ (ng/mL) | Mean* $Css_{min}$ (ng/mL) | Mean* $Css_{max}$ (ng/mL) | Mean* $\Delta Css$ (ng/mL) |
|---|---|---|---|---|---|---|---|
| | | | | Plasma M1 | | | |
| 25 mg T | 22 | 29 | 16 | 33 | 19 | 31 | 12 |
| 50 mg T | 45 | 59 | 33 | 58 | 39 | 59 | 20 |
| 75 mg T | 64 | 91 | 53 | 81 | 58 | 86 | 28 |
| 100 mg T | 88 | 114 | 58 | 113 | 73 | 114 | 41 |
| SR102 + 15 mg T | 57 | 97 | 64 | 74 | 61 | 85 | 24 |
| 2× SR102 + 30 mg T | 149 | 201 | 148 | 185 | 149 | 193 | 44 |
| | | | | Plasma Parent | | | |
| 25 mg T | 53.6 | 101 | 50.5 | 137 | 52 | 119 | 67 |
| 50 mg T | 136 | 269 | 141 | 294 | 139 | 282 | 143 |

TABLE 13-continued

| Substance[†] | Dose 9 Css$_{min}$ (ng/mL) | Dose 9 Css$_{max}$ (ng/mL) | Dose 10 Css$_{min}$ (ng/mL) | Dose 10 Css$_{max}$ (ng/mL) | Mean* Css$_{min}$ (ng/mL) | Mean* Css$_{max}$ (ng/mL) | Mean* ΔCss (ng/mL) |
|---|---|---|---|---|---|---|---|
| 75 mg T | 198 | 368 | 193 | 438 | 196 | 403 | 208 |
| 100 mg T | 316 | 560 | 310 | 627 | 313 | 594 | 281 |
| SR102 + 15 mg T | 61 | 110 | 58 | 99 | 60 | 105 | 45 |
| 2× SR102 + 30 mg T | 133 | 213 | 145 | 238 | 139 | 226 | 87 |

[†]T = IR Tramadol HCl (Ultram ®).
*Mean of dose 9 and dose 10.
ND = Not detected.
ΔCss = Css$_{max}$ − Css$_{min}$.

The steady-state pharmacokinetic parameters for the plasma M1 and parent concentrations are summarized in Table 13 (parameters for Tramadol IR HCl is also presented from Example 7 for comparison). The steady-state plasma M1 concentrations for the 9$^{th}$ and 10$^{th}$ dose of the combination formulations are shown graphically in FIG. 19. The steady-state plasma M1 profiles from Example 7 are shown for comparison for the IR formulations of 25, 50, 75 and 100 mg tramadol HCl (i.e., commercial Ultram® tablets).

The steady-state plasma M1 profile for SR102 plus 15 mg IR tramadol substantially replicated the steady-state plasma M1 profile for Ultram® tablets at a dose of 75 mg (FIG. 19). Surprisingly, when IR tramadol was administered with SR102 as a combination, the average plasma M1 and tramadol levels were greater than predicted based on data for SR102 (Example 12) and IR tramadol HCl (Example 7) administered separately. The actual versus predicted plasma profiles for M1 and tramadol are shown graphically in FIG. 20A and FIG. 20B, respectively.

The human data in this example demonstrated that (i) SR M1 and IR tramadol combination formulations substantially replicate the steady-state M1 plasma profile obtained from steady-state dosing of tramadol, and (ii) SR M1 plus IR tramadol combination formulations have mean plasma M1 and plasma tramadol levels higher than predicted based on levels for each administered individually.

Example 14 Sustained Release Combination Tablets

Two preferred sustained-release (SR) combination tablets are shown in Table 14.

the first SR Layer mixture into the die and precompressing by hand and, after addition of 100 mg of the second IR Layer mixture, finally fully compressing the tablet.

Example 15 Human Steady-State Pharmacokinetics of Sustained Release Combination Tablets Healthy subjects will be enrolled in an open-label steady-state pharmacokinetic study to receive 10 consecutive oral doses every 6 hours, each with water (sufficient to reach steady-state) of: 1 tablet of SR106, 2 tablets of SR106, 1 tablet of SR107, 2 tablets of SR107, 1 tablet tramadol and/or 2 tablets tramadol (each tramadol tablet is an Ultram® 50 mg tablet). Each ten-dose sequence will be separated by at least a 12 hour washout, although a washout period is not strictly required. There will be no food or fasting restrictions. Pharmacokinetic analysis will be as in Example 12. Subjects taking 1-2 tablets of SR106 or SR107 will have an M1 steady-state profile substantially the same irrespective of their CYP2D6 genotype, and within the range of the M1 profile in normal metabolizers taking 1-2 tablets of tramadol. All subjects will be exposed to the parent molecule (i.e., racemic tramadol itself) irrespective of subject CYP2D6 genotype. Thus, irrespective of CYP2D6 genotype, SR106 and SR107 will provide both the M1 metabolite and the parent drug and restore the entire spectrum of opioid and monoaminergic activity seen in normal subjects after dosing with conventional tramadol.

TABLE 14

| Raw Material | Purpose | Manufacturer | Monolithic SR Combination Tablet SR106 SR Core (mg/tablet) | Bilayer SR + IR Combination Tablet SR107 SR Layer (mg/tablet) | Bilayer SR + IR Combination Tablet SR107 IR Layer (mg/tablet) |
|---|---|---|---|---|---|
| M1 HCl | API 1 | In-House | 20.0 | 20.0 | — |
| Tramadol HCl | API 2 | In-House | 15.0 | — | 15.0 |
| HPMC K4M | Polymer | Colorcon | 100.0 | 50.0 | — |
| Na Bicarbonate | Electrolyte | Natrium | 50.0 | 25.0 | — |
| Avicel MCC PH 102 | Flow Agent | FMC | 105.0 | 50.0 | 83.0 |
| Colloidal Silica | Glidant | Cabot | — | — | 1.0 |
| Mg Stearate | Lubricant | Mallinckrodt | 3.0 | 1.5 | 1.0 |
| Total mg/tablet | | | 293.0 | 146.5 | 100.0 |

HPMC = hydroxypropylmethyl cellulose; MCC = microcrystalline cellulose.

SR106 is manufactured as described in Example 8 for SR105. SR107 is prepared by separately homogeneously mixing the raw materials of the SR Layer and IR Layer. The two mixtures are then compressed in a tablet press (Korsch EK0) to provide a bilayer tablet by introducing 146.5 mg of Example 16 Combination Formulations M1 and tramadol combinations that provide suitable therapeutic steady-state plasma M1 and tramadol profiles are shown in Table 15.

TABLE 15

| \multicolumn{10}{c}{X mg M1:Y mg tramadol} |
|---|---|---|---|---|---|---|---|---|---|
| 5:5 | 5:7.5 | 5:10 | 5:12.5 | 5:15 | 5:20 | 5:25 | 5:30 | 5:35 | 5:40 |
| 7.5:5 | 7.5:7.5 | 7.5:10 | 7.5:12.5 | 7.5:15 | 7.5:20 | 7.5:25 | 7.5:30 | 7.5:35 | 7.5:40 |
| 10:5 | 10:7.5 | 10:10 | 10:12.5 | 10:15 | 10:20 | 10:25 | 10:30 | 10:35 | 10:40 |
| 12.5:5 | 12.5:7.5 | 12.5:10 | 12.5:12.5 | 12.5:15 | 12.5:20 | 12.5:25 | 12.5:30 | 12.5:35 | 12.5:40 |
| 15:5 | 15:7.5 | 15:10 | 15:12.5 | 15:15 | 15:20 | 15:25 | 15:30 | 15:35 | 15:40 |
| 20:5 | 20:7.5 | 20:10 | 20:12.5 | 20:15 | 20:20 | 20:25 | 20:30 | 20:35 | 20:40 |
| 25:5 | 25:7.5 | 25:10 | 25:12.5 | 25:15 | 25:20 | 25:25 | 25:30 | 25:35 | 25:40 |
| 30:5 | 30:7.5 | 30:10 | 30:12.5 | 30:15 | 30:20 | 30:25 | 30:30 | 30:35 | 30:40 |
| 35:5 | 35:7.5 | 35:10 | 35:12.5 | 35:15 | 35:20 | 35:25 | 35:30 | 35:35 | 35:40 |
| 40:5 | 40:7.5 | 40:10 | 40:12.5 | 40:15 | 40:20 | 40:25 | 40:30 | 40:35 | 40:40 |

Bolded combinations indicate preferred combinations. The M1 is preferably a SR formulation, and the tramadol is preferably an IR formulation. The M1 formulation is more preferably SR 102.

What is claimed:

1. A method for treating a disorder modulated at least in part by opiate receptor activity or monoamine activity, comprising orally administering every six hours to a subject in need thereof a pharmaceutical composition consisting of a therapeutically effective amount of an active pharmaceutical ingredient and pharmaceutically acceptable carriers in a sustained release dosage form, wherein the active pharmaceutical ingredient consists of O-desmethyltramadol (M1), or a pharmaceutically acceptable salt thereof, wherein the pharmaceutically acceptable carriers consist of a polymer selected from polysaccharide, acrylic resin, polyalkylene glycol, polyvinyl acetate, polyvinylpyrrolidone, protein-derived materials, colloidal silica, and mixtures thereof, 25-90 wt % of microcrystalline cellulose; and, optionally, one or more pharmaceutical excipients selected from the group consisting of salts and magnesium stearate; and wherein the mean difference between minimum and maximum plasma concentration of M1 at steady state (ΔCss) is not more than 40 ng/ml.

2. The method of claim 1, wherein the composition consists of a tablet or capsule.

3. The method of claim 1, wherein the composition consists of a tablet comprising O-desmethyltramadol, hydroxypropylmethylcellulose and microcrystalline cellulose.

4. The method of claim 1, wherein the disorder is selected from a group consisting of acute pain, chronic pain, affective disorders, attention deficit disorders, eating disorders, substance abuse, and urinary incontinence.

5. The method of claim 1, wherein the disorder is acute or chronic pain.

6. The method of claim 1, wherein the subject is a CYP2D6 poor metabolizer or a CYP2D6 ultra-rapid metabolizer.

7. The method of claim 1, wherein the subject has abnormally low CYP2D6 activity or abnormally high CYP2D6 activity.

8. The method of claim 1, wherein the composition produces a steady-state plasma profile of M1 that substantially replicates the steady-state plasma profile of M1 following administration of tramadol.

9. The method of claim 1, wherein ΔCss is not more than 30 ng/ml.

10. The method of claim 1, wherein the composition comprises 5 mg to 100 mg of M1.

11. The method of claim 1, wherein the composition comprises 5 mg to 50 mg of M1.

12. The method of claim 1, wherein the composition comprises 10 mg of M1.

13. The method of claim 1, wherein the composition comprises 20 mg of M1.

14. The method of claim 1, wherein the composition comprises 40 mg of M1.

15. The method of claim 1, wherein the composition comprises (1S,2S)-O-desmethyltramadol or a racemic mixture of (1R,2R)-O-desmethyltramadol and (1S,2S)-O-desmethyltramadol.

16. The method of claim 15, wherein the composition comprises racemic O-desmethyltramadol.

17. The method of claim 15, wherein the composition comprises (1S,2S)-O-desmethyltramadol in the absence of (1R,2R)-O-desmethyltramadol.

18. A method for treating pain in a subject who is a CYP2D6 poor metabolizer or a CYP2D6 ultra-rapid metabolizer, or fails to show tramadol analgesia, or experiences tramadol nausea, comprising administering every six hours to a subject in need thereof a pharmaceutical composition consisting of a therapeutically effective amount of an active pharmaceutical ingredient and pharmaceutically acceptable carriers in a sustained release dosage form, wherein the active pharmaceutical ingredient consists of O-desmethyltramadol, or a pharmaceutically acceptable salt thereof; wherein the pharmaceutically acceptable carriers consist of a polymer selected from polysaccharide, acrylic resin, polyalkylene glycol, polyvinyl acetate, polyvinylpyrrolidone, protein-derived materials, colloidal silica, and mixtures thereof, 25-90 wt % of microcrystalline cellulose; and, optionally, one or more pharmaceutical excipients selected from the group consisting of salts and magnesium stearate; and wherein the mean difference between minimum and maximum plasma concentration of M1 at steady state (ΔCss) is not more than 40 ng/ml.

19. The method of claim 18, wherein composition comprises (1S,2S)-O-desmethyltramadol or a racemic mixture of (1R,2R)-O-desmethyltramadol and (1S,2S)-O-desmethyltramadol.

20. The method of claim 18, wherein the mean difference between minimum and maximum plasma concentration of O-desmethyltramadol at steady state (ΔCss) is not more than 40 ng/ml.

21. The method of claim 1, wherein the subject fails to show tramadol analgesia or experiences tramadol nausea.

* * * * *